United States Patent
Dai et al.

(10) Patent No.: US 7,293,873 B2
(45) Date of Patent: Nov. 13, 2007

(54) PRESBYOPIA CORRECTION USING PATIENT DATA

(75) Inventors: Guangming Dai, Fremont, CA (US); Kingman Yee, San Jose, CA (US)

(73) Assignee: VISX, Incorporated, Santa Clara, CA (US)

(*) Notice: Subject to any disclaimer, the term of this patent is extended or adjusted under 35 U.S.C. 154(b) by 505 days.

(21) Appl. No.: 10/738,358

(22) Filed: Dec. 5, 2003

(65) Prior Publication Data

US 2004/0169820 A1 Sep. 2, 2004

Related U.S. Application Data

(60) Provisional application No. 60/519,885, filed on Nov. 13, 2003, provisional application No. 60/468,387, filed on May 5, 2003, provisional application No. 60/468,303, filed on May 5, 2003, provisional application No. 60/431,634, filed on Dec. 6, 2002.

(51) Int. Cl.
*A61B 3/10* (2006.01)
(52) U.S. Cl. ...................................... 351/205; 351/246
(58) Field of Classification Search ................ 351/200, 351/205, 246, 247, 202, 203, 209
See application file for complete search history.

(56) References Cited

U.S. PATENT DOCUMENTS

| | | | |
|---|---|---|---|
| 5,002,384 A * | 3/1991 | Trachtman | 351/203 |
| 5,533,997 A | 7/1996 | Ruiz | |
| 5,682,223 A | 10/1997 | Menezes et al. | |
| 5,684,560 A | 11/1997 | Roffman et al. | |
| 5,724,258 A | 3/1998 | Roffman | |
| 5,807,377 A | 9/1998 | Madhani et al. | |
| 5,835,192 A * | 11/1998 | Roffman et al. | 351/246 |
| 5,928,129 A | 7/1999 | Ruiz | |
| 6,200,342 B1 | 3/2001 | Tassignon | |
| 6,280,435 B1 | 8/2001 | Odrich et al. | |
| 6,302,877 B1 | 10/2001 | Ruiz | |
| 6,457,826 B1 * | 10/2002 | Lett | 351/161 |
| 6,511,180 B2 | 1/2003 | Guirao et al. | |
| 6,554,429 B1 | 4/2003 | Campin et al. | |
| 6,607,274 B2 | 8/2003 | Stantz et al. | |

(Continued)

FOREIGN PATENT DOCUMENTS

WO  WO 03/032825  4/2003

(Continued)

OTHER PUBLICATIONS

Loewenfeld, Irene, E., *The Pupil: Anatomy, Physiology and Clinical Applications*, vol. 1, (©1993) Wayne State University Press, Detroit, MI, pp. 296, 301-304.

(Continued)

*Primary Examiner*—Huy Mai
(74) *Attorney, Agent, or Firm*—Townsend and Townsend and Crew LLP

(57) ABSTRACT

Methods, devices, and systems establish an optical surface shape that mitigates or treats presbyopia in a particular patient. The combination of distance vision and near vision in a patient can be improved, often based on input patient parameters such as pupil size, residual accommodation, and power need. Iterative optimization may generate a customized corrective optical shape for the patient.

56 Claims, 34 Drawing Sheets

U.S. PATENT DOCUMENTS

| | | | |
|---|---|---|---|
| 6,663,619 B2 | 12/2003 | Odrich et al. | |
| 6,679,606 B2 | 1/2004 | Campin et al. | |
| 6,682,196 B2 | 1/2004 | Sheets, Jr. et al. | |
| 6,740,078 B2 | 5/2004 | Tamayo | |
| 6,808,265 B2 | 10/2004 | Cox | |
| 6,808,266 B2 * | 10/2004 | Youssefi | 351/246 |
| 7,118,214 B2 | 10/2006 | Cox | |
| 2002/0040219 A1 | 4/2002 | Nakamura et al. | |
| 2002/0140902 A1 | 10/2002 | Guirao et al. | |
| 2002/0167643 A1 | 11/2002 | Youssefi | |
| 2003/0199858 A1 | 10/2003 | Schelonka | |
| 2004/0008323 A1 * | 1/2004 | Williams | 351/212 |
| 2004/0246440 A1 | 12/2004 | Andino et al. | |
| 2004/0263786 A1 | 12/2004 | Williams et al. | |

FOREIGN PATENT DOCUMENTS

WO    WO 2004/053568 A1    6/2004

OTHER PUBLICATIONS

Moreira et al., "Multifocal Corneal Topographic Changes with Excimer Laser Photorefractive Keratectomy" *Arch. Ophthalmol.* (1992) 110:994-999.

Vinciguerra et al., "Excimer Laser Photorefractive Keratectomy for Presbyopia: 24-month Follow-up in Three Eyes" *Journal of Refractive Surgery* (198) 14:31-31.

* cited by examiner

Even-Power-Term Polynomials        Normal Polynomials 5 mm pupil 6 mm pupil

PRESBYOPIA CORRECTION USING PATIENT DATA

CROSS-REFERENCES TO RELATED APPLICATIONS

The present application is a nonprovisional claiming priority from U.S. patent application Nos. 60/519,885 filed Nov. 13, 2003; 60/468,387 filed May 5, 2003; 60/468,303 filed May 5, 2003; and 60/431,634 filed Dec. 6, 2002, the entire disclosures of which are incorporated herein by reference for all purposes.

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

This invention generally relates to optical correction, and in particular provides methods, devices, and systems for mitigating or treating presbyopia and other vision conditions, often by scaling, deriving, or generating a prescription to treat a particular patient.

Presbyopia is a condition that affects the accommodation properties of the eye. As objects move closer to a young, properly functioning eye, the effects of ciliary muscle contraction and zonular relaxation allow the lens of the eye to become rounder or more convex, and thus increase its optical power and ability to focus at near distances. Accommodation can allow the eye to focus and refocus between near and far objects.

Presbyopia normally develops as a person ages, and is associated with a natural progressive loss of accommodation, sometimes referred to as "old sight." The presbyopic eye often loses the ability to rapidly and easily refocus on objects at varying distances. There may also be a loss in the ability to focus on objects at near distances. Although the condition progresses over the lifetime of an individual, the effects of presbyopia usually become noticeable after the age of 45 years. By the age of 65 years, the crystalline lens has often lost almost all elastic properties and has only limited ability to change shape. Residual accommodation refers to the amount of accommodation that remains in the eye. A lower degree of residual accommodation contributes to more severe presbyopia, whereas a higher amount of residual accommodation correlates with less severe presbyopia.

Known methods and devices for treating presbyopia seek to provide vision approaching that of an emmetropic eye. In an emmetropic eye, both distant objects and near objects can be seen due to the accommodation properties of the eye. To address the vision problems associated with presbyopia, reading glasses have traditionally been used by individuals to add plus power diopter to the eye, thus allowing the eye to focus on near objects and maintain a clear image. This approach is similar to that of treating hyperopia, or farsightedness.

Presbyopia has also been treated with bi-focal eyeglasses, where one portion of the lens is corrected for distance vision, and another portion of the lens is corrected for near vision. When peering down through the bifocals, the individual looks through the portion of the lens corrected for near vision. When viewing distant objects, the individual looks higher, through the portion of the bi-focals corrected for distance vision. Thus with little or no accommodation, the individual can see both far and near objects.

Contact lenses and intra-ocular lenses (IOLs) have also been used to treat presbyopia. One approach is to provide the individual with monovision, where one eye (usually the primary eye) is corrected for distance-vision, while the other eye is corrected for near-vision. Unfortunately, with monovision the individual may not clearly see objects that are intermediately positioned because the object is out-of-focus for both eyes. Also, an individual may have trouble seeing with only one eye, or may be unable to tolerate an imbalance between their eyes. In addition to monovision, other approaches include bilateral correction with either bi-focal or multi-focal lenses. In the case of bi-focal lenses, the lens is made so that both a distant point and a near point can be focused. In the multi-focal case, there exist many focal points between near targets and far targets.

Surgical treatments have also been proposed for presbyopia. Anterior sclerostomy involves a surgical incision into the sclera that enlarges the ciliary space and facilitates movement of the lens. Also, scleral expansion bands (SEBs) have been suggested for increasing the ciliary space. Problems remain with such techniques, however, such as inconsistent and unpredictable outcomes.

In the field of refractive surgery, certain ablation profiles have been suggested to treat the condition, often with the goal of increasing the range of focus of the eye, as opposed to restoring accommodation in the patient's eye. Many of these ablation profiles can provide a single excellent focus of the eye, yet they do not provide an increased depth of focus such that optimal distance acuity, optimal near acuity, and acceptable intermediate acuity occur simultaneously. Shapes have been proposed for providing enhanced distance and near vision, yet current approaches do not provide ideal results for all patients.

In light of the above, it would be desirable to have improved methods, devices, and systems for treatment and/or mitigation of presbyopia and other optical defects. Optionally, it may be desirable to provide improved prescriptions in the form of practical customized or optimized prescription shapes for treating or mitigating vision conditions such as presbyopia in a particular patient.

BRIEF SUMMARY OF THE INVENTION

The present invention provides improved devices, systems, and methods for mitigating or treating presbyopia and other vision conditions. The present invention can establish a prescription that mitigates or treats presbyopia in a particular patient. In some embodiments, an optically optimized shape may be generated based on patient data input. Typically, the shape will represent a compromise between improved near vision and improved distance vision. These optimized shapes can be derived numerically using input patient parameters such as pupil size, residual accommodation, and desired vergence. Presbyopia-mitigating shapes may be scaled (or otherwise varied) in response to patient data such as one or more pupil diameters. Appropriate scaling may be determined at least in part from prior patient data from patients having differing pupil sizes and/or differing shapes. Advantageously, presbyopia-mitigating prescriptions may be derived from, scaled using, and/or optimized to provide at least one desired optical power (and/or manifest power), often to provide a plurality of optical powers at differing viewing conditions, thereby taking advantage of changes in pupil size when viewing objects under differing viewing conditions such as at differing distances and lighting conditions.

In a first aspect, the invention provides a method for treating existing or potential presbyopia of a patient. The patient has an eye with a pupil, a change in viewing distance with the eye inducing a change in pupil dimension. The method comprises measuring a first dimension of the pupil at a first viewing distance, and determining a first desired power for the eye at the first viewing distance. A prescription for the eye is determined such that the prescription provides the first desired power when the pupil has the first dimension, and such that the prescription effects a desired change in power in response to the change in pupil dimension, the desired change in power mitigating the presbyopia.

In many embodiments, a rate of the desired change in power for the change in pupil dimension comprises from about 0.25 D/mm to about 5.0 D/mm. When the patient is about 45 years old or less, and the rate may comprise from about 0.25 D/mm to about 1.0 D/mm. When the patient is about 60 years old or less the rate may comprise from about 1.0 D/mm to about 5.0 D/mm. A second desired optical power for the eye may be determined at a second viewing distance. At least a third desired optical power for the eye may also be determined, each optical power having an associated viewing condition, with a rate of an incremental desired change in power for an incremental change in pupil size varying within a pupil size range of the patient. The change in pupil dimension of the patient may be measured by measuring a second pupil dimension of the pupil at the second viewing distance, and/or the rate of the desired change in optical power for the change in pupil dimension may be assumed to be consistent for a plurality of patients.

The eye may have a residual accommodation range, and the first desired power for the eye may be determined so that the eye adjusts within the residual accommodation range when viewing at the first viewing distance with the first desired optical power. Optionally, particularly when the patient is about 60 years old or less, the first desired power for the eye and/or the desired change in power may be adjusted in response to an anticipated shrinkage of the pupil with age and/or anticipated reduction of residual accommodation.

The prescription may be determined at least in part by iteratively optimizing a goal function, by scaling a refractive shape, and/or by analytically or numerically deriving an optical shape providing a plurality of desired optical powers at an associated plurality of viewing conditions.

In a system aspect, the invention provides a system for treating existing or potential presbyopia of a patient. The patient has an eye with a pupil, a change in viewing distance with the eye inducing a change in pupil dimension. The system comprises a pupilometer for measuring a first dimension of the pupil while the eye is viewing at a first viewing distance. A prescription generating module has an input accepting a desired power for the eye and the first dimension. The module determines a prescription for the eye providing a first desired power when the pupil has the first dimension, the prescription effecting a desired change in power in response to the change in pupil dimension. The desired change in power mitigates the presbyopia.

The prescription generating module may comprise an optimizer module that determines the prescription based on the pupil diameter and the desired power using a goal function appropriate for the presbyopia; a scaling module that scales a central portion of a prescription shape based on the pupil dimension such that the prescription shape ameliorates presbyopia, and such that the central portion has a dimension between about 0.35 and about 0.55 of the pupil dimension; and/or a prescription calculating module calculating a presbyopia-mitigating prescription for the eye in response to the pupil dimension and the change in pupil dimension so that the eye has the first desired power suitable for the first viewing distance and so that the eye has a second desired power for a second viewing distance. Optionally, a laser may impose the prescription on the eye, typically by ablating corneal tissue.

In another aspect, the invention provides a method for determining a prescription that mitigates or treats presbyopia in a particular patient. The method comprises selecting a goal function appropriate for presbyopia of an eye, inputting a set of patient parameters specific for the particular patient, and determining an optical shape for the particular patient appropriate for differing viewing conditions based on the set of patient parameters per the goal function so as to mitigate or treat the presbyopia in the patient.

The goal function can reflect optical quality throughout a vergence range. The goal function may also comprise a ratio of an optical parameter of the eye with a diffraction theory parameter. Relatedly, the goal function may also comprise at least one parameter selected from the group consisting of Strehl Ratio (SR), modulation transfer function (MTF), point spread function (PSF), encircled energy (EE), MTF volume or volume under MTF surface (MTFV), compound modulation transfer function (CMTF), and contrast sensitivity (CS). The goal function may also be based on geometrical optics. Similarly, the goal function can be determined using ray tracing. In this context, the phrase 'ray tracing' has a meaning identical to 'geometrical optics'. The set of patient parameters can include at least one parameter selected from the group consisting of pupil size, residual accommodation, power need, and vergence. In this context the phrase "power need" has a meaning identical to "vergence."

The prescription may comprise an optical shape determined by inputting a set of patient parameters specific for the particular patient into an optimizer. The shape is derived for the particular patient per a goal function so as to mitigate or treat the presbyopia in the patient. An initial optical shape can be input, the initial shape often being radially symmetric. Relatedly, the radially symmetric shape may be decomposed into a set of polynomials having at least two independent variables. Further, one of the at least two independent variables can be the ratio of the customized shape diameter to pupil diameter. The iterative optimization may be selected from the group consisting of Downhill Simplex method, Direction set method, and Simulated Annealing method, or the like. The set of patient parameters can include at least one parameter selected from the group consisting of pupil size, residual accommodation, and power need.

Optionally, the presbyopia may be treated by administering to the patient a procedure selected from the group consisting of ablating a cornea of the patient to provide a corneal shape that corresponds to the optical shape, providing the patient with a contact lens or spectacle lens that has a shape that corresponds to the optical shape, and providing the patient with an intra-ocular lens that has a shape that corresponds to the optical shape. The optical shape may be determined based at least in part on an expansion such as a regular polynomial (Even-Power-Term polynomials ("EPTP") or non-EPTP), a Zernike polynomial, a Fourier series, and a discrete shape entirety. The expansion may be a 3rd order or 4th order non-EPTP expansion, or a 6th or 8th order EPTP expansion. The optical shape may be determined based at least in part on a presbyopia-add to pupil ratio (PAR), the PAR ranging from about 0.2 to about 1.0.

In another system aspect, the present invention provides a system for establishing a prescription that mitigates or treats presbyopia in a particular patient, where the system includes an input that accepts a set of patient parameters, and a module that determines an optical shape for the particular patient based on the set of patient parameters, using a goal function appropriate for presbyopia of an eye.

The module may include data processing software and/or hardware, and may be optionally integrated with other data processing structures. The module may comprise an optimizer module that determines the prescription for the particular patient based on the set of patient parameters, using a goal function appropriate for presbyopia of an eye. A processor may generate an ablation profile, and a laser system can direct laser energy onto the cornea according to the ablation profile so as to reprofile a surface of the cornea from the first shape to the second shape, the second shape corresponding to the determined optical shape. Pupil diameters may be measured for input under one or more of the following conditions: when focusing on a near object; when focusing on a distant object; under photopic conditions; under mesopic conditions; under scotopic conditions. The prescription shape may be aspherical when the central portion of the prescription shape is aspherical; the prescription shape may be spherical when the central portion of the prescription shape is spherical; the prescription shape may be aspherical when the central portion of the prescription shape is spherical; and/or the prescription shape may be spherical when the central portion of the prescription shape is aspherical, with healing and LASIK flap effects and the like optionally varying the final shape of the eye. The dimension of the prescription shape central portion may comprise a diameter of the central portion and may remain within a range between about 0.4 and about 0.5 of the pupil diameter of the particular patient, or within a range between about 0.43 and about 0.46 of the pupil diameter of the particular patient; a power of the central portion is optionally between about 1.5 diopters and about 4.0 diopters (ideally being about 3.1 diopters).

In another aspect, the invention provides a method for treating presbyopia of an eye of a patient. The method comprises identifying a first pupil size of the eye under a first viewing condition. A second pupil size of the eye is identified under a second viewing condition. A presbyopia-mitigating prescription is calculated for the eye in response to the pupil sizes so that the eye has a first power suitable for the first viewing condition at the first size and so that the eye has a second power suitable for the second viewing condition at the second size.

Calculating the prescription may comprise determining a first effective power of the eye with the first pupil size and calculating a second effective power of the eye with the second pupil size. The first and second pupil diameters may be measured from the eye of the patient while the eye is viewing with the first and second viewing conditions, respectively. The prescription often comprises a prescription shape, and the method may include altering the refraction of the eye according to the prescription shape. The refraction of the eye can be altered using at least one of a laser, a contact lens, an intraocular lens, and a spectacle. One or more additional pupil diameters of the eye may be determined under one or more associated viewing condition, and the prescription can be calculated so that the eye has appropriate powers suitable for viewing at each additional viewing condition.

The prescription may be derived by determining at least one coefficient of a set of Zernike polynomials. Calculating the prescription often comprises determining a plurality of selected Zernike coefficients of spherical aberration at various orders. The eye at the first viewing condition may be viewing at a first viewing distance, and the eye at the second viewing condition may be viewing at a second viewing distance which is less than the first distance, with the second power being more negative than the first power. The eye at the first viewing condition can have a power between 0.25 D and −0.25 D, and the eye at the second viewing condition may have a power between −0.5 D and −3.0 D.

In another aspect, the invention may comprise a method for deriving a prescription for an eye. The method comprises determining a polynomial expansion from a wavefront of an eye, and calculating a plurality of effective powers based on a plurality of expansion coefficients of the polynomial expansion at different viewing pupil sizes. The prescription may be generated so as to provide a plurality of desired effective powers at said pupil sizes.

In yet another aspect, the invention provides a method for determining an effective power of an eye under a viewing condition. The method comprises determining a plurality of coefficients of a Zernike polynomial expansion from a wavefront of an eye while the eye has a first pupil size, and determining a second pupil size of the pupil under the viewing condition. The effective power of the eye is calculated from at least one of the coefficients of the Zernike polynomial from a relationship between effective power and pupil size.

In yet another aspect, the invention provides a system for correcting refraction of an eye, the system comprising at least one input for a first pupil size of the eye under a first viewing condition and a second pupil size of the eye under a second viewing condition. A prescription calculating module calculates a presbyopia-mitigating prescription for the eye in response to the pupil sizes so that the eye has a first power suitable for the first viewing condition at the first size and so that the eye has a second power suitable for the second viewing condition at the second size.

In another aspect, the invention provides a system for deriving a prescription for an eye, the system comprising a polynomial expansion module having an input for a wavefront of an eye and an output for a polynomial expansion. An effective power module has an input coupled to the output of the polynomial expansion module and an output. The effective power module determines an effective power from the polynomial expansion. A prescription module is coupled to the effective power module. The prescription module generates the prescription so as to provide a plurality of different desired effective powers at an associated plurality of different viewing pupil sizes.

In yet another aspect, the invention provides a system for determining an effective power of an eye under a viewing condition, the system comprising a first input for a plurality of coefficients of a Zernike polynomial expansion from a wavefront of an eye while the eye has a first pupil size. A second input accepts a second pupil size of the pupil under the viewing condition. An effective power calculating module calculates the effective power of the eye from at least one of the coefficients of the Zernike polynomial and a relationship between effective power and pupil size.

For a fuller understanding of the nature and advantages of the present invention, reference should be had to the ensuing detailed description taken in conjunction with the accompanying drawings.

DETAILED DESCRIPTION OF THE INVENTION

Although the methods, devices, and systems of the present invention are described primarily in the context of a laser eye surgery system, it should be understood that the techniques of the present invention may be adapted for use in other eye treatment procedures and systems such as contact lenses, intra-ocular lenses, radial keratotomy, collagenous corneal tissue thermal remodeling, removable corneal lens structures, glass spectacles, and the like.

The present invention is useful for enhancing the accuracy and efficacy of photorefractive keratectomy (PRK), laser in situ keratomileusis (LASIK), laser assisted epithelium keratomileusis (LASEK), and the like. The present invention can provide enhanced optical correction approaches by improving the methodology for scaling an optical shape, or by generating or deriving new optical shapes, and the like.

The techniques of the present invention can be readily adapted for use with existing laser systems, including the VISX Excimer laser eye surgery systems commercially available from VISX of Santa Clara, Calif. By providing improved corneal ablation profiles for treating optical defects, the present invention may allow enhanced treatment of patients who have heretofore presented difficult or complicated treatment problems. When used for determining, deriving, and/or optimizing prescriptions for a particular patient, the systems and methods may be implemented by calculating prescriptions for a range of patients, for example, by calculating discrete table entries throughout a range of patient characteristics, deriving or empirically generating parametric patient characteristic/prescription correlations, and the like, for subsequent use in generating patient-specific prescriptions.

Figure 1A:
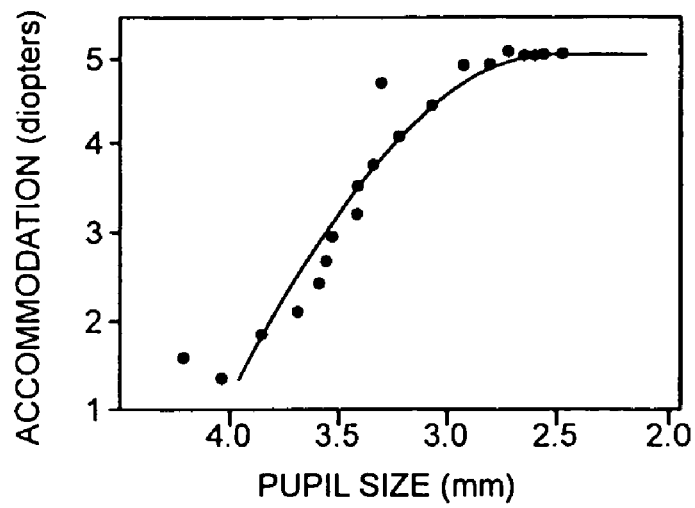
FIG. 1A illustrates a relationship between accommodation and pupil size when healthy eyes adjust to differing viewing distances.

Referring first to FIG. 1A, the present invention will often take advantage of the fact that the eye changes in two different ways with changes in viewing distance: the lens changes in shape so as to provide accommodation, and the pupil size simultaneously varies. Accommodation and pupillary constriction work in unison in normal healthy eyes when shifting from a far to a near viewing distance, and a fairly linear relation may exist between at least a portion of the overlapping constriction and accommodation ranges, but the effect may vary significantly among subjects (from 0.1 to 1.1 mm per diopter). Moreover, when the stimulus for accommodation is increased beyond the eye's ability to change its refraction, the relationship between accommodation of the lens and pupillary constriction may be curvilinear as shown.

While they work in unison, pupillary constriction and accommodation are not necessarily linked. These two functions may proceed independently, and may even work in opposite directions, particularly when the patient is simultaneously subjected to large variations in light intensity with changes in viewing distance. Nonetheless, prescriptions for presbyopia can take advantage of the correlation between pupil dimension and viewing distance for a particular patient. The effective time span for a presbyopia-mitigating prescription may also be extended by accounting for gradual changes in pupil dimension over time (such as the gradual shrinkage of the pupil as one ages) with the concurrent gradual decrease in the accommodation. Details regarding constriction of the pupil were published in a book entitled The Pupil by Irene E. Loewenfeld (Iowa State University Press, 1993).

Figure 1B:
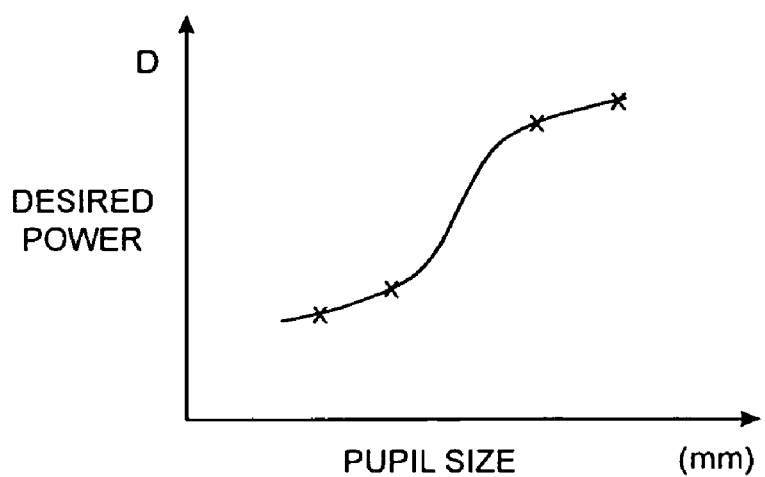
FIG. 1B illustrates one exemplary relationship between effective power of an eye and pupil size for a patient, as can be provided from the presbyopia prescriptions of the present invention by generating an optical shape which effects desired changes in power with changes in pupil size of a particular patient under differing viewing conditions.
Figure 1C:
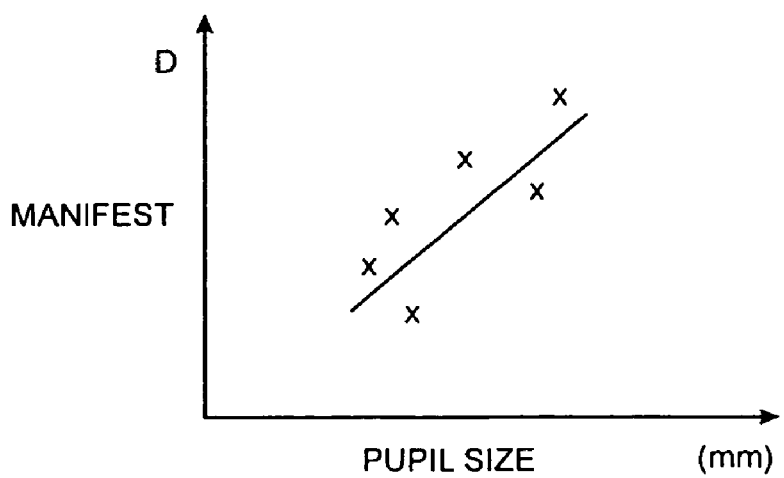
FIG. 1C illustrates a relationship between manifest power and pupil diameter, for example, as measured from patients having differing pupil diameters who have been successfully treated with a presbyopia-mitigating prescription. Such a relationship may be used to identify a desired change in optical power with changes in pupil diameter for a specific patient.

Referring now to FIGS. 1B and 1C, if we assume that we can tailor a beneficial overall optical power for the eye as it changes to different pupil sizes, we may first want to identify a relationship between this desired optical power and pupil size. To determine what powers would be desirable for a particular patient at different viewing conditions, we might measure both the manifest sphere and corresponding pupil sizes of that patient at a variety of different viewing conditions. The manifest sphere may then be used as our desired or effective power to be used for treating presbyopia, as detailed below. The desired optical power might also be determined from the measured manifest, for example, with desired power being a function of the manifest to adjust for residual accommodation and/or anticipated aging effects or the like. In either case, these patient-specific measurements can be the basis for determining desired powers for associated pupil sizes of that patient, such as at the four points illustrated in FIG. 1B. Fewer or more points might also be used.

Alternatively, manifest sphere and pupil size for a population of different patients who have been successfully treated with a given presbyopia prescriptive shape may be plotted, and a correlation derived from this empirical data, as schematically illustrated in FIG. 1C. Still further approaches may be employed, including combinations where a population of patients having differing pupil sizes are used to derive an initial correlation, which is subsequently refined with multiple measurements from at least one patient (and often a plurality of patients). Regardless, the relationship between our desired optical power and the pupil size can be determined. As will be clear from the detailed description below, constriction of the pupil at differing viewing distances then allows the overall power of the eye to be altered by the pupillary constriction, despite a loss in the flexibility of the lens. For example, we can employ a peripheral portion of the ocular system having a different power than a central portion. By understanding the variations of these often aspherical optical systems with changing pupil sizes, we can provide good optical performance throughout a range of viewing distances.

The following description will first provide techniques and devices for iteratively optimizing refraction for treatment of presbyopia. This is followed by a brief review of an exemplary initial laser ablation shape for mitigation of presbyopia, which is in turn followed by an explanation of techniques for optimizing that shape (or other shapes), often using empirical and/or patient-specific information to scale the shape. Generalized analytical and numerical techniques for determining or selecting appropriate presbyopia mitigating prescription shapes will then be provided.

When designing a prescriptive shape for a presbyopia eye treatment, it is useful to select a mathematical gauge of optical quality appropriate for presbyopia for use as a goal function. This allows for quantification and optimization of the shape, and for comparison among different shapes. The present invention provides methods for establishing a customized optical shape for a particular patient based on a set of patient parameters per the goal function. By incorporating iterative optimization algorithms, it is also possible to generate a shape having an optimized level of optical quality for the particular presbyopic patient.

Selecting a Goal Function Appropriate for Presbyopia

The goal function relates to optical quality, and it can be, for example, based on, or a function of (or related to) optical metrics such as Strehl ratio (SR), modulation transfer function (MTF), point spread function (PSF), encircled energy (EE), MTF volume or volume under MTF surface (MTFV), or contrast sensitivity (CS); and optionally to new optical metrics which are appropriate to presbyopia, such as compound modulation transfer function (CMTF) as described below. In optical terms, the goal function should make sense. That is to say, minimization or maximization of the goal function should give a predictable optimized optical quality of the eye. The goal function can be a function with a certain number of free parameters to be optimized (minimized) through an optimization, or minimization, algorithm.

Although there are many types of goal functions available for use with the present invention, the discussion below generally touches on two broad schools of goal functions. In a Diffraction Theory based approach, the shape is considered as a wave aberration. Typically, a Fourier transform is employed for calculating optical quality related parameters, such as Strehl ratio (SR), modulation transfer function (MTF), MTF volume or volume under MTF surface (MTFV), compound modulation transfer function (CMTF), or contrast sensitivity (CS), encircled energy (EE) (based on point spread function), as well as special cases that combine one or more of these parameters, or values of the parameters in specific situations (such as MTF at spatial frequency or encircled energy at a field of view), or integration of any parameters (volume of MTF surface at all frequencies or up to a cutoff frequency, for example 60 cycles/degree or 75 cycles/degree, because 60 cycles/degree is the retina cone's limiting spatial frequency). In a Geometrical Optics approach, or the so-called ray tracing approach, the optical effect is based on ray tracing. With both the Diffraction Theory and the Geometrical Optics approaches, polychromatic point spread function with Stiles-Crawford effect, chromatic aberrations as well as retina spectral response function can be used.

Monochromatic point spread function (PSF) has been used for describing optical defects of optical systems having aberrations. Due to the simple relationship between wave aberrations and the PSF for incoherent light source, Fourier transform of the generalized pupil function has been used in the calculation of point spread functions. Most optical applications, however, do not use a monochromatic light source. In the case of human vision, the source is essentially white light. Thus, there are limitations associated with the use of monochromatic PSF as a goal function.

Polychromatic point spread function (PSF) with correct chromatic aberrations, Stiles-Crawford effect as well as retina response function, can be used for optical modeling of human eyes. Here, chromatic aberrations are due to the fact that light from different wavelength will focus either in front of the retina or behind it. Only portions of the light will focus exactly on the retina. This gives the eye an extended depth-of-focus, i.e., if one has focusing error of some amount, the eye is still capable of focusing at least for some wavelengths. Therefore, chromatic aberrations in fact help the correction of presbyopia. If the depth-of-focus is sufficiently large, there would be no presbyopia problem. Unfortunately, the chromatic aberrations are not large enough and it also varies with the wavelength. Stiles-Crawford effect, also known as pupil apodization, is due to the waveguide property of the retinal cones. Light from the pupil periphery has a slightly less chance of being detected by the retina because the ray of light might not reach the bottom of the cone, due to a slight incident angle. As for the retinal spectral response function, it is known that the cones, which are responsible for daylight vision, have different sensitivity to different wavelengths. Only green light is absorbed by the eye almost completely. Both blue light and red light are absorbed by the eye partially.

Figure 2A:
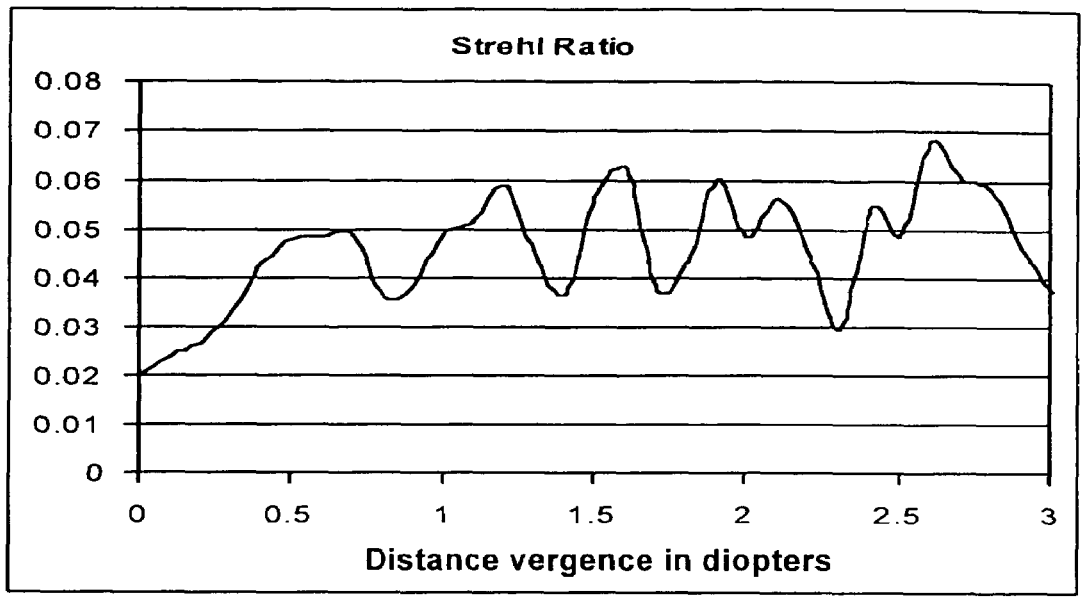
FIGS. 2A-2C graphically illustrate optical properties of an eye relevant to presbyopia.

Once the PSF is calculated, calculation of the Strehl ratio is straightforward. Strehl ratio can be defined as the ratio of the peak of the point spread function (PSF) of an optical system to the peak of a diffraction-limited optical system with the same aperture size. An example of a Strehl ratio is shown in FIG. 2A. A diffraction-limited optical system is typically a system with no aberrations, or optical errors. It can be an ideal or perfect optical system, having a Strehl ratio of 1.

Figure 2B:
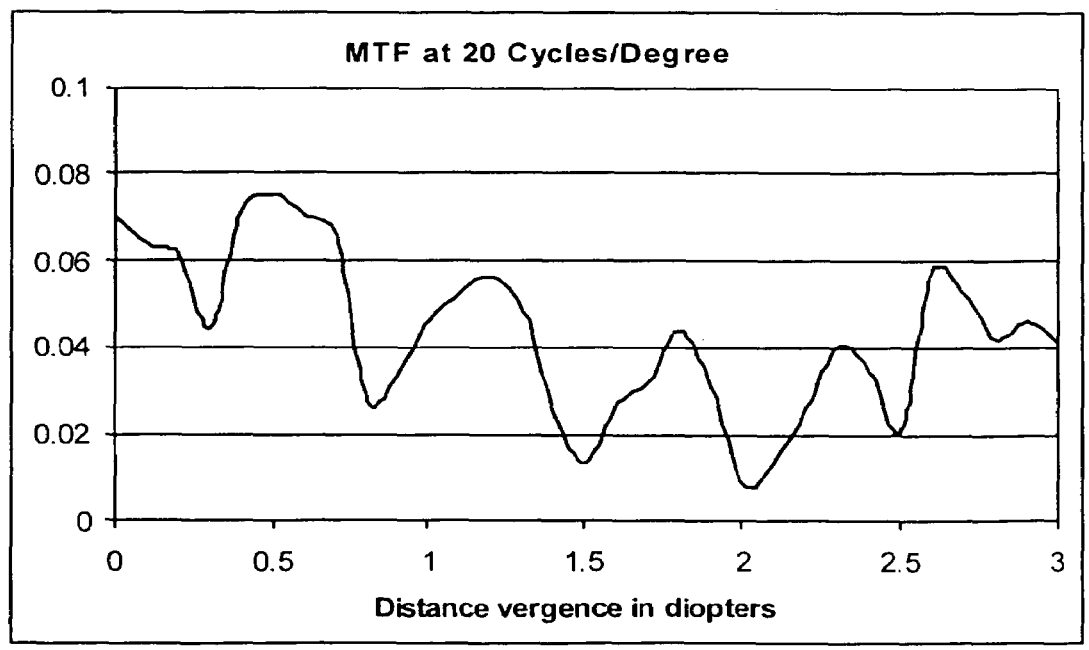

The goal function can also be a function of modulation transfer function (MTF). Modulation transfer function can be used to predict visual performance. Typically, the MTF at one spatial frequency corresponds to one angular extent of targets. The modulation transfer function (MTF) can be calculated with the following formulations:

$$MTF(u,v)=FT[PSF(x,y)]$$

$$MTF(u,v)=Re[GPF(x,y)GPF(x,y)]$$

where u and v represent spatial frequencies, Re represents the real part of a complex number, FT represents a Fourier Transform, GPF represents a generalized pupil function, and x and y represent position or field of view. An example of an MTF is shown in FIG. 2B.

Another example of a goal function, the compound MTF, can be defined as $$F(v)=(\alpha_1 MTF_1+\alpha_2 MTF_2+\alpha_3 MTF_3)/3$$

where $MTF_1$, $MTF_2$, and $MTF_3$ are the MTF values at 10 cycles/degree, 20 cycles/degree and 30 cycles/degree, respectively. These correspond to Snellen eye chart of 20/60, 20/40 and 20/20 visions, respectively. The weighting coefficients $\alpha_1$, $\alpha_2$, $\alpha_3$ can be chosen so that $1/\alpha_1$, $1/\alpha_2$, $1/\alpha_3$ are the diffraction-limited MTF at these spatial frequencies, respectively. Therefore, in the diffraction-limited case, the compound MTF F(v) can have a maximal value of unity.

Where MTF at one spatial frequency corresponds to one angular extent of targets, compound MTF can be defined as linear combination of MTF at different spatial frequencies normalized by a diffraction-limited MTF, and can similarly be used to predict visual outcome. A more general formula for CMTF is $$CMTF(v) = \frac{1}{n}\sum_{i=1}^{n} \alpha_i MTF_i(v)$$

where $\alpha_i$ is the reciprocal of the i-th diffraction-limited MTF. In some cases, three MTF curves at 10, 20 and 30 cycles per degree are used. An ideal value of CMTF can be about 1. Good values can be about 0.2 or about 0.3. In a healthy eye, the spatial frequency limit can be about 60 cycles per degree due to the configuration of retina cones. In the treatment of presbyopia, however, it may not be necessary to provide a treatment corresponding to this limit, as the treatment will often involve a compromise of good distance and near sight. Optionally, a minimum distance vision gauge desired target may be provided, with near sight being optimized and, as needed, compromised.

Figure 2C:
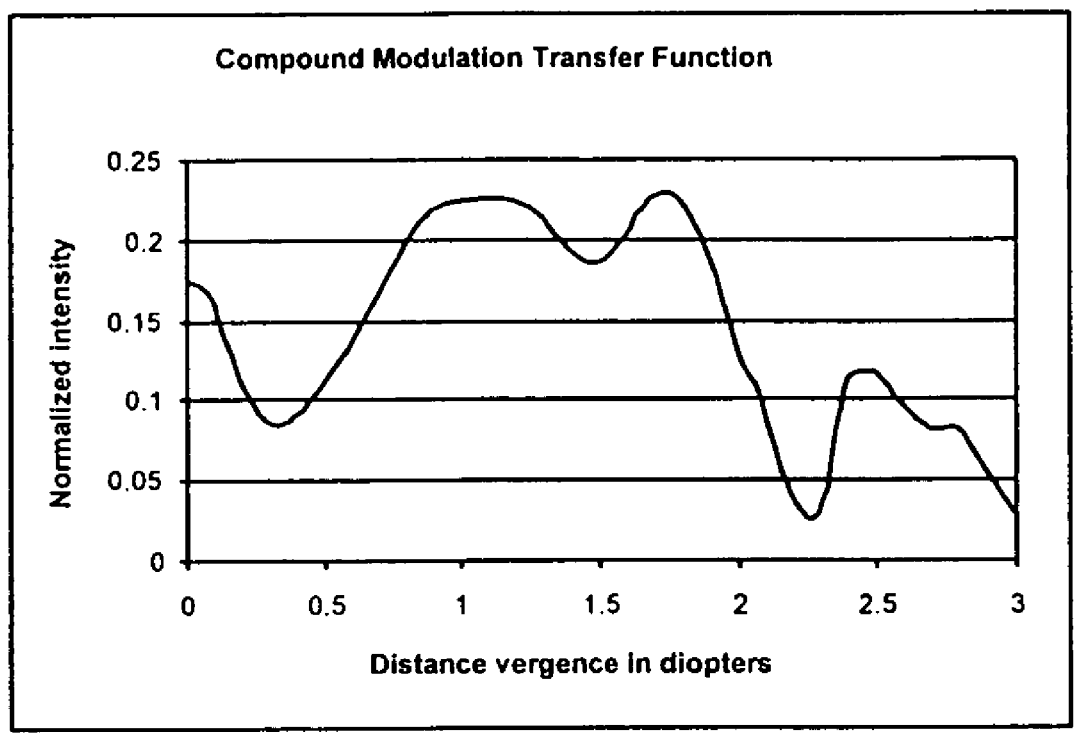
Figure 2C:
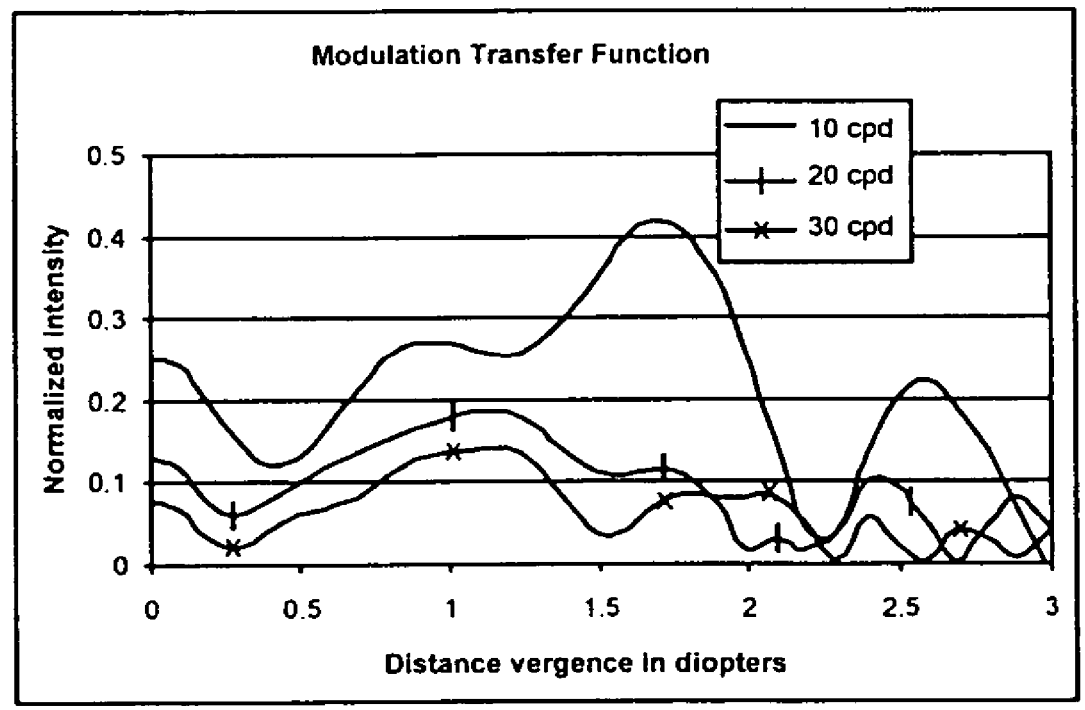

FIG. 2C shows an example of the compound MTF over a vergence of 3 diopters (upper panel) versus its corresponding individual MTF curves at 10, 20, and 30 cpd (cycles per degree). Compound MTF can correlate well with visual acuity and contrast sensitivity at the same time, at least optically.

To establish an optically optimized shape appropriate for presbyopia, at least one of the goal functions, such as Strehl ratio, encircled energy, or MTF, MTF volume or volume under MTF surface (MTFV), compound modulation transfer function (CMTF), or contrast sensitivity (CS) should be maximized. For improved presbyopia treatment, the optical metric can be maximized in all target vergence, that is, for targets at all distances. Furthermore, it is also desirable to minimize the fluctuation of the goal function. Therefore, the goal function, which is incorporated into the optimization algorithm of the optimizer, can be defined as $$O(c_1, c_2, \ldots, PAR) = (1+\sigma)(1+PV)\frac{\int_0^{v_0} dv}{\int_0^{v_0} F(v)dv}$$

where O is the goal function; $c_1, c_2, \ldots$ are the polynomial coefficients; PAR is presbyopia-add to pupil ratio (described below); v is the vergence; F(v) is one of the optical metrics; a is the standard deviation of F(v), PV is the peak-to-valley of F(v); and $v_0$ is the end point of the vergence range, which may be (for example) between 15 and 100 cm, such as 40 cm. Because ∫dv is a constant, either a smaller σ or a larger ∫F(v)dv can minimize the goal function O.

The formulas given here are examples of the many formulae that can be used as the goal function. The basic approach will often be to provide a goal function that is optimized to give as practical a solution as possible for presbyopia correction.

Selecting an Iterative Optimization Algorithm

Any of a number of optimization algorithms may be used by the optimizer to maximize, minimize, or otherwise globally or locally optimize the goal function. Because many numerical algorithms use function minimization concept, it is often convenient, but not necessarily required, to use minimization of the goal function. As examples, N-dimensional minimization algorithms such as the Downhill Simplex method, the Direction Set method, and the Simulated Annealing method can be used to optimize the goal function. Likewise, the algorithm described by Press et al., in "Numerical Recipes in C++", Cambridge University Press, 2002 can also be used. Algorithms such as those listed above are often used for function optimization in multi-dimensional space.

The Downhill Simplex method starts with an initialization of N+1 points or vertices to construct a simplex for an N-dimensional search, and in every attempt tries to reflect, stretch, or shrink the simplex by geometrical transformation so that a close-to-global minimum or pre-defined accuracy can be found. When Gaussian random noise of standard deviation of 0.02 µm in optical path difference (OPD) is added, the algorithm still converges, with no degradation.

In the case of Direction Set method, also known as Powell's method, N one-dimensional vectors are initialized and the N-dimensional search is split in such a way that a one N-dimensional vector is chosen and the minimization is done in that direction while other variables (N−1 dimensions) are fixed. This process is continued until all dimensions are covered. A new iteration is initiated until the pre-determined criterion is met. The Direction Set method can use a separate one-dimensional minimization algorithm such as a Golden section search.

The Simulated Annealing method, which is useful for dealing with a large number of uncertainties, starts with an initial configuration. The objective is to minimize E (analog to energy) given the control parameter T (analog to temperature). Simulated Annealing is analogous to annealing, is a recent, proven method to solve otherwise intractable problems, and may be used to solve the ablation equation in laser ablation problem. This is more fully described in PCT Application No. PCT/US01/08337, filed Mar. 14, 2001, the entire disclosure of which is incorporated herein by reference. Simulated annealing is a method that can be used for minimizing (or maximizing) the parameters of a function. It is particularly suited to problems with very large, poorly behaved function spaces. Simulated annealing can be applied in the same way regardless of how many dimensions are present in the search space. It can be used to optimize any conditions that can be expressed numerically, and it does not require a derivative. It can also provide an accurate overall minimum despite local minima in the search space, for example.

Figure 3:
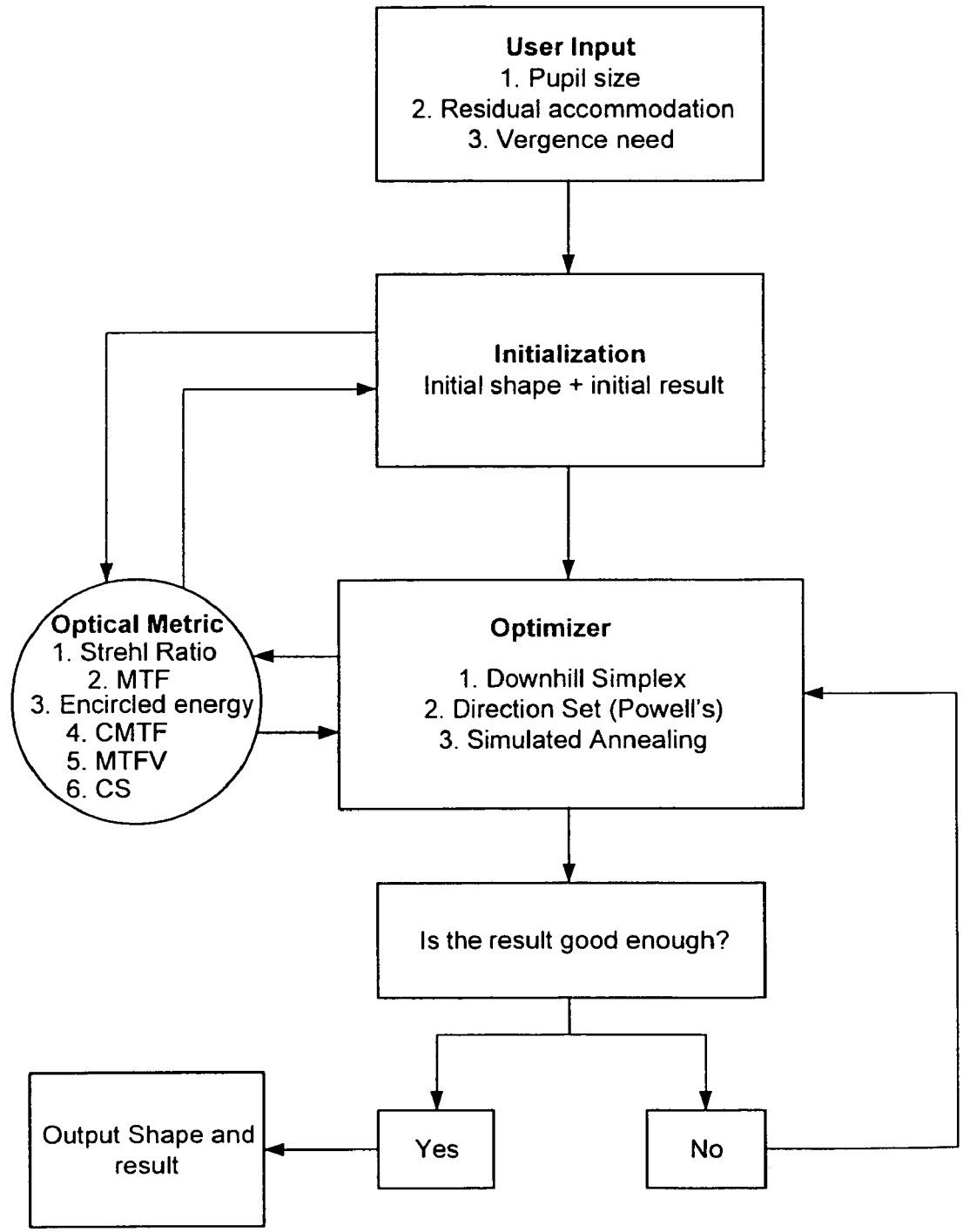
FIG. 3 is a flow chart illustrating exemplary method steps for optimizing a presbyopia-mitigating optical prescription.

FIG. 3 shows the flow chart of an overall method for shape optimization for presbyopia correction. Each functional block may contain one or more alternatives. To create a presbyopia add-on shape W(r), an iterative function minimization algorithm can be employed such that the goal function, which could be a function of any suitable optical metrics (e.g. SR, MTF, EE, CMTF, MTFV, CS) is itself optimized to solve for an unknown shape. The shape can be expanded into a set of even power term polynomials (EPTP) or non-EPTP (i.e. all power term polynomials). EPTP refers to polynomials that only have the even power terms, for instance, $F(r)=ar^2+br^4+cr^6$. The goal function should have good correlation with visual performance, at least optically. Point spread function can be calculated to obtain additional and/or alternative optical metrics. The presbyopia prescription can refer to an optical surface that can be used to treat or mitigate presbyopia. It can correspond to, for example, the shape of a spectacle lens, a contact lens, an intra-ocular lens, a tissue ablation profile for refractive surgery, and the like.

Figure 4:
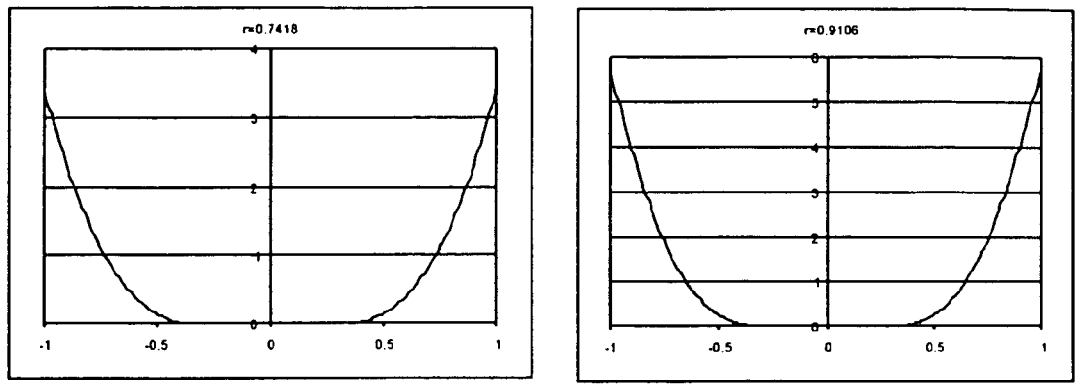
FIG. 4 graphically illustrates two presbyopia-mitigating prescriptions for an eye of a particular patient.

It is desirable that the optimizer provide satisfactory outcome in terms of attributes such as result, convergence, and speed. FIG. 4 shows a comparison of Direction Set method and Downhill Simplex method for the following inputs: pupil size 5.6 mm, vergence 3 D and vergence step 0.1 D. Direction Set method uses 17 iterations and Downhill Simplex method uses 152 iterations. Each Direction Set method iteration takes longer than each Downhill Simplex method iteration. The optimizer value for the Direction Set method is 2.8 while that for the Downhill Simplex method is 2.658. Shape for left panel is as $-0.9055r^2+6.4188r^4-2.6767r^6+0.5625r^8$ with ratio of 0.7418.

Both algorithms seem to converge to a similar shape, although the depths of the shapes are different. Considering the difference in the pupil ratio, however, the actual shapes within 70% of the pupil radius are quite close. When the vergence step is smaller, each iteration can take a longer time, but the overall number of iterations often tends to become smaller.

Inputting an Initial Prescription Into an Optimizer

The initial prescription, often comprising an optical surface shape, may be defined by an expansion such as a polynomial (EPTP, non-EPTP), a Zernike polynomial, a Fourier series, or a discrete shape entirety. A discrete shape entirety can also be referred to as a direct surface representation by numerical grid values. The prescription shape may be assumed to be circularly or radially symmetric, with the aim of approaching an emmetropic eye. The symmetric shape can be decomposed into a set of polynomials, such that it has one or more independent variables. One of the variables can be the presbyopia-add to pupil ratio (PAR), or the ratio of the shape diameter to the pupil diameter. When a central power add region is employed (as described below), the PAR can be the ratio of the radius of the presbyopia-add to the radius of the pupil. It will also be appreciated that the ratios discussed herein can be based on area ratios or on diameter or radius ratios. It should be assumed that when diameter or radius ratios are discussed, that discussion also contemplates area ratios. In certain cases, the PAR can range from about 0.2 to about 1.0. Relatedly, in some cases the methods of the present invention can constrain the PAR to range from about 0.2 to about 1.0. The other variables can be the coefficients of each polynomial term. For example, $$\text{Shape}(r)=ar+br^2+cr^3+dr^4+er^5+fr^6$$

The diameter of the shape can be larger than the pupil size, but if so special considerations may need to be taken. For example, it may be necessary to only consider the net shape within the pupil.

The polynomials can be normal polynomials or polynomials with even power terms only. For example, even-power-term polynomials (EPTP) up to the $6^{th}$ or $8^{th}$ order can be used to obtain a practically good output, that is, a practical optimal shape for the particular patient. Residual accommodation can also play an active role in presbyopia correction. In a related instance, normal presbyopes can be treated with the prescription obtained in this approach together with a prescription for the correction of the refractive error.

As an example, a circularly or radially symmetric, pupil-size dependent shape for presbyopia-add can be assumed for emmetropic presbyopes. The shape can then be expanded to polynomials up to the $6^{th}$ or $8^{th}$ order. With the optimization procedure, it is found that polynomial expansion of the shape up to the $6^{th}$ or $8^{th}$ order can be used to obtain a practical optimal shape for presbyopia correction.

In a wavefront with aberrations, denoted by $W(r, \theta)$, the wavefront can be thought of as an optimal shape for presbyopia correction. The polychromatic PSF can be expressed as $$PSF = \sum_\lambda R(\lambda) \left| FFT\left(P_{sc}(r) \exp\left[-j\frac{2\pi}{\lambda}[W(r,\theta) + \alpha D(\lambda) + V(l) + RA(l)]\right]\right) \right|^2$$

where $R(\lambda)$ is the retina spectral response function and can be approximated to $$R(\lambda) = e^{-300(\lambda - \lambda_0)^2}$$

and $P(r)$ is the pupil apodization function (Stiles-Crawford) and can be written as $$P_{sc}(r) = 10^{-\rho\frac{r^2}{R^2}}$$

and $D(\lambda)$ is chromatic aberration at wavelength $\lambda$ and is close to $$D(\lambda) = -21.587 + 92.87\lambda - 134.98\lambda^2 + 67.407\lambda^3$$

and $V(l)$ is the vergence induced aberration at distance $l$ meters, and $RA(l)$ is the residual accommodation induced aberrations with a different sign as compared to $V(l)$. When there are no aberrations, $RA(l)$ can cancel $V(l)$ as long as there is enough residual accommodation in the eye. Here, the central wavelength $\lambda$ is taken as 0.55 μm (as all wavelength units in the above formulae are in μm). The pupil apodization strength parameter p is taken as 0.06. $\alpha$ is the conversion factor from diopter to optical path difference (OPD). FFT denotes a fast Fourier transform and |*| denotes the module of a complex number.

The polychromatic point spread function, or PPSF, can be the point spread function of an eye as calculated with consideration of the polychromatic nature of the incident light. Further, the chromatic aberrations, the Stiles-Crawford effect, as well as the retinal spectral response function can also be considered.

The vergence induced aberration, or VIA, can be equal to the reciprocal of the vergence distance. When a target at a certain distance is viewed by the eye, it is the same as viewing the target at infinity but the eye has an additional aberration, the vergence induced aberration.

For emmetropic eyes, it may be desirable that the wavefront that is optimized be circularly symmetric. Therefore, it can be decomposed into a set of polynomials (non-EPTP) as $$W(r) = ar + br^2 + cr^3 + dr^4 + er^5 + \ldots$$

However, if it is desirable that the edge of the shape be smoother, it may be advantageous to decompose the wavefront into a set of even-power-term polynomials (EPTP) as $$W(r) = ar^2 + br^4 + cr^6 + dr^8 + \ldots$$

Using even power term polynomials (EPTP) also can help to establish a surface shape that is more round at the center, which creates certain manufacturing or ablation efficiencies.

It may also be useful to denote another parameter, t, to be the ratio of the radius of the wavefront R to the radius of the pupil $R_0$. This is because both $D(\lambda)$ and $V(l)$ can have the same size as the pupil and $W(r)$ usually has a smaller size. When the calculated t is larger than 1, the shape can become larger than the pupil. In this case, only the portion of the shape up to the pupil size is used for optical quality evaluation.

Figure 5A:
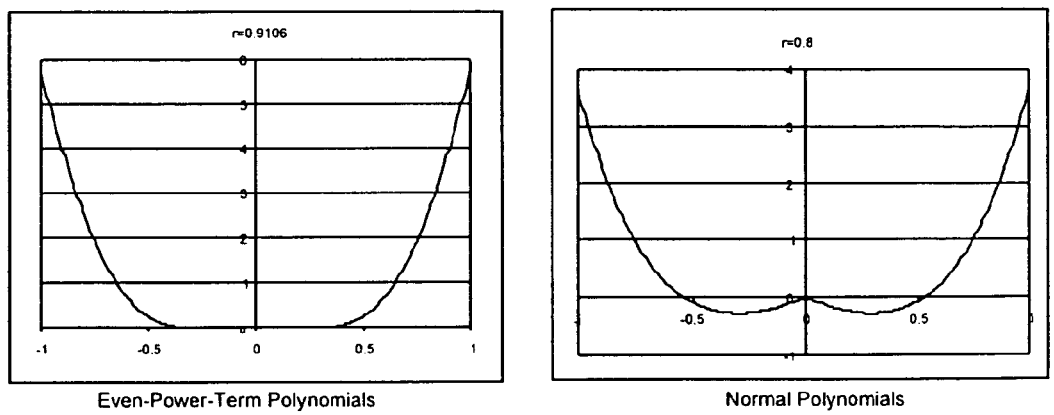
FIGS. 5A and 5B illustrate alternative presbyopia-mitigating prescriptions optimized for an eye of a particular patient, and their characteristics.

As depicted in FIG. 5A, although normal polynomials can give slightly better optimizer values than even-power-term polynomials, the prescription may be harder to realize. FIG. 5A illustrates a comparison of shapes with normal polynomials (left panel) and with even-power-term polynomials (right panel). The shape on the right panel can be expanded as $-1.6154r + 1.7646r^2 + 1.2646r^3 + 1.9232r^4 + 0.1440r^5 + 0.1619r^6$ with a ratio of 0.8 and the shape on the left panel can be expanded as $-1.1003r^2 + 8.2830r^4 + 0.7305r^6 - 2.2140r^8$ with a ratio of 0.9106. Both were determined using Downhill Simplex method for a pupil size of 5.6 mm and vergence of 3 D with 0.1 D step, without residual accommodation. The left panel shows an optimal shape for 6 normal polynomial terms and the right panel shows an optimal shape with 4 EPTP terms. It has been found that polynomials up to the $8^{th}$ power (4 EPTP terms) appear to give highly satisfactory results.

Figure 5B:
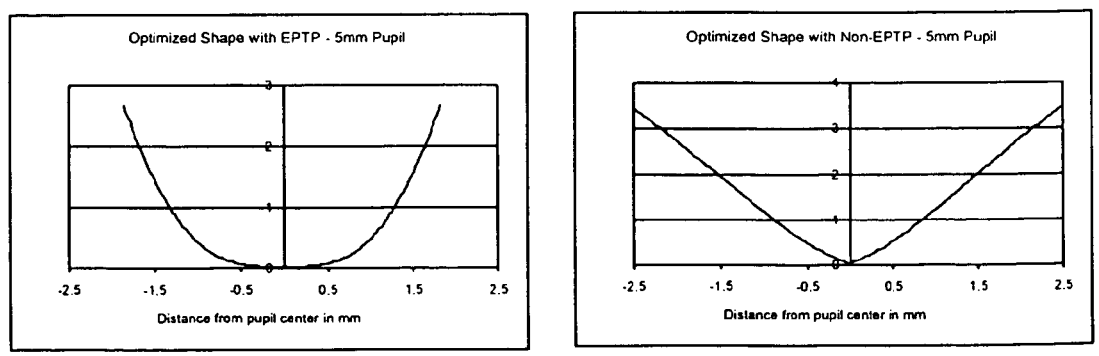

FIG. 5B shows another comparison of EPTP and non-EPTP expansions. The left panel shows an optimized shape based on an 8th order expansion (EPTP), whereas the right panel shows an optimized shape based on a 3rd order expansion (non-EPTP). In general, shapes derived from an EPTP have a smoother shape with a flat central zone. This flat central zone can correspond to good distance visual performance.

Figure 5C:
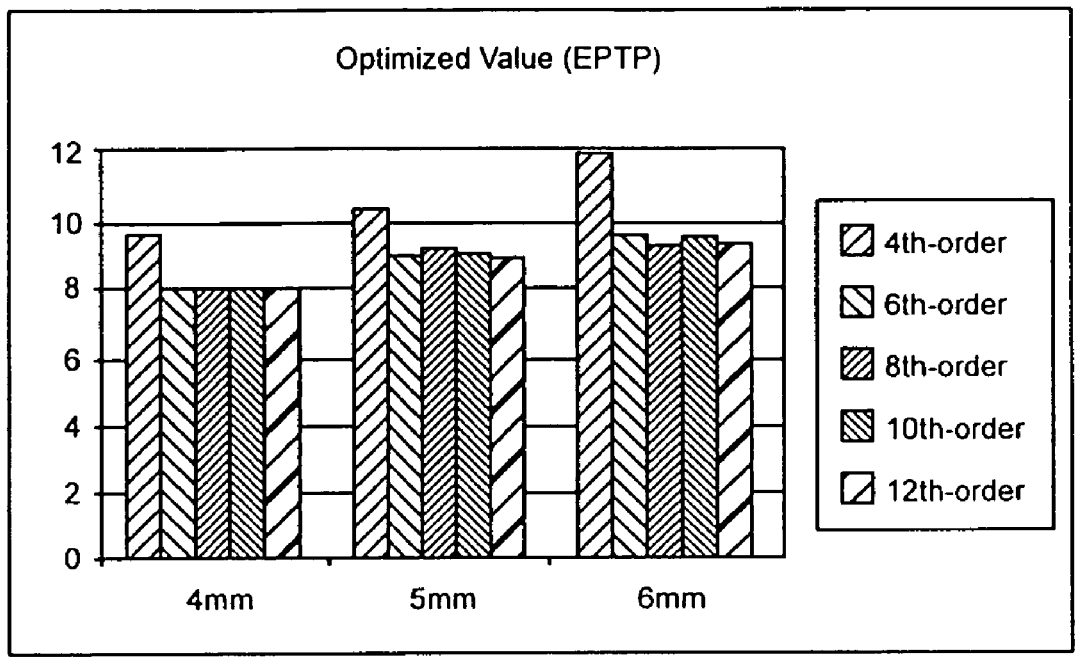
FIG. 5C illustrates a comparison of optimizer values using even-term polynomials and all power term polynomials for pupil sizes of 4 mm, 5 mm, and 6 mm.
Figure 5C:
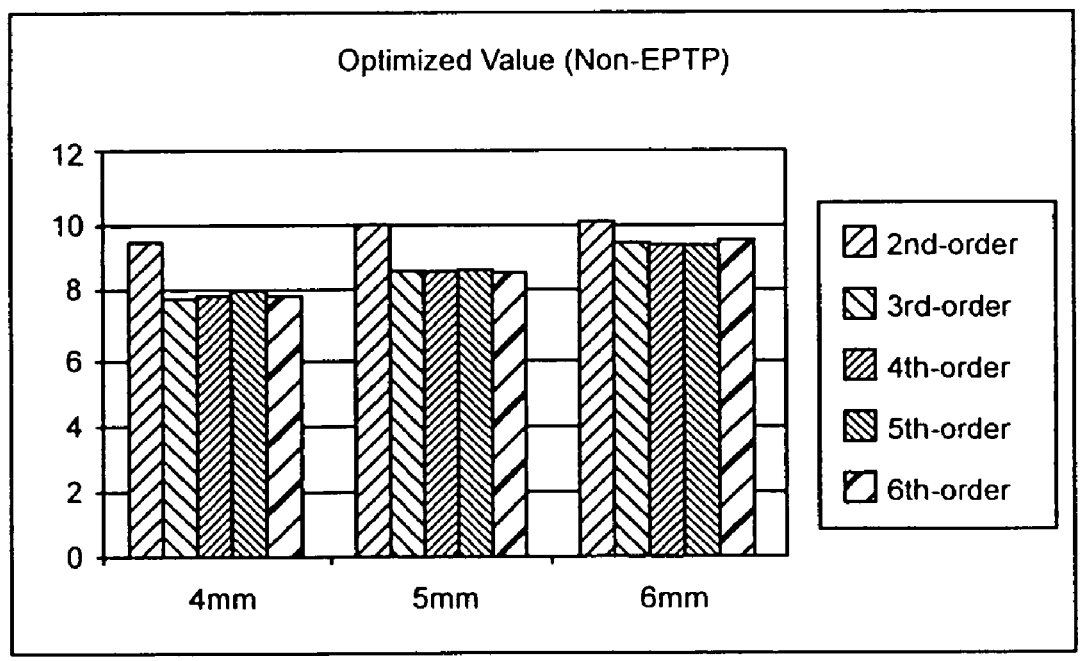

Another comparison of EPTP and non-EPTP expansions is provided in FIG. 5C, which shows optimized (minimized) values with EPTP and non-EPTP expansion for a 4, 5, and 6 mm pupil over a 3 D vergence distance. In general, non-EPTP optimization gives a slightly smaller (more optimized) value than EPTP. Sixth-order EPTP appears to give the smallest value for 4 mm and 5 mm pupils and eighth-order EPTP appears to give the smallest value for a 6 mm pupil. Third-order non-EPTP appears to give the smallest value for 4 mm and 5 mm pupils and fourth-order non-EPTP appears to give the smallest value for a 6 mm pupil.

Using an even-power-term polynomial (EPTP) expansion can result in a smoother shape than a non-EPTP expansion. This smooth shape can be the minimal requirement for good distance vision. In general, $6^{th}$-order or $8^{th}$-order EPTP expansion and $3^{rd}$-order or 4th-order non-EPTP expansion result in good optimized value. Without residual accommodation, larger pupils can be more difficult to optimize than smaller pupils. This is shown, for example, in FIG. 8A.

The optimized multi-focal shape appears to give much more balanced results for the correction of presbyopia than bi-focal and multi-focal shapes.

In addition to using a general polynomial expansion for the optimal surface, it is also possible to use other means of surface expansion. For example, Zernike polynomial expansions may be used. The following formula presents an example of a Zernike polynomial expansion $$W(r) = \sum_{i=1}^{n} c_i Z_i(r, \theta)$$

where radially symmetric terms such as $Z_4$, $Z_{12}$, and $Z_{24}$ can be used, and $c_i$ are free parameters.

Another way of surface expansion is by means of spectral expansion, or Fourier expansion. The following formula presents an example of a Fourier expansion.

$$W(r) = \sum_{i=1}^{n} c_i F_i(r)$$

where $c_i$ are free parameters. Fourier expansion is based on the premise that any surface can be decomposed into a set of sinusoidal harmonics with different spatial frequencies. It may not be necessary to expand the surface to very high spatial frequencies.

Discrete surface, or discrete shape entirety, is another type of expansion that can be used in the present invention. Discrete surface can be represented by the following formula $$W(r) = W_{ij}, (i=1,2, \ldots, M; j=1,2, \ldots, M)$$

where $W_{ij}$ are free parameters (M×M).

Inputting a Set of Patient Parameters Into an Optimizer

The set of patient parameters can also be referred to as the set of user input parameters. The input parameters may provide certain patient characteristics, such as pupil size and its variations, desired power, and residual accommodation which can be modeled by factors such as gender, age, and race, or which can be measured by instruments.

Residual accommodation can be measured in diopters. Vergence can also be measured in diopters and typically is inversely related to distance, such that a distance of infinity corresponds to a vergence of zero. Similarly, a normal reading distance of ⅓ meters can correspond to a vergence of 3 diopters, and a farther distance of 10 meters can correspond to 0.1 diopters.

It can be useful to model the residual accommodation in the optimization process. The visual quality of the shape can be optimized given a certain set of conditions such as vergence, residual accommodation, and chromatic aberrations. However, even without a direct correlation between optical surface and the visual quality, it may be convenient to use the minimum root-mean-squares (RMS) error to determine the accommodation during different visual vergence. For instance, if no aberrations are present, and there is 2 D of residual accommodation, such a patient uses 0.5 D of residual accommodation when visualizing a target at 2 meters. Relatedly, the patient uses all 2 D of residual accommodation to view a target at 0.5 meters. The patient would have difficulty viewing targets closer than 0.5 meters, as the residual accommodation is exhausted and no longer available. People with larger pupils or smaller residual accommodation may be harder to treat.

When aberrations or additional add-on shapes are present, the amount of residual accommodation for different visual vergence may vary. For example, in a patient having 0.5 D residual accommodation, with an add-on shape of exactly 1 D added to the eye, the eye may not need to accommodate until viewing a target at a distance of one meter. Here, the 1 D add-on can cover the first diopter of visual vergence, either entirely or partially. At a large distance, the visual quality may be worse because the eye cannot accommodate in the reverse direction. The techniques of the present invention can be adapted to enhance an optimizer value at low vergence when residual accommodation is assumed.

When a more complicated add-on shape is used, one way to determine the accommodation is to calculate the available residual accommodation which would minimize the overall RMS.

Shape optimization can be customized for a patient. The customization can include the patient's pupil sizes at different lighting and viewing conditions, such as bright far viewing, bright near viewing, dim far viewing, and dim near viewing. The optimization can also be based on the patient's residual accommodation, or predicted residual accommodation based on the patient's age, or the patient's vision preference due to for example, their employment or other requirements. That is to say, the customization can put more emphasis on far, near, or intermediate viewing. Similarly, the customization can put more emphasis on dim lighting condition, bright lighting condition or scotopic lighting condition. Further, the optimization can be based on how long the patient wishes to have the correction last. In many ways, presbyopia correction can be a management of compromise. If a patient needs to have excellent correction, he or she might need re-treatment after a couple of years as he or she gets older, when residual accommodation diminishes and/or the pupil size becomes smaller.

Inputting a Set of Initial Conditions Into an Optimizer

The output result, or optical surface shape, can be sensitive to the choice of the initial condition. In the case of Downhill Simplex method, the initial condition can be the initial N+1 vertices as well as the corresponding initial optimizer values for an N-dimensional problem. In other words, the conditions can be the initial vertices, as well as the value associated with these vertices, for N independent variables. In the case of the Direction Set method, the initial condition can be the initial N direction's unit vector and an initial point for an N-dimensional problem.

Figure 6A:
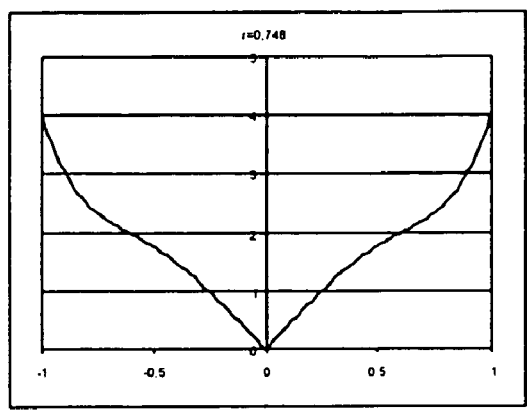
FIGS. 6A-D, show alternative presbyopia-mitigating prescriptions optimized for an eye of a particular patient.
Figure 6B:
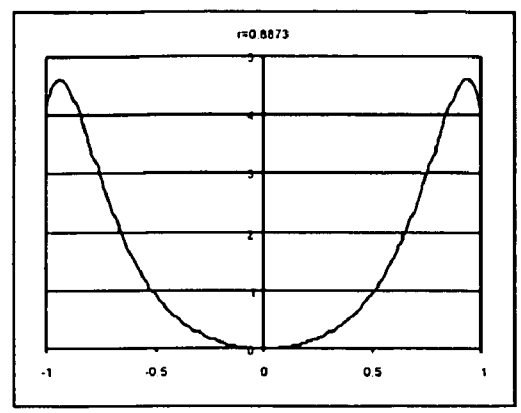
Figure 6C:
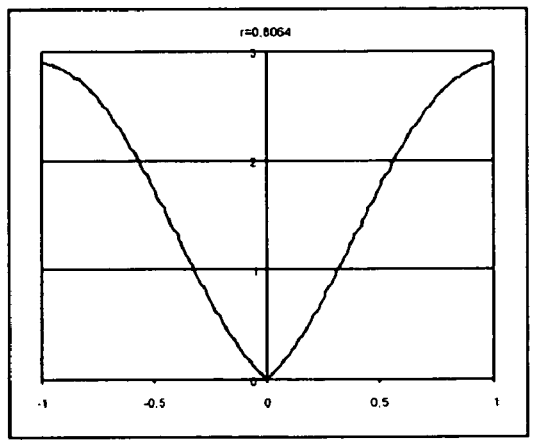
Figure 6D:
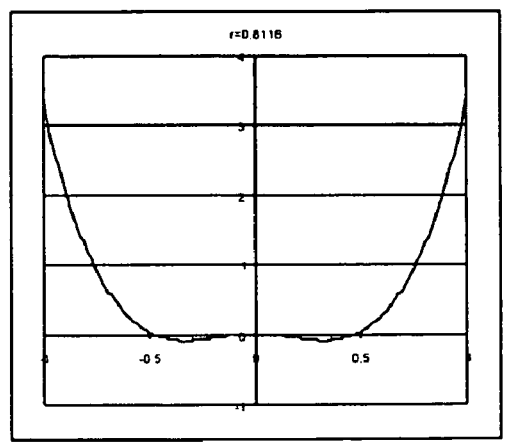

When both or either the initial values for the polynomial coefficients and the pupil ratio are set low, the resulting actual numbers may often be low, especially for the case of pupil ratio. In one example, the initial condition is chosen to be 1.75 for all coefficients and 0.26 for pupil ratio. FIGS. 6A-6D show a variety of shapes determined using different initial conditions, as calculated by the Downhill Simplex method. Pupil size of 5.6 mm and vergence of 3 D with 0.1D step are assumed. Shape for FIG. 6A is $4.12r-0.235r^2+0.08r^3-6.9r^4+4.81r^5+2.157r^6$; for FIG. 6B it is $2.6165r^2+4.1865r^4+6.9123r^6-9.6363r^8$; for FIG. 6C it is $1.7926r+5.0812r^2-2.163r^3-2.3766r^4-1.1226r^5 1.6845r^6$; and for FIG. 6D it is $-1.5178r^2+7.2303r^4-2.4842r^6-1.7458r^8+1.8996r^{10}$.

For the initial conditions, totally random input and fixed ratios may not necessarily help the algorithm to converge to a global minimum or maximum.

Implementing an Optimizer to Establish a Customized Optical Shape for the Particular Patient Per the Goal Function so as to Treat or Mitigate Presbyopia in the Particular Patient The iterative optimization algorithm can be employed to calculate a shape that optimizes the optical quality for the particular patient for distance vision and near vision. In other words, the corrective optical surface shape corresponds to the set of output parameters provided by the optimizer. The output parameters are the coefficients of polynomials describing the shape, as well as the ratio of diameter of the shape to that of the pupil diameter. These output parameters can define the final customized or optimized optical surface shape. This approach provides a numerical way for general optimization of the optical surface shape for presbyopia correction. Whether it is for refractive surgery, contact lens, spectacle lens, or intra-ocular lens, the approach can be very beneficial. For presbyopes with refractive error, the optimal shape can be combined with the shape that corrects for the refractive error, for example the patient's measured wavefront error.

Figure 7:
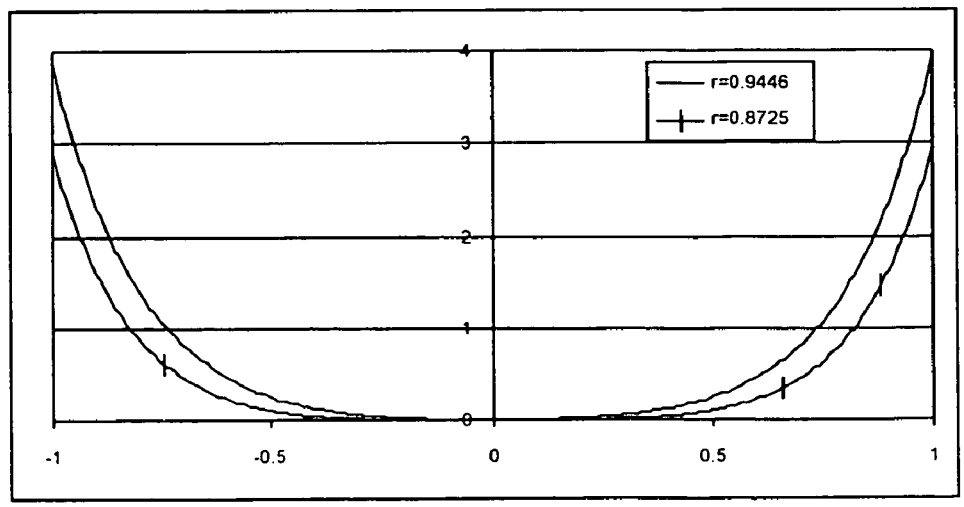
FIG. 7 illustrates effects of random noise on presbyopia-mitigating prescriptions optimized for an eye of a particular patient.

In order to model such deviation in practice, Gaussian distributed noise can be added into the shape so that when noise is present the stability of the algorithm can be tested. For example, Gaussian noise of standard deviation of 0.02 μm OPD can be introduced. This corresponds to nearly 0.06 μm in tissue depth in the case of laser surgery. This is larger than the general RMS threshold for the Variable Spot Scanning (VSS) algorithm for such a shape. FIG. 7 illustrates a comparison of the shapes calculated with a noise-free (dark) condition and with a 0.02 μm standard deviation of Gaussian random noise in OPD on the wavefront. The noise-free case has an optimizer value of 3.008 with 184 iterations and the noisy case has an optimizer value of 2.9449 with 5000 iterations. Both use Downhill simplex method. Pupil size is 5 mm with 3 D vergence and 0.1 D step. Noise addition can also help to guarantee the stability of the algorithm.

It is also possible to test how the convergence, optimizer value, and shape work with different input pupil sizes. An example of results from such a test is shown in Table 1. For smaller pupil sizes, the shape can cover the whole pupil. That is to say, the shape can be larger than the pupil size. Also, the depth may tend to become smaller with smaller pupils.

As determined by the approach of the present invention, one desirable optical surface shape has a central un-ablated zone and an outside zone that provides improved near vision or reading capability. Based on the example shown in FIG. 4, the central flat zone can be about 1.96 mm in diameter. Because the healing effect may reduce the central zone, the planned flat ablation may need to go beyond 2 mm in order to get a healed flat zone of about 1.96 mm. This can be for a pupil size of about 5.6 mm (natural size). The present invention can also consider practical pupil dependency in the approach. In one example of the present invention, the optical zone can go to about 0.91 times the size of the pupil size, which is about 5.1 mm. Further, the present invention may also incorporate a transition zone such as the VISX standard transition zone technique, as used in variable spot scanning (VSS). What is more, the present invention can also provide a clear mathematical description for the optical surface shape outside of the un-ablated zone.

Figure 8A:
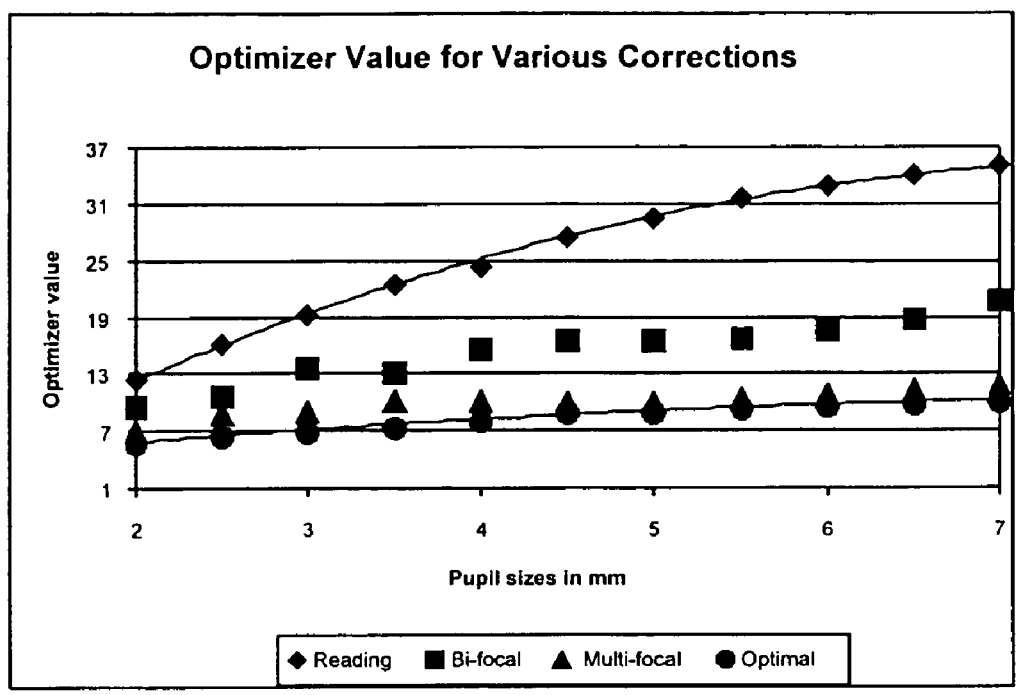
FIGS. 8A-C, compares presbyopia-mitigating optimized prescriptions to alternative treatments for differing pupil sizes.
Figure 8B:
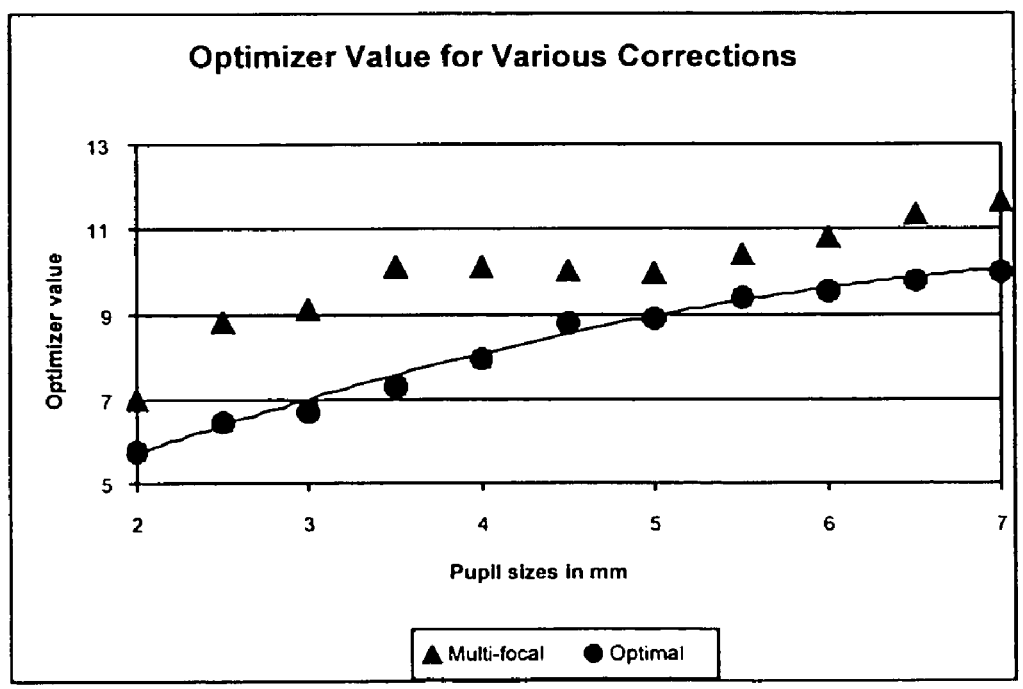
Figure 8C:
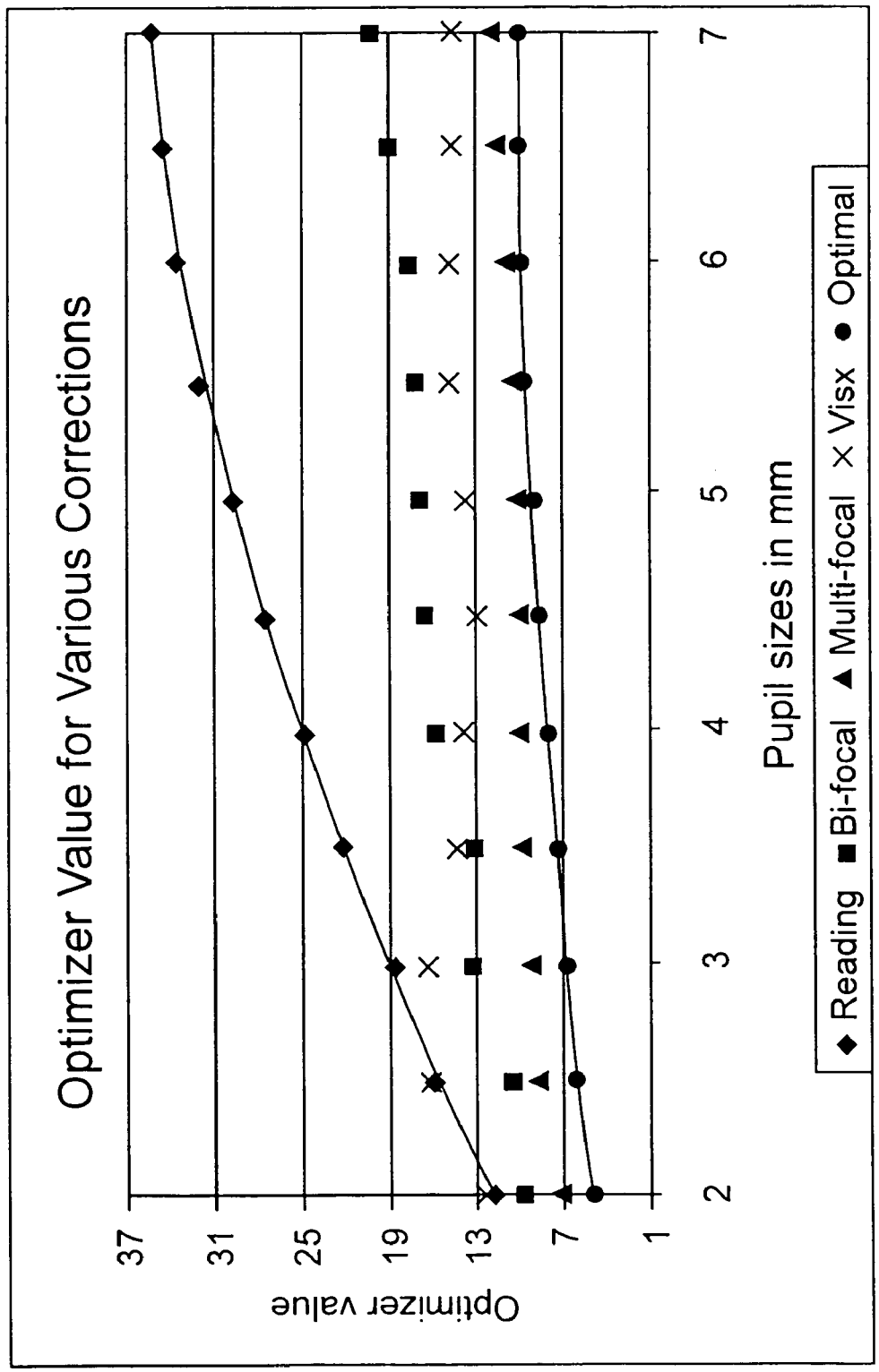

Relatedly, FIG. 8C illustrates that there can be a dependency between optimizer value and pupil size. FIG. 8C also shows a preferred optimizer value (optimal). An optimizer value can be a value of the goal function after it is optimized. Theoretically, this value should not be smaller than unity. An optimization, or minimization, algorithm can be used to find values of free parameters such that the optimizer value is as close to unity as possible.

The present invention can incorporate varying pupil sizes, although presbyopes may tend to have smaller pupil size variation. Because an optimal shape for a fixed pupil size may no longer be optimized if the pupil size changes, the present invention can provide approaches that can allow for pupil size variations. The final optical surface shape can be one that gives an optimal optical quality over a certain vergence range when the pupil size varies over a range.

To demonstrate how effective a solution is in terms of optical metrics, the MTF can be shown at different spatial frequencies, as illustrated in FIGS. 8A-C, which provides optimizer values for various corrections. Apparently the optimal curve gives the minimum (optimized) value for all pupil sizes. Eyes with larger pupils can be more difficult to optimize. What is more, carefully designed multi-focal correction can be close to optimal, as further illustrated in FIGS. 8A-C. That is, the optimizer value for the multi-focal correction can be close to that of the optimized correction, hence the results are quite similar. This outcome is also

TABLE 1

Shapes for pupil dependency with 3D vergence and 0.1D step.

Figure 10:
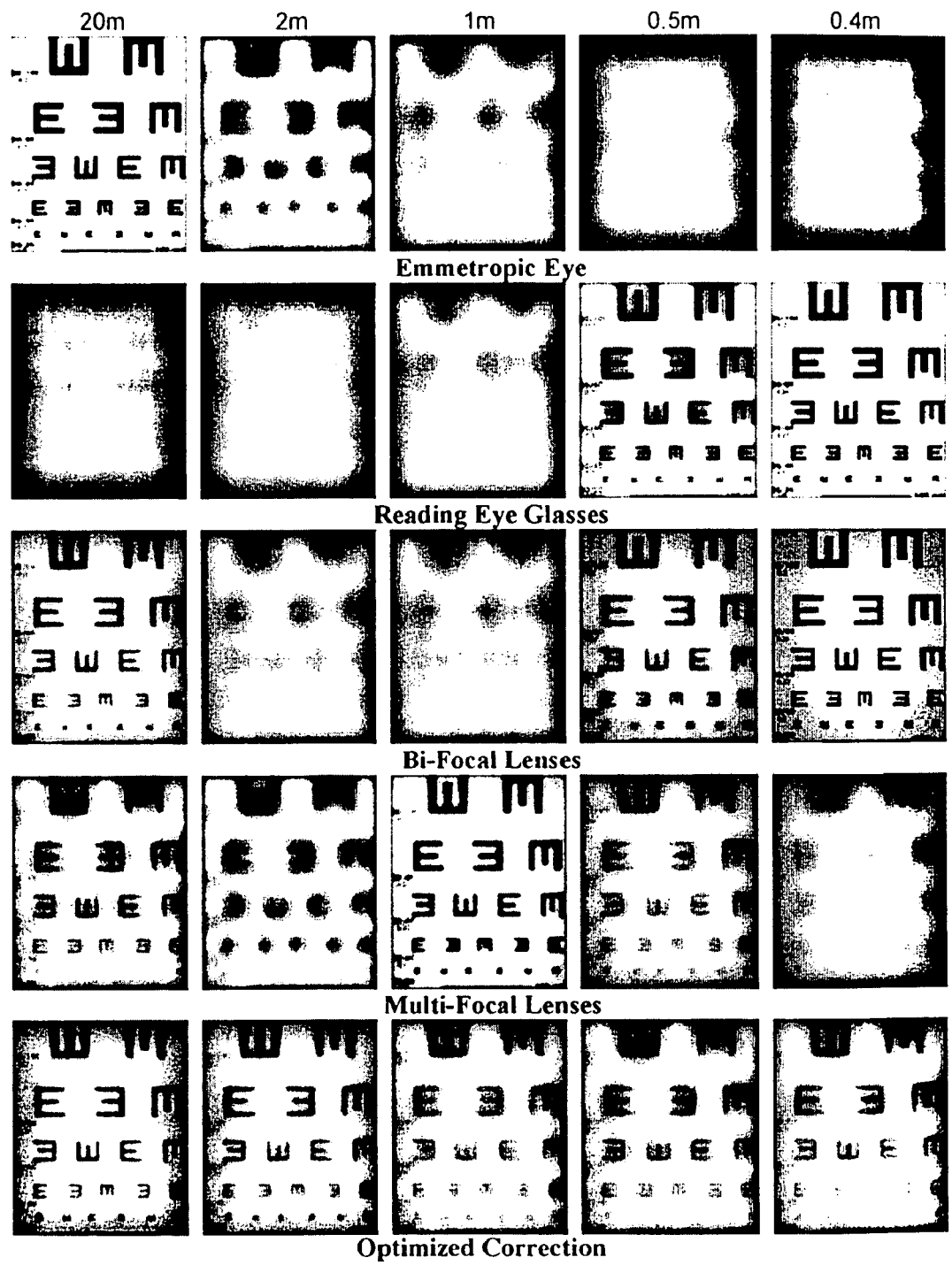
FIG. 10 illustrates simulated viewing charts viewed at differing distances to compare presbyopia-mitigating optimized prescriptions to alternative treatments.

| Pupil | # Iterations | A | B | C | D | T | Value | Depth |
|---|---|---|---|---|---|---|---|---|
| 6.0 | 234 | −1.5688 | 12.0893 | −0.5895 | −2.6934 | 0.9866 | 2.6808 | 7.2881 |
| 5.8 | 316 | −0.5212 | 4.4186 | −0.8472 | −0.0764 | 0.6870 | 2.8215 | 2.9980 |
| 5.6 | 152 | −1.1003 | 8.2830 | 0.7305 | −2.2140 | 0.9106 | 2.6580 | 5.7356 |
| 5.4 | 274 | −0.5918 | 5.0881 | 1.2448 | −1.1930 | 0.9124 | 2.7539 | 4.5651 |
| 5.2 | 269 | −1.4101 | 5.3067 | −0.4326 | −0.4379 | 0.7944 | 2.7979 | 3.1210 |
| 5.0 | 186 | 0.4079 | 2.2298 | 0.0598 | 1.1958 | 0.9446 | 3.0080 | 3.8933 |
| 4.8 | 531 | −3.4870 | 54.9625 | 48.5083 | −125.31 | 1.8427 | 2.6772 | 4.0692 |
| 4.6 | 492 | −1.3517 | 8.5336 | −4.8138 | 1.6981 | 0.999 | 2.5871 | 4.1223 |
| 4.4 | 422 | −2.1972 | 17.2673 | 32.1306 | −44.903 | 1.5095 | 2.6924 | 3.4652 |
| 4.2 | 163 | −0.8345 | 4.2663 | 4.3575 | −3.5136 | 1.1093 | 2.7196 | 2.9770 |
| 4.0 | 545 | −4.8205 | 29.1525 | 7.9952 | −23.086 | 1.5984 | 2.6822 | 2.7003 |
| 3.8 | 333 | 0.1519 | 0.6105 | 2.5097 | −1.6318 | 0.7765 | 3.0533 | 1.6403 |
| 3.6 | 177 | −1.0422 | 1.4185 | 2.2061 | −0.9600 | 0.9736 | 2.7533 | 1.7636 |
| 3.4 | 230 | −3.6844 | 19.0878 | 4.2289 | 5.3957 | 1.6909 | 2.7202 | 1.4760 |
| 3.2 | 219 | −1.2266 | 1.9391 | 0.8145 | 0.2914 | 1.0989 | 3.0486 | 1.0858 |
| 3.0 | 287 | 3.3482 | −2.5793 | 0.8977 | −0.3937 | 0.9941 | 2.9061 | 1.3286 |
| 2.8 | 257 | −0.2052 | 0.2657 | 0.0451 | 0.2494 | 0.7920 | 2.8933 | 0.3890 |
| 2.6 | 136 | −0.6749 | 1.8074 | 0.3418 | −0.3918 | 1.0637 | 2.7377 | 0.8731 |
| 2.4 | 332 | −2.8455 | 16.408 | −13.119 | 0.9270 | 1.5988 | 3.0920 | 0.7653 |
| 2.2 | 239 | −2.6435 | 2.2329 | 1.9556 | −1.7776 | 0.8557 | 3.1667 | 0.6329 |
| 2.0 | 303 | −0.6398 | 0.9010 | 0.5835 | −0.3601 | 0.9527 | 3.9384 | 0.5827 | illustrated in FIG. 10. The lower regression line in FIG. 8C can set the practical limit for the optimizer value.

Figure 9A:
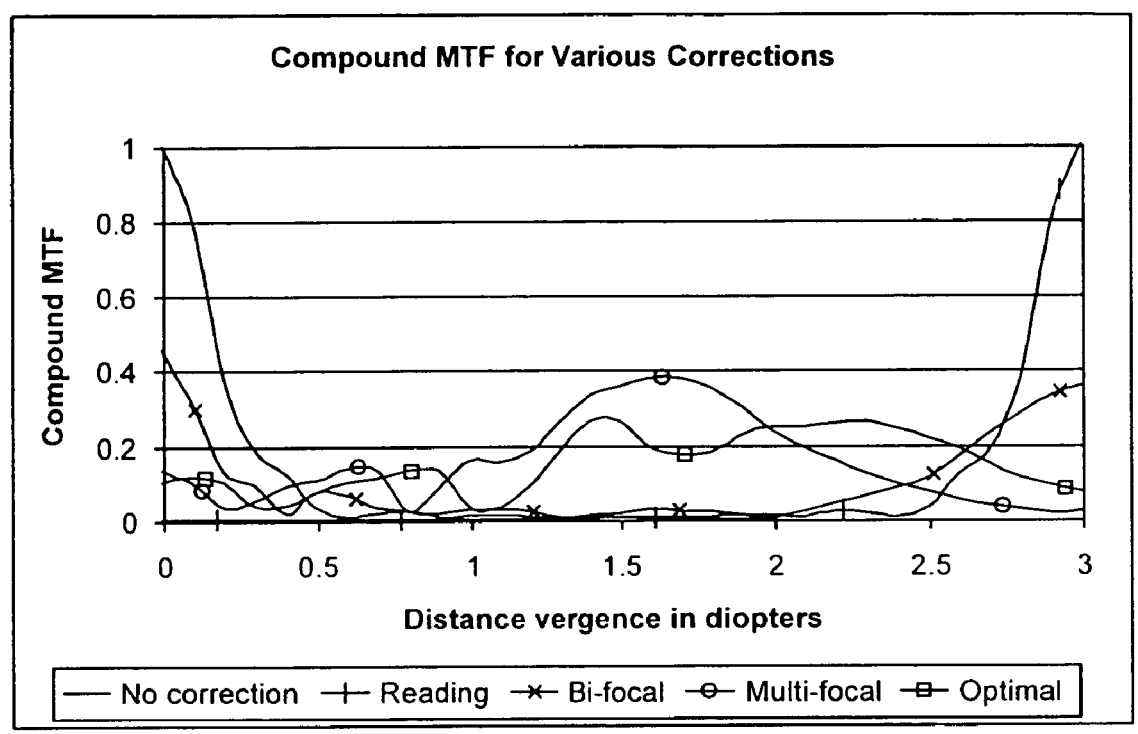
FIGS. 9A-C, compares presbyopia-mitigating optimized prescriptions to alternative treatments for a range of viewing distances.
Figure 9B:
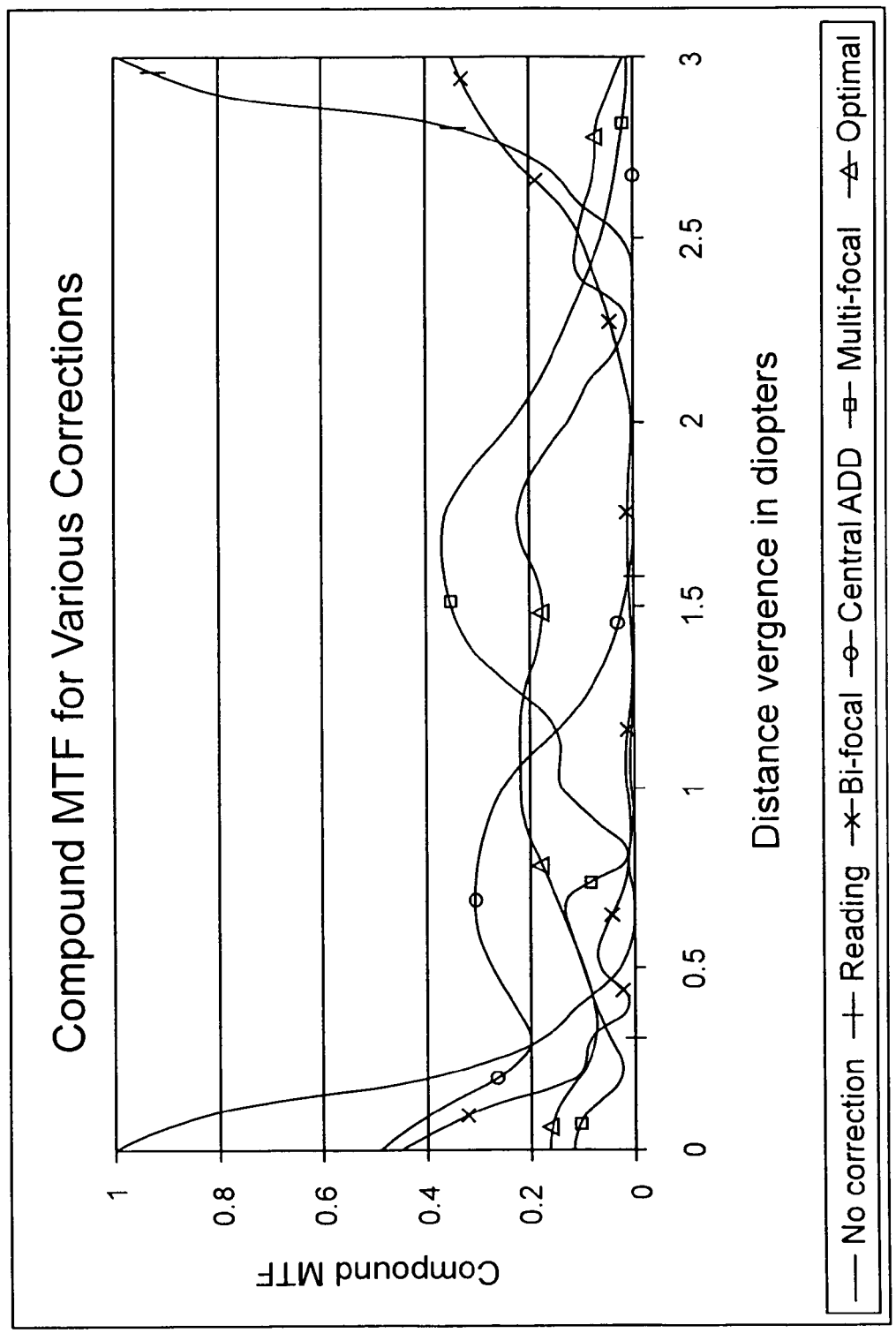
Figure 9C:
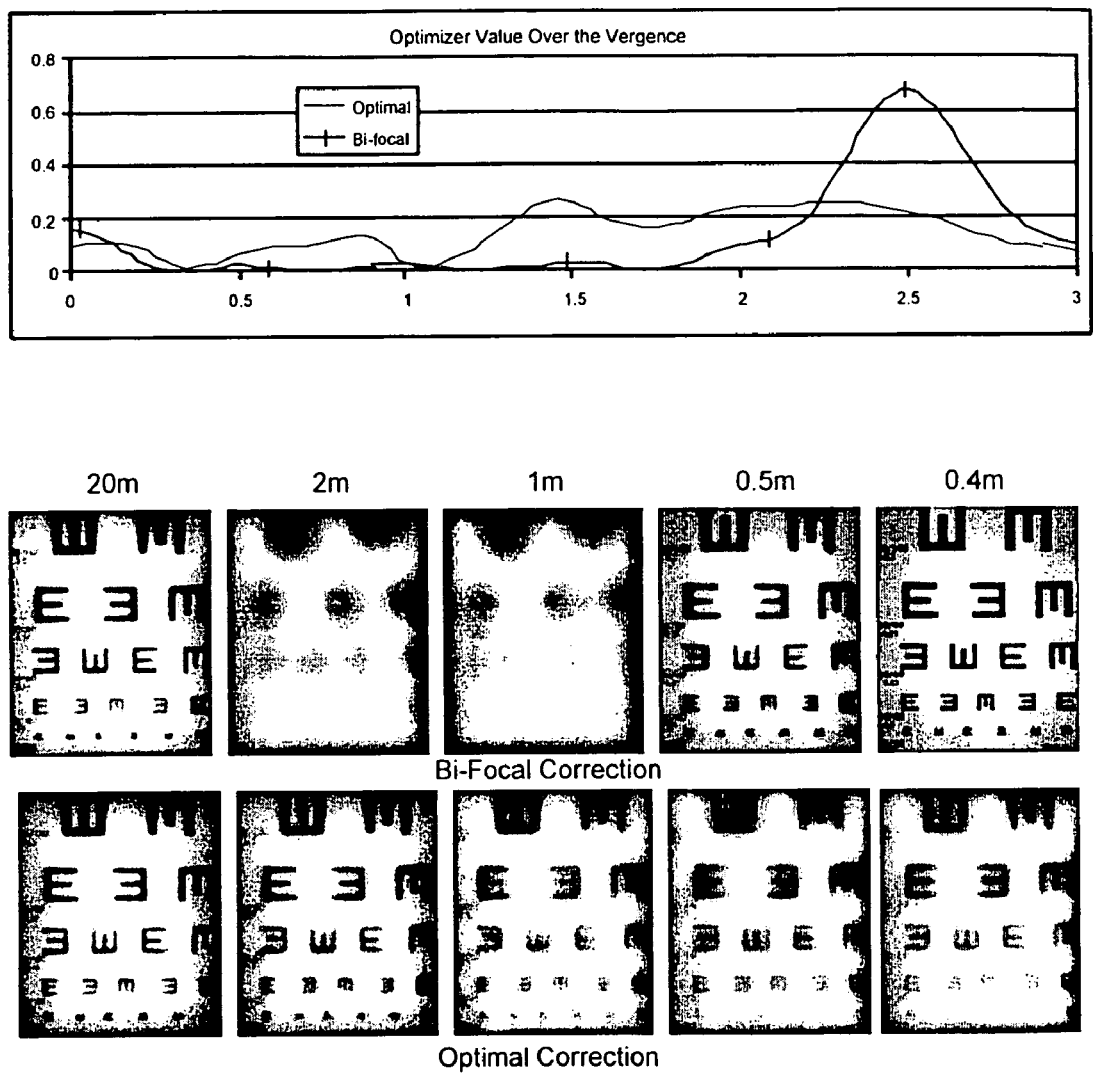

In another approach, to demonstrate how effective a solution is in terms of optical metrics, the compound MTF can be plotted, as shown in FIGS. 9A-B. Here, the compound MTF for various treatments for a 5 mm pupil over a 3 D vergence is plotted. It can be beneficial to optimally balance the level of compound MTF at every vergence distance or over the desired vergence. FIG. 9C shows a comparison of bi-focal and optimal corrections, with a simulated eye chart seen at different target distances, assuming a 5 mm pupil with no accommodation. The eye chart has 2/100, 20/80, 20/60, 20/40, and 20/20 lines, respectively.

FIG. 10 is a simulated eye chart seen at different target distances, and compares an optimized case (bottom) to no correction (top line); reading glasses (second line); bi-focal lenses (inner half for reading and outer half for distance, third line); and multi-focal lenses (pupil center for reading with maximum power and pupil periphery for distance with zero power and linear power change in between, four line). The effects of the optimization can be clearly seen by the comparison. No accommodation or refractive error is assumed in any of the cases. The eye chart has 20/100, 20/80, 20/60, 20/40, and 20/20 lines.

Using the above approaches, it is possible to obtain a shape that is not only larger than the pupil size, but that can also be practically implemented. Often, only the portion of the shape inside the pupil may be evaluated for optical quality, although this is not a requirement. For example, the entire zone over the pupil can remain un-ablated, but there may be a zone outside the pupil that is ablated. In this way, distance vision is not affected, but for near vision, there can be an advantage from light coming outside of the pupil due to greatly deformed periphery. A goal function based on geometrical optics, or ray tracing, can be useful to determine such shapes.

Residual accommodation can also affect the optimization result, because it can remove some of the ripples on the combined wavefront at any vergence.

The approaches of the present invention can be implemented on a variety of computer systems, including those with a 200 MHz CPU with 64 MB memory, and typically will be coded in a computer language such as C or C++. Simulations have successfully been run on a laptop computer with a 1.2 GHz CPU with 256 MB memory. The techniques of the present invention can also be implemented on faster and more robust computer systems.

Figure 11:
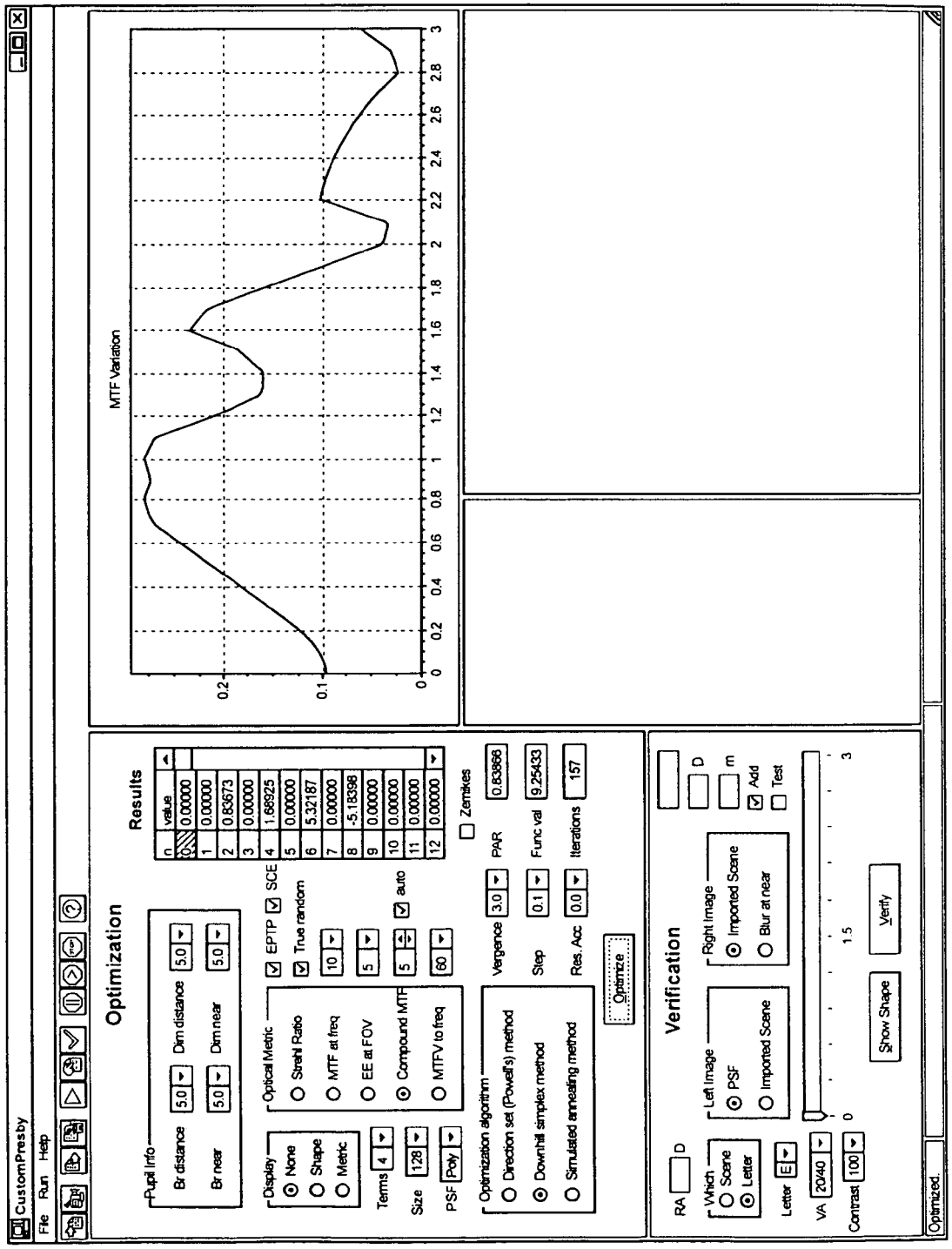
FIGS. 11-13 illustrate graphical interface computer screen displays for a prescription optimizer and system.
Figure 12:
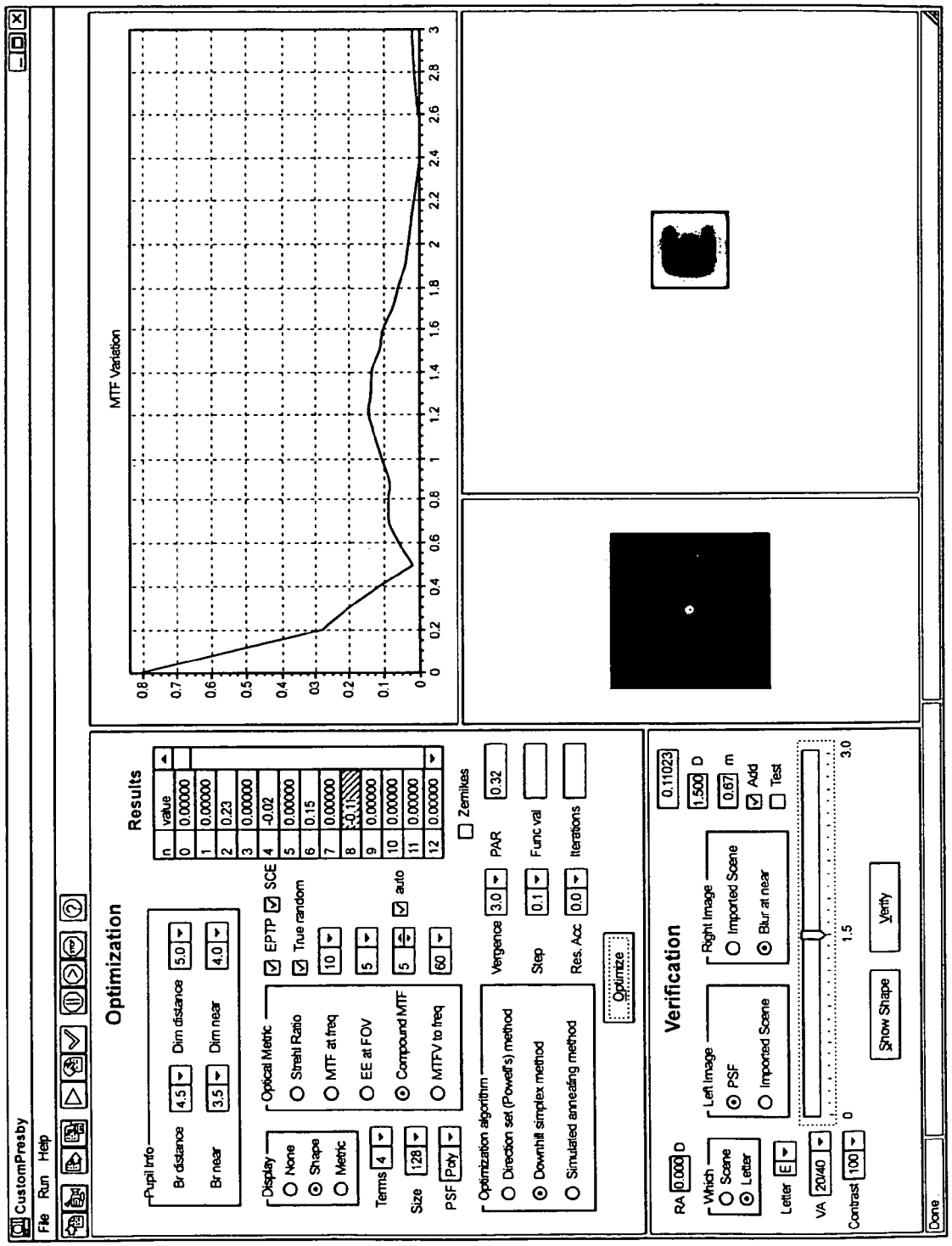
Figure 13:
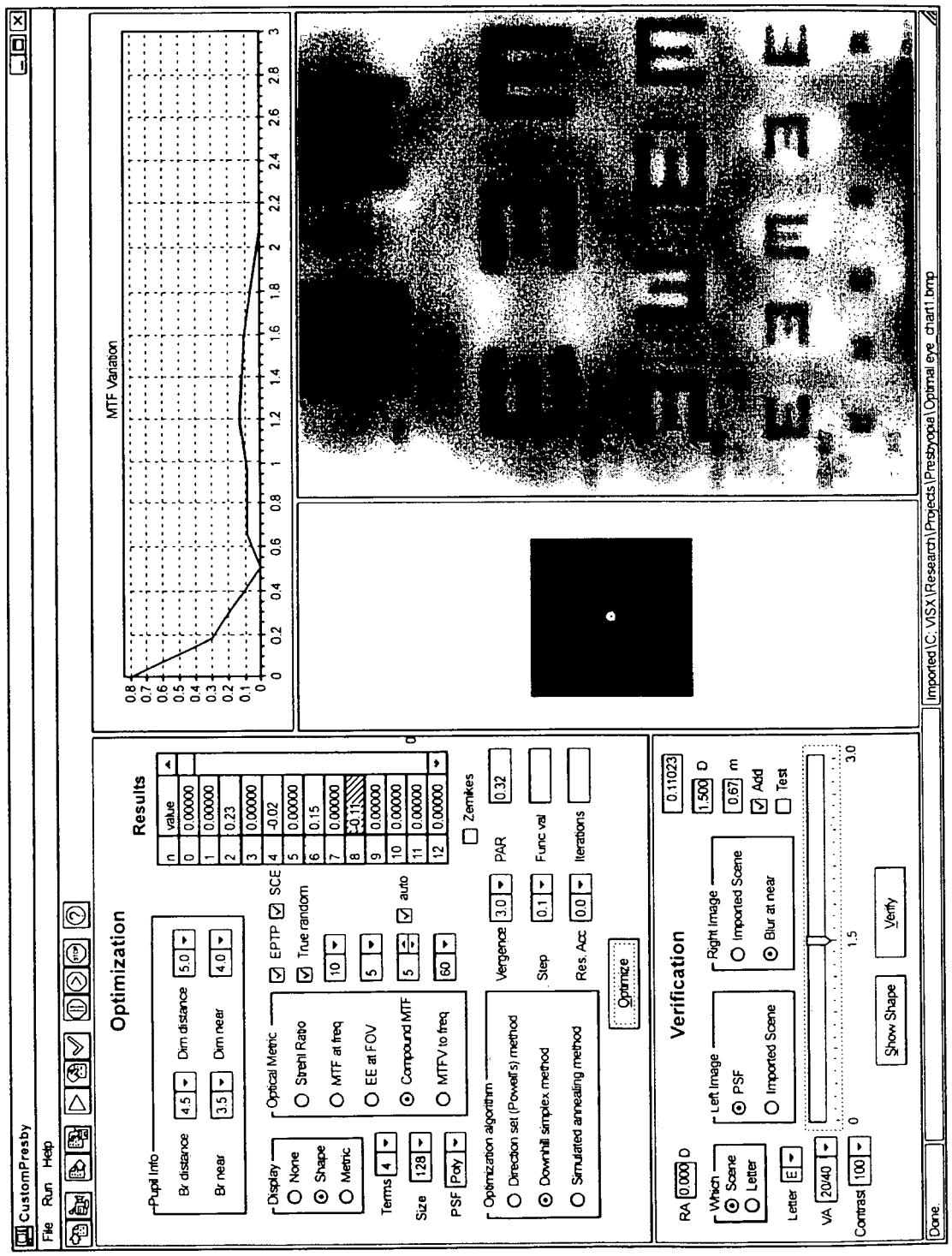

The present invention includes software that implements the optimizer for practical applications in a clinical setting. The optimizer will often comprise an optimizer program code embodied in a machine-readable medium, and may optionally comprise a software module, and/or a combination of software and hardware. As shown in FIGS. 11-13, the software interface can comprise two primary panels: the parameter panel and the display panel. The parameter panel can be split into two sub-panels: optimization and verification. The display panel can also be split into two sub-panels: graph panel and image panel. The software can also include a menu bar, a tool bar, and a status bar. In the tool bar, small icons can be used for easy access of actions.

The optimization sub-panel can include a number of parameter units. For example, a first parameter unit can be the pupil information group. In the examples shown in FIGS. 11-13, the user or operator can give four different pupil sizes for a specific eye. More particularly, the pupil information group includes the pupil size in (a) bright distance viewing condition, (b) bright near viewing condition (e.g. reading), (c) dim light distance viewing condition, and (d) dim light near viewing condition (e.g. reading). These different pupil sizes can be used in the optimization process.

A second parameter unit in the optimization sub-panel can be the display group. In the examples shown in FIGS. 11-13, the user or operator has three different choices for the display, including (a) none, (b) shape, and (c) metric. The display group can provide instruction to the software regarding what kind of display is desired for each iteration. For instance, none can mean no display, shape can mean displaying the current shape, and metric can mean displaying the current optical metric curve over the desired vergence for this current shape. The choices can be changed during the optimization procedure, and in this sense it is interactive.

A third parameter unit in the optimization sub-panel can be the optical metric group. In the examples shown in FIGS. 11-13, the user has five different choices for the metric, including (a) Strehl ratio, (b) MTF at a desired spatial frequency, (c) encircled energy at a desired field of view, (d) compound MTF (CMTF) with a set of specific combinations, which could be any number of MTF curves at different spatial frequencies, and when the "auto" check box is checked, it can use a default CMTF with three frequencies, such as, for example: 10, 20 and 30 cycles/degree, and (e) the MTF volume up to a specific spatial frequency. 25% CMTF over the vergence appears to be an example of a good target value for optimization.

A fourth parameter unit in the optimization sub-panel can be the optimization algorithm group. In the examples shown in FIGS. 11-13, the user has three different choices for the optimization algorithm employed by the optimizer, including (a) the Direction Set (Powell's) method, (b) the Downhill Simplex method, and (c) the Simulated Annealing method. The optimizer can employ a standard or derived algorithm for function optimization (minimization or maximization). It can be a multi-dimensional, non-linear, and iterative algorithm.

A number of other parameters can be included in the optimization sub-panel. As shown in FIGS. 11-13, these other parameters can be implemented separately (optionally as a ComboBox) with a number of choices for each. These can include parameters such as (a) the number of terms of the polynomial expansion, (b) the frame size, (c) the PSF type (monochromatic, RGB, or polychromatic), (d) whether the shape is EPTP or non-EPTP, (e) the vergence requirement, (f) the vergence step, and (g) the residual accommodation. The software can include a StringGrid table that displays the polynomial coefficients, the PAR value, the optimizer value, as well as the current number of iterations. These numbers can be updated every iteration.

The verification sub-panel can include a number of parameter units. For example, a first parameter unit can be the "which" group. In the examples shown in FIGS. 11-13, the operator can use this group to select whether to use built-in eye chart letters, or an entire eye chart or a scene. A second parameter unit in the verification sub-panel can be the left image group. The user can make a selection in the left image group from PSF and imported scene. A third parameter unit is the right image group, wherein the user can make a selection from imported scene, and blur at near. The two image display groups are for the left and right subpanels in the image subpanel.

As further illustrated in FIGS. 11-13, the ComboBox for letter can provide a list of different eye chart letters, and the VA ComboBox can provide the expected visual acuity, from 20/12 to 20/250. The Contrast ComboBox can provide a list of contrast sensitivity selections, from 100% to 1%. Two check box can also be included. The Add check box, once checked, adds the presbyopia to the simulated eye. The Test check box, when checked, performs the distance (zero vergence). At the bottom, there is a slider with which all the saved images (e.g.) PSF and convolved images can be reviewed.

Figure 14:
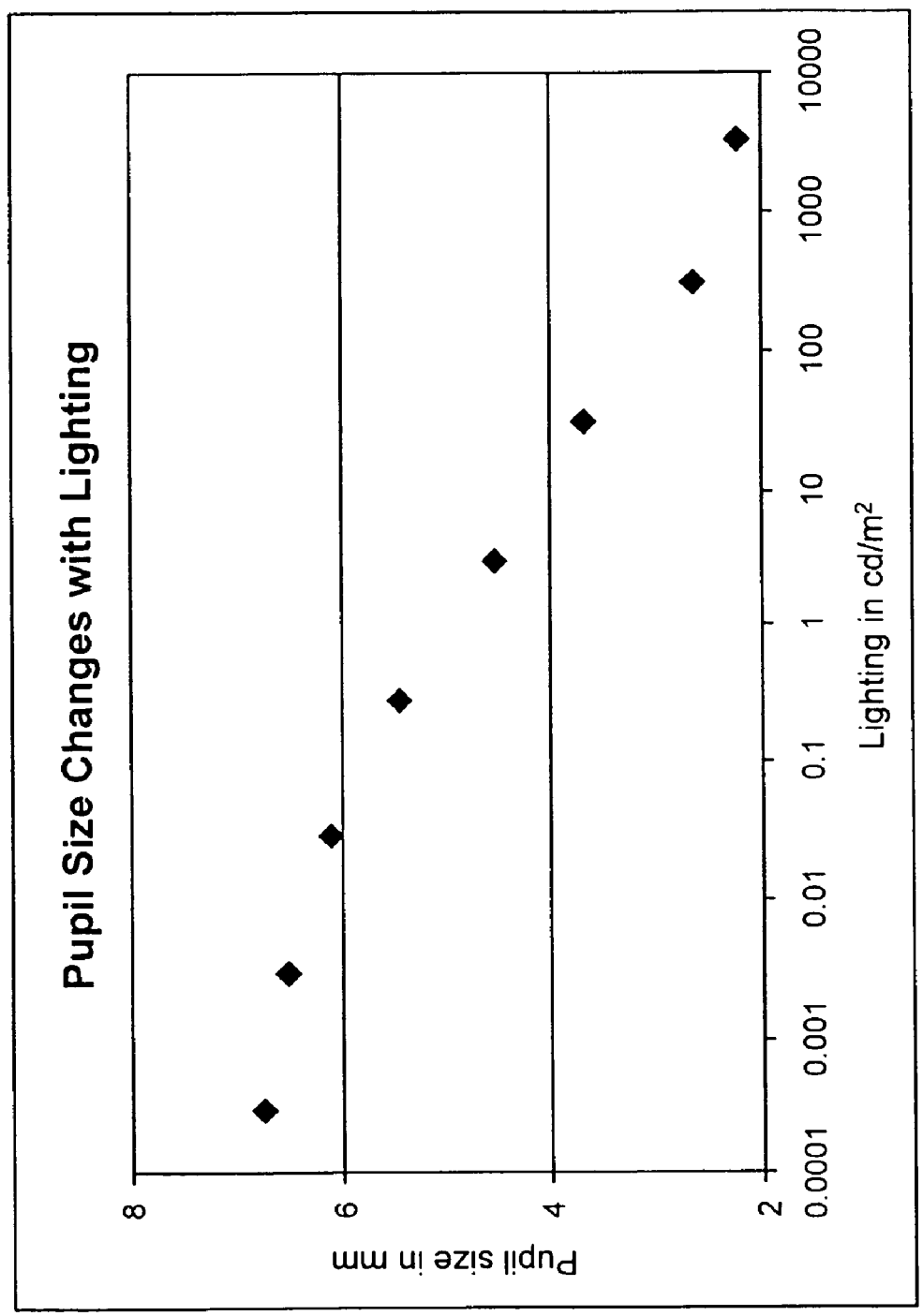
FIGS. 14 and 15 illustrate pupil sizes and changes at differing viewing conditions for a particular patient.

There are many factors that can affect the pupil size, and these factors can be considered optimization approaches of the present invention. For example, the shape can be customized for various lighting and accommodation conditions. As shown in FIG. 14, and further discussed in Table 2, pupil size can change with lighting conditions. Each of the presbyopia-mitigating and/or treating methods, devices, and systems described herein may take advantage of these variations in pupil size. A pupil size of a particular patient will often be measured, and multiple pupil sizes under different viewing conditions may be input for these techniques.

TABLE 2

|  | dim | bright |
|---|---|---|
| distance | 5 mm | 3.5 mm |
| near | 4 mm | 2.5 mm |

A patient can also have a task-related vision preference that correlates with lighting conditions, such as those described in Table 3, and the customization can be based upon these task-related preferences.

TABLE 3

| cd/m² | lighting condition |
|---|---|
| 30 | subdued indoor lighting |
| 60 | display-only workplaces |
| 120 | typical office |
| 240 | bright indoor office |
| 480 | very bright; precision indoor tasks |
| 960 | usual indoors |
| 1920 | bright afternoon |

Figure 15:
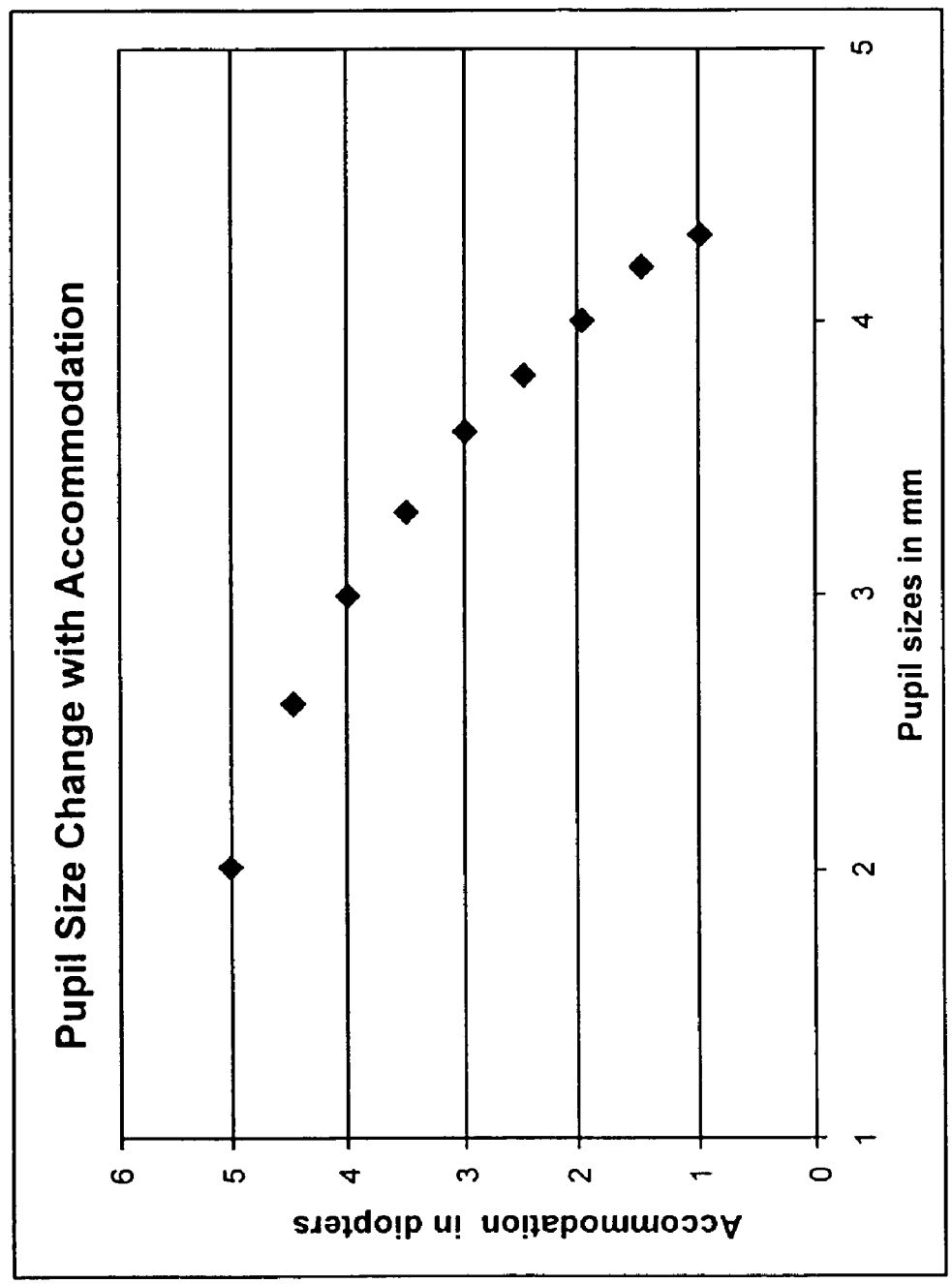
Figure 16:
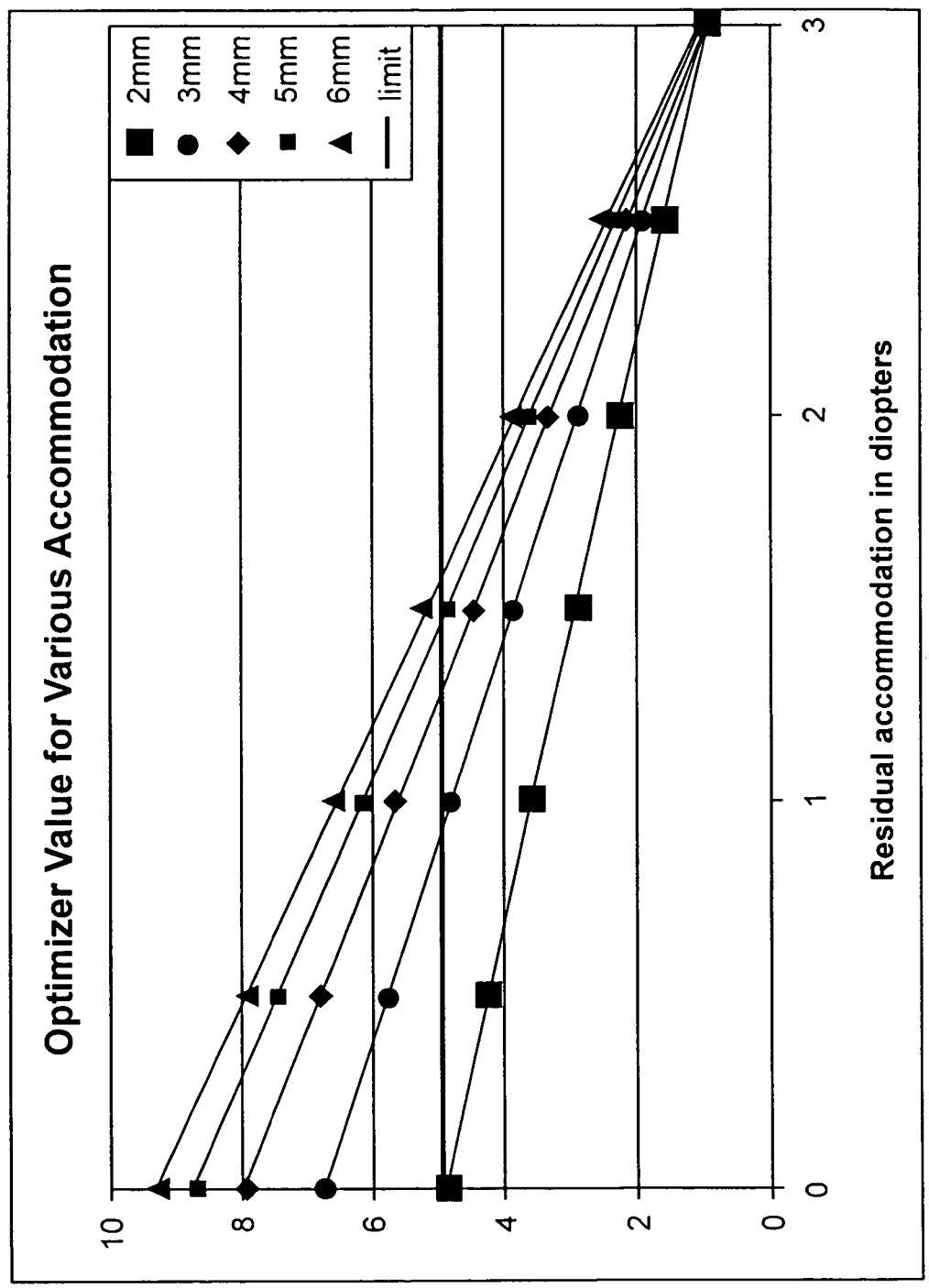
FIG. 16 graphically illustrates optimizer values for differing levels of residual accommodation.

FIG. 15 illustrates that pupil size can change with accommodation, and FIG. 16 illustrates a comparison of corrections by providing optimizer values for various accommodations. With 3 or more diopters of residual accommodation, the optimizer value can achieve a limit of about 1.0, regardless of the pupil size. Typically, a larger amount of residual accommodation can correspond to a smaller optimizer value after optimization. The limit line can correspond to an optimizer value of about 5.0. In other words, an optimizer value of about 5.0 can be viewed as a good practical limit. Either there can be a smaller pupil, or a larger amount of residual accommodation, in order to optimize such that all vergence distances have good visual performance.

Figure 17:
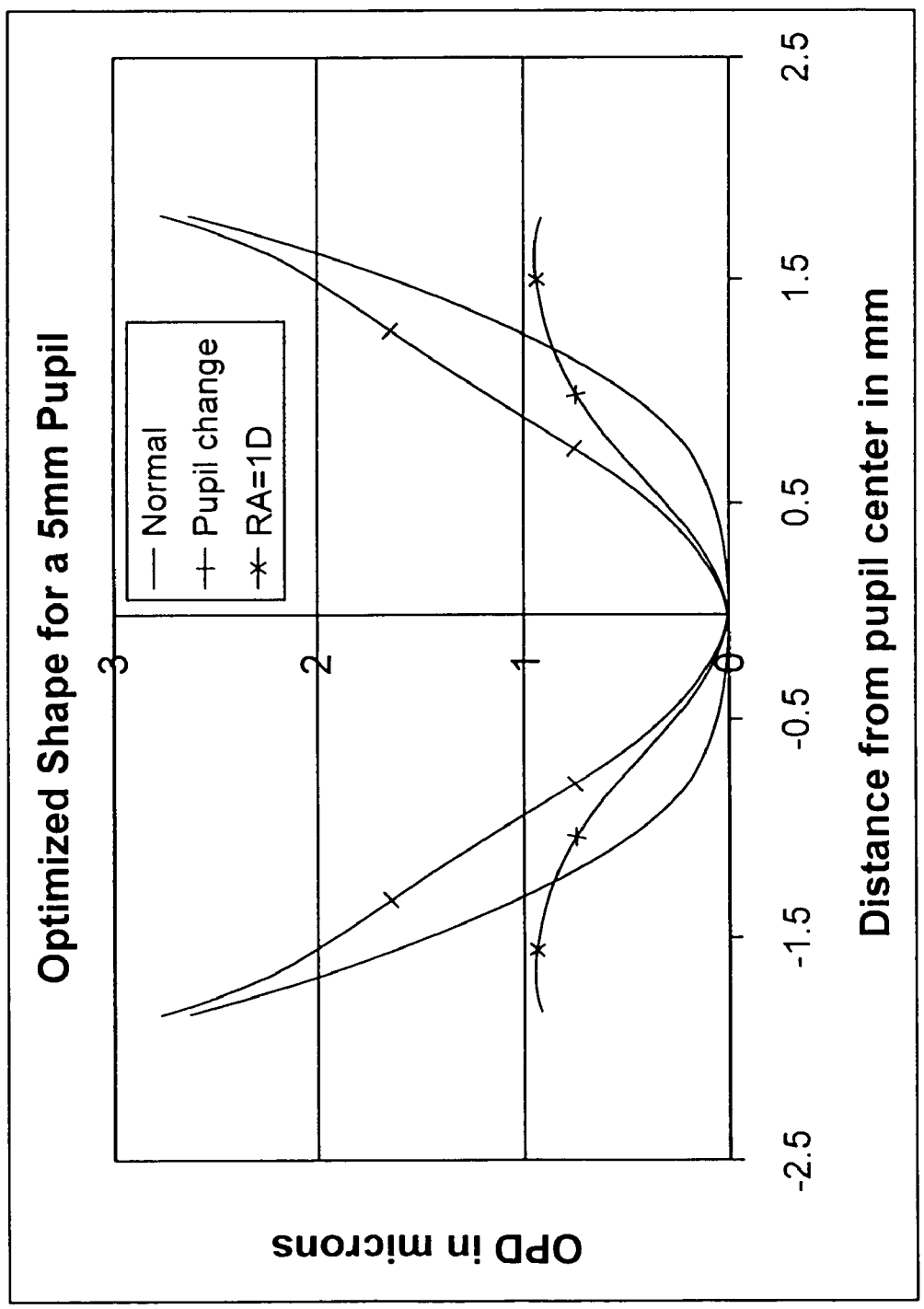
FIG. 17 illustrates effects of pupil change and residual accommodation on presbyopia-mitigating optimized prescriptions for a particular patient.
Figure 18A:
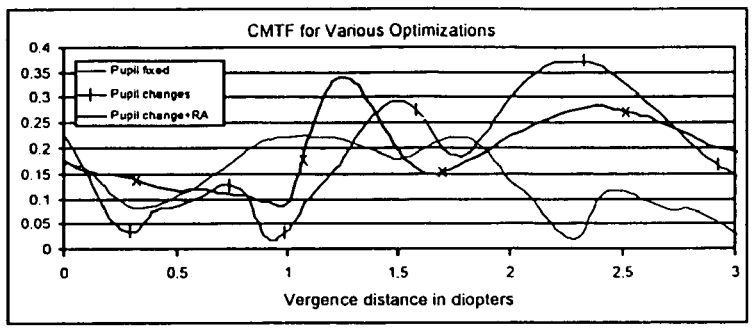
FIGS. 18A-C illustrate effects of pupil change and residual accommodation on presbyopia-mitigating optimized prescriptions for a particular patient.
Figure 18B:
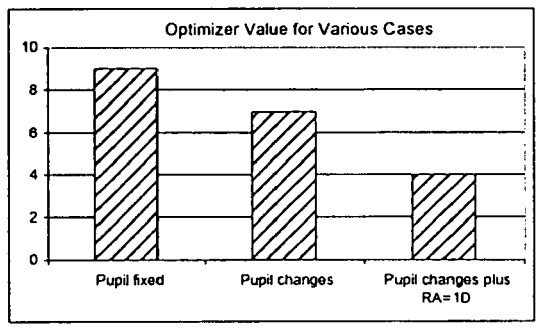
Figure 18C:
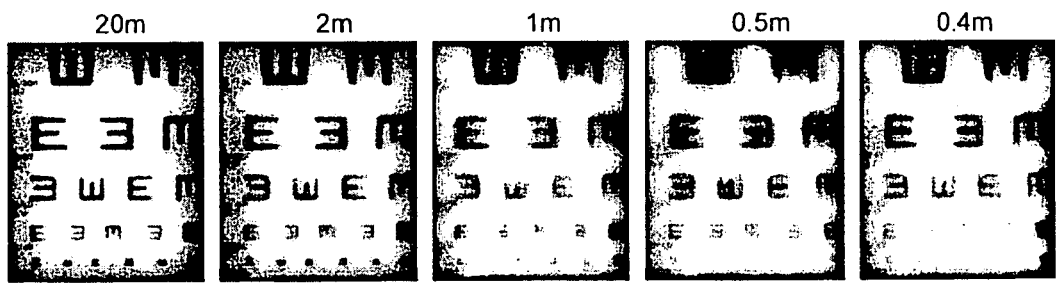
Figure 18C:
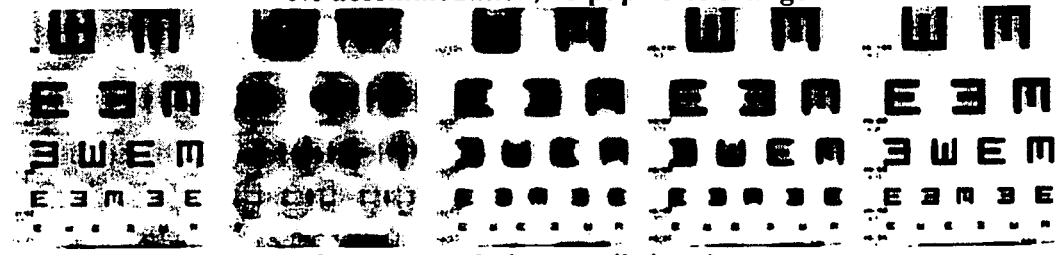
Figure 18C:
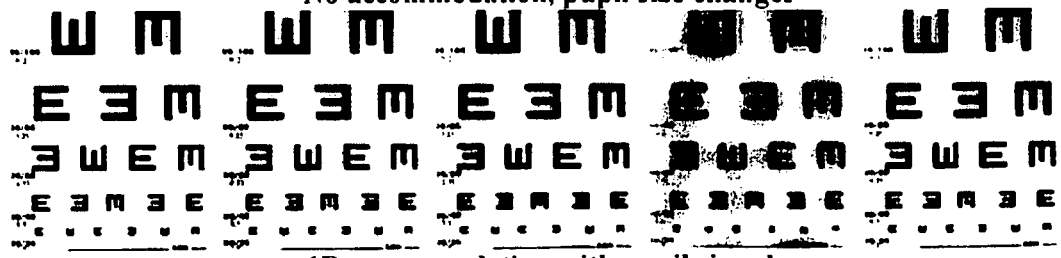

FIGS. 17 and 18 show optimizations under various accommodation conditions. FIGS. 18A and 18B show CMTF and optimizer values when pupil size changes and Residual Accommodation (RA) are modeled. FIG. 18C shows simulated eye charts seen at different target distances after optimization, all assuming a 5 mm maximum pupil size. Each eye chart has 2/100, 20/80, 20/60, 20/40, and 20/20 lines. The top line simulates no accommodation and no pupil size changes. The middle line assumes no accommodation but the pupil size changes from 5 mm (dim distance) to 2.5 mm (bright near). In the bottom line, the simulation assumes 1 D accommodation with pupil size changes from 5 mm (dim distance) to 2.5 mm (bright near).

Figure 19:
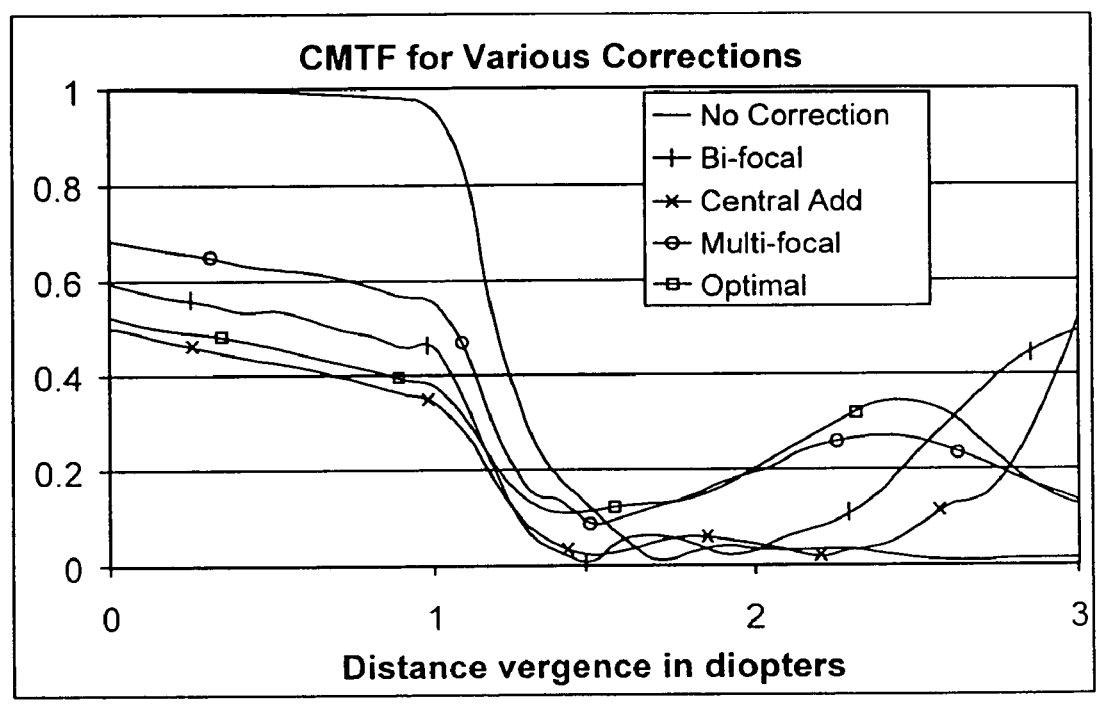
FIGS. 19-21 compare optical properties and results of eyes corrected with a presbyopia-mitigating optimized prescriptions to alternative treatments.
Figure 20:
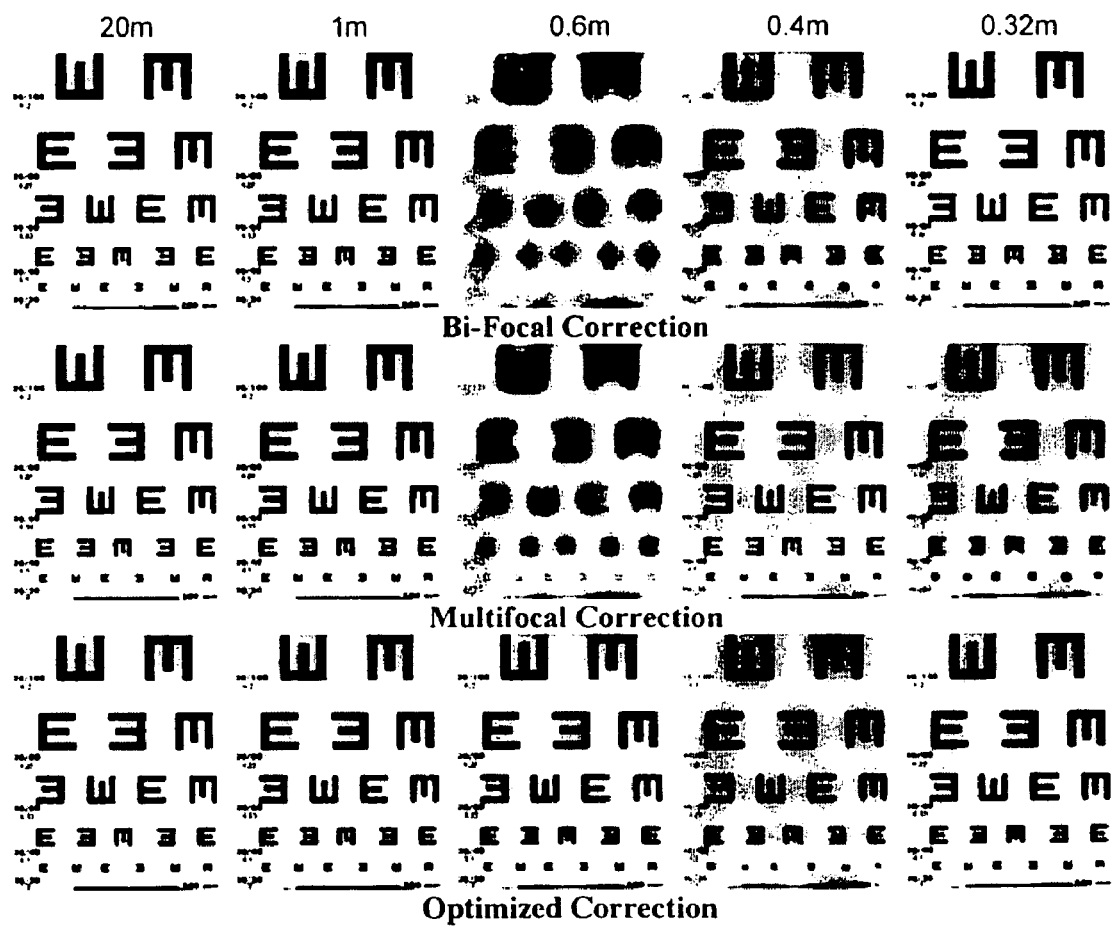
Figure 21:
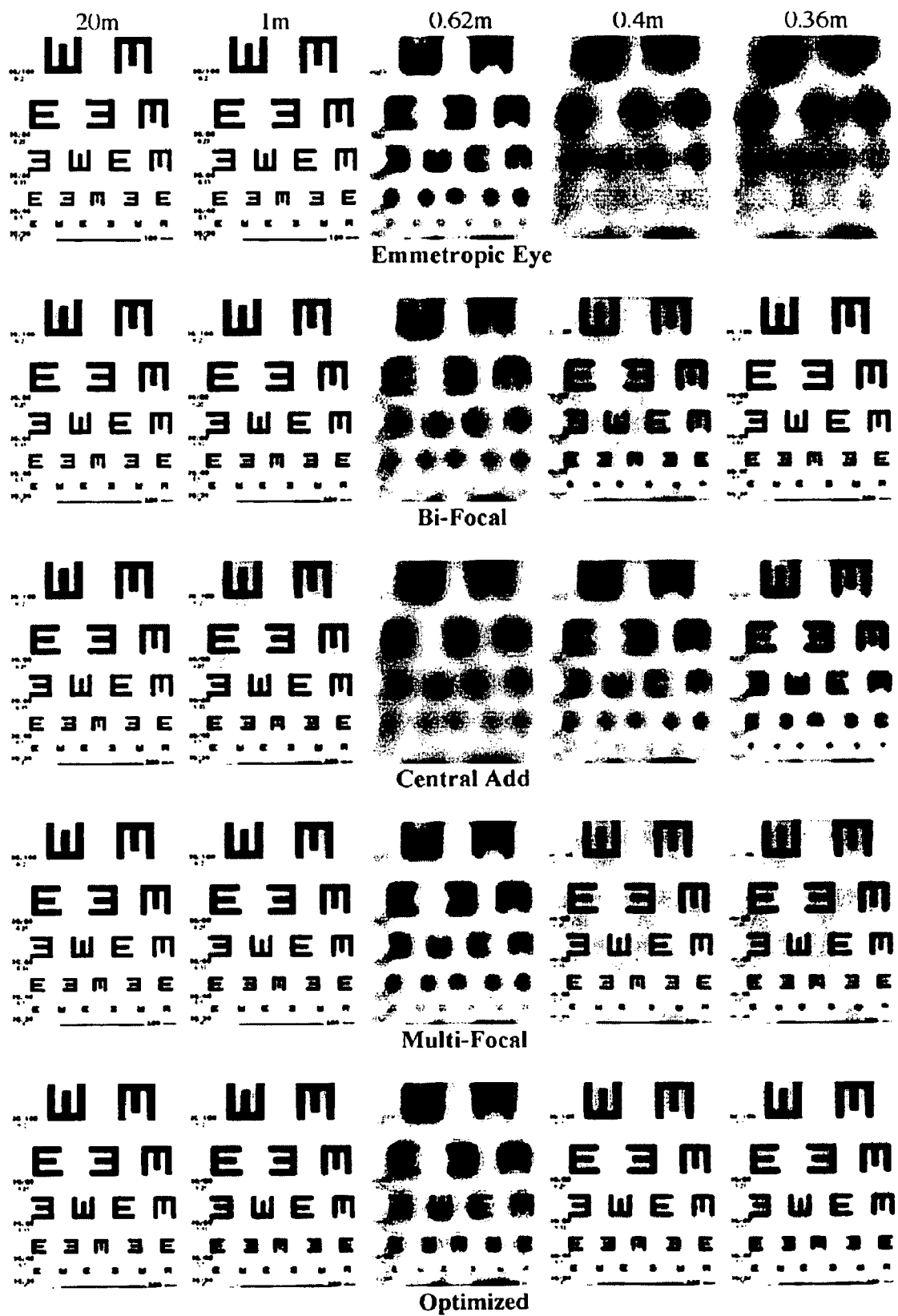

FIG. 19 shows CMTF values for various corrections. A 5 mm pupil eye is assumed, along with a smallest pupil size of 2.5 mm (bright light reading condition) and a 1 D residual accommodation. FIG. 20 compares bi-focal, optimal, and multi-focal corrections, under the assumption of a one diopter residual accommodation. These simulated eye charts are seen at different target distances after optimization. 1 D accommodation and a 5 mm pupil changes from 5 mm (dim distance) to 2.5 mm (bright near) are assumed. The eye chart has 2/100, 20/80, 20/60, 20/40, and 20/20 lines, respectively. FIG. 21 illustrates a simulated eye chart seen at different target distances. The data in this figure based on the assumption that the pupil size decreases from 5 mm to 2.5 mm, and there is a 1 diopter residual accommodation in all cases.

The customized shape methods and systems of the present invention can be used in conjunction with other optical treatment approaches. For example, co-pending U.S. provisional patent application No. 60/431,634, filed Dec. 6, 2002 and co-pending U.S. provisional patent application No. 60/468,387 filed May 5, 2003, the disclosures of which are hereby incorporated by reference for all purposes, describe an approach to defining a prescription shape for treating a vision condition in a particular patient. The approach involves determining a prescriptive refractive shape configured to treat the vision condition, the prescriptive shape including an inner or central "add" region and an outer region. The approach also includes determining a pupil diameter of the particular patient, and defining a prescription shape comprising a central portion, the central portion having a dimension based on the pupil diameter, the inner region of the prescriptive refractive shape, and an attribute of at least one eye previously treated with the prescriptive refractive shape.

Accordingly, the present invention can include a method for determining a customized shape that includes a scaled central portion as described above, the customized shape giving results at least as good or better than previously known methods.

Systems

The present invention also provides systems for providing practical customized or optimized prescription shapes that mitigate or treat presbyopia and other vision conditions in particular patients. The systems can be configured in accordance with any of the above described methods and principles.

Figure 22:
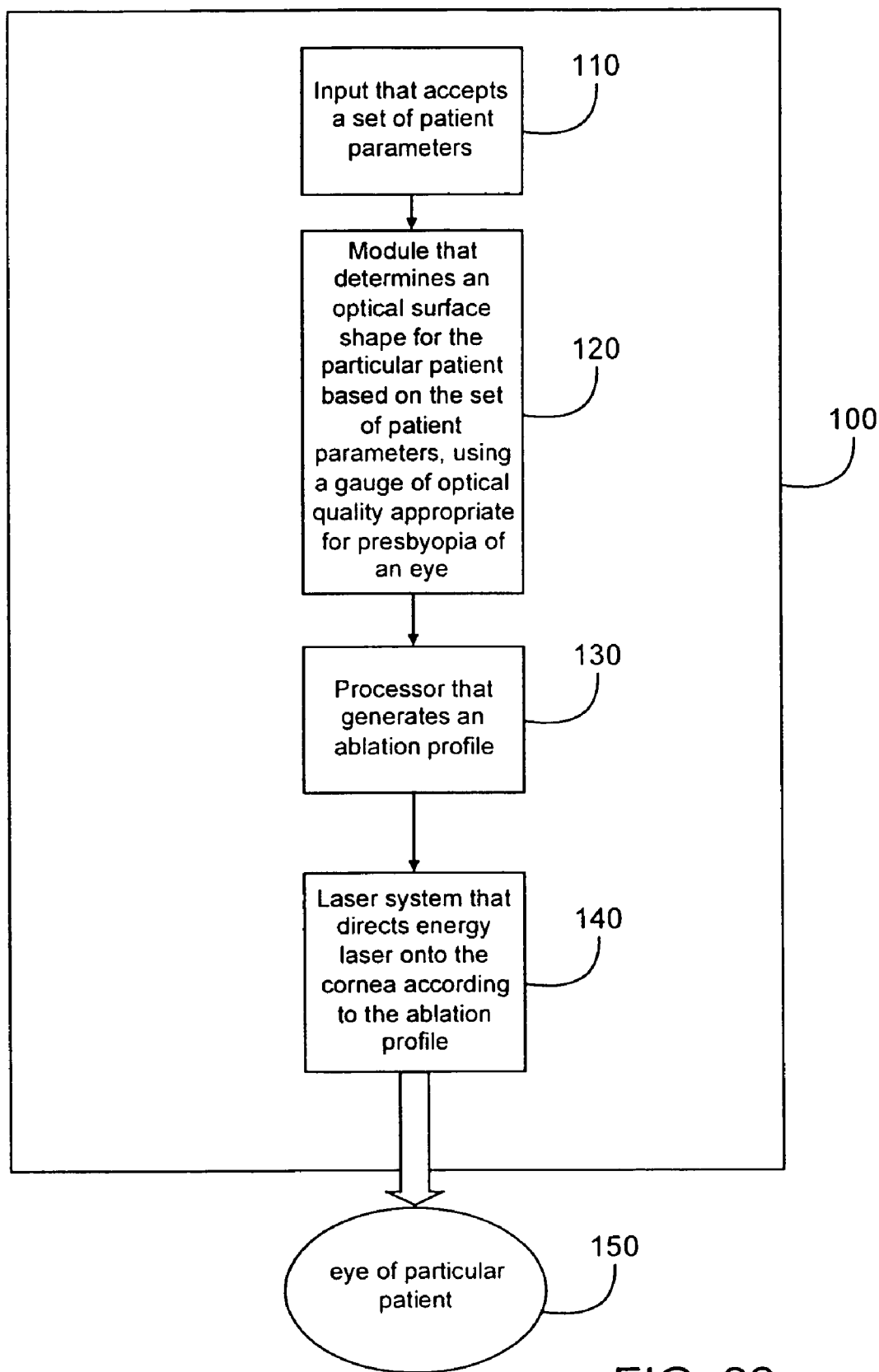
FIG. 22 schematically illustrates a system for determining a presbyopia-mitigating prescription for a particular patient and delivering that treatment using laser refractive surgery.

For example, as shown in FIG. 22, a system 100 can be used for reprofiling a surface of a cornea of an eye 150 of a particular patient from a first shape to a second shape having correctively improved optical properties. System 100 can comprise an input 110 that accepts a set of patient parameters, a module 120 that determines an optical surface shape for the particular patient based on the set of patient parameters, using a goal function appropriate for presbyopia of an eye, a processor 130 that generates an ablation profile, and a laser system 140 that directs laser energy onto the cornea according to the ablation profile so as to reprofile a surface of the cornea from the first shape to the second shape, wherein the second shape corresponds to the prescription shape.

Defining a Scaled Prescription Shape for a Vision Condition Determining a Prescriptive Prescription Shape Certain prescriptive refractive shapes are effective in treating vision conditions, and it is possible to provide an efficient prescription shape by scaling a shape to the particular patient being treated. Optical shapes can be scaled based on data collected from subjects previously treated with a uniform prescriptive optical shape, such as measured manifest powers for different pupil sizes. Shapes may also be scaled based on the desired overall optical power of the eye under differing viewing conditions.

It is useful to select or construct an initial prescriptive refractive shape appropriate for the vision condition. For example, prescriptive treatment shapes such as those shown in FIG. 23 have been found to provide a range of good focus to the eye so as to mitigate presbyopia. This particular prescriptive shape is the sum of two component shapes: a base curve treatment defining an outer region having a diameter of about 6.0 mm, and a refractive add defining an inner region having a diameter of about 2.5 mm. Prescriptive shapes such as this can provide a spherical power add ranging from between about 1.0 diopters to about 4.0 diopters at the inner region. Further, the spherical power add can be about 3.1 diopters. Combining the inner and outer regions, the overall prescriptive refractive shape can be aspheric. It is appreciated, however, that the dimensions and properties of a prescriptive shape can vary depending on the intended purpose of the shape.

Figure 24:
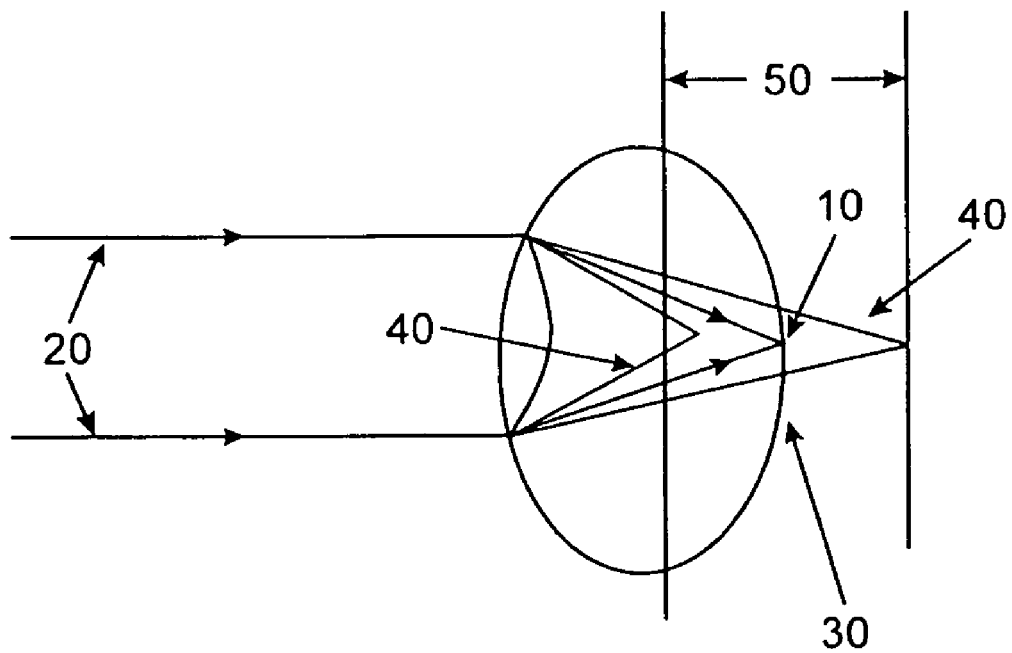
FIGS. 24 and 25 schematically illustrates residual accommodation and presbyopia treatments for increasing a focal range.

Treatment of presbyopia often involves broadening the focus range of the eye. Referring to FIG. 24, in an emmetropic eye a focal length of the optical system results in a point of focus 10 that produces a sharp image. At this point, the refractive power of the cornea and lens is matched to the length of the eye. Consequently, light rays 20 entering the eye converge on the retina 30. If there is a difference between the refractive power and the length of the eye, however, the light rays can converge at a point 40 in front of or behind the retina, and the image formed on the retina can be out of focus. If this discrepancy is small enough to be unnoticed, it is still within the focus range 50 or depth of focus. In other words, the image can be focused within a certain range either in front of or in back of the retina, yet still be perceived as clear and sharp.

Figure 25:
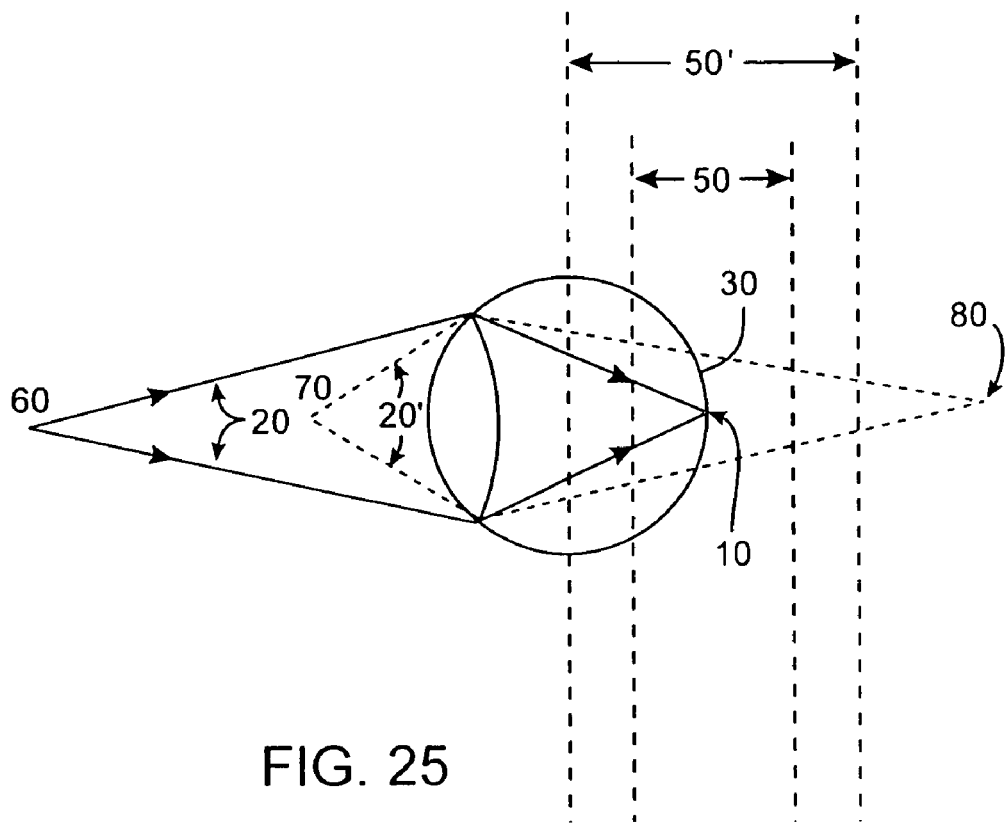

As shown in FIG. 25, when an object is at a far distance 60 from the eye, the light rays 20 converge on the retina 30, at focal point 10. When the object is moved to a near distance 70, the light rays 20' converge at a focal point 80 beyond the retina. Because the image is outside of the depth of focus 50, the image is perceived to be blurred. Through the process of accommodation, the lens changes shape to increase the power of the eye. The power increase brings the focal point 80 back toward the retina as the eye attempts to reduce the blur.

In the presbyopic eye the accommodative mechanism may not work sufficiently, and the eye may not be able to bring the focal point to the retina 30 or even within the range of focus 50. In these circumstances, it is desirable to have an optical system having a broadened focus range 50'. One way to achieve this is by providing an optical system with an aspheric shape. The aspheric shape, for example, can be ablated on a surface of the eye, the surface often comprising a stromal surface formed or exposed by displacing or removing at least a portion of a corneal epithelium, or a flap comprising corneal epithelium, Bowman's membrane, and stroma. Relatedly, the shape can be provided by a correcting lens. In some optical systems, only a portion of the shape may be aspheric. With an aspheric shape, there is not a single excellent point of focus. Instead, there is greater range of good focus. The single best focus acuity is compromised, in order to extend the range of focus. By extending the range of focus 50 to a broadened range of focus 50', there is an improvement in the ability to see both distant and near objects without the need of 3 D or more in residual accommodation.

Figure 23:
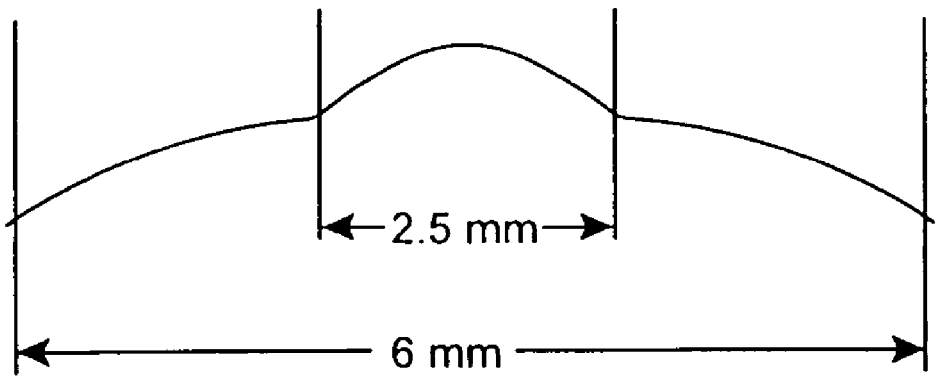
FIG. 23 schematically illustrates a presbyopia-mitigating shape having a central add region.

Without being bound by any particular theory, it is believed that the power add of the inner region depicted in FIG. 23 provides a myopic effect to aid near vision by bringing the near vision focus closer to the retina, while the outer region remains unaltered for distance vision. In this sense the application of this prescriptive shape is bifocal, with the inner region being myopic relative to the outer region. Put another way, the eye can use the inner region for near vision, and can use the whole region for distance vision.

In a laser ablation treatment, the prescriptive refractive ablation shape can have fairly abrupt changes, but post ablation topographies may show that healing of the eye can smooth the transitions. The shape can be applied in addition to any additional required refractive correction by superimposing the shape on a refractive corrective ablation shape. Examples of such procedures are discussed in co-pending U.S. patent application Ser. No. 09/805,737, filed Mar. 13, 2001 the disclosure of which is herein incorporated by reference for all purposes.

Alternative presbyopia shapes may also be scaled using the techniques described herein, optionally in combination with other patient customization modifications, as can be understood with reference to U.S. Provisional Patent Application Nos. 60/468,387 filed May 5, 2003, 60/431,634, filed Dec. 6, 2002, and 60/468,303, filed May 5, 2003, the disclosures of which are herein incorporated by reference for all purposes. Alternative presbyopia shapes may include concentric add powers along a peripheral or outer portion of the pupil, along an intermediate region between inner and outer regions, along intermittent angular bands, or the like; asymmetric (often upper or lower) add regions, concentric or asymmetric subtrace or aspheric regions, and the like. The present application also provides additional customized refractive shapes that may be used to treat presbyopia.

Determining a Pupil Diameter of the Particular Patient

When scaling a refractive shape to treat a particular patient, it is helpful to determine the pupil diameter of the particular patient to be treated. Several methods may be used to measure the pupil diameter, including image analysis techniques and wavefront measurements such as Wavescan® (VISX, Incorporated, Santa Clara, Calif.) wavefront measurements. The size of the pupil can play a role in determining the amount of light that enters the eye, and can also have an effect on the quality of the light entering the eye. When the pupil is very constricted, a relatively small percentage of the total light falling on the cornea may actually be allowed into the eye. In contrast, when the pupil is more dilated, the light allowed into the eye may correspond to a greater area of the cornea. Relatedly, the central portions of the cornea have a more dominant effect on the light entering the eye than do the peripheral portions of the cornea.

Pupil size can have an effect on light quality entering the eye. When the pupil size is smaller, the amount of light passing through the central portion of the cornea is a higher percentage of the total light entering the eye. When the pupil size is larger, however, the amount of light passing through the central portion of the cornea is a lower percentage of the total light entering the eye. Because the central portion of the cornea and the peripheral portion of the cornea can differ in their refractive properties, the quality of the refracted light entering a small pupil can differ from that entering a large pupil. As will be further discussed below, eyes with different pupil sizes may require differently scaled refractive treatment shapes.

An Inner Region of the Prescriptive Refractive Shape

Experimental data from previously treated eyes can provide useful information for scaling a refractive treatment shape for a particular patient. For example, a refractive shape for a particular patient can be scaled based on certain characteristics or dimensions of the shape used to treat the eyes of the subjects. One useful dimension of the above-described presbyopic prescriptive shape is a size or diameter of inner region or refractive add. It is possible to scale a treatment shape for a particular patient based on the diameter of the refractive add of the prescriptive shape. Alternative techniques might scale a power of an inner, outer, or intermediate region, a size of an outer or intermediate region, or the like.

If the refractive add diameter is small, it can occupy a smaller percentage of the total refractive shape over the pupil. Conversely, if the refractive add diameter is large, it can occupy a greater percentage of the total refractive shape over the pupil. In the latter case, because the area of the periphery is relatively smaller, the distance power is diminished. In other words, the area of the add is taking up more of the total refractive shaped used for distance vision.

An Attribute of a Set of Eyes Previously Treated with the Prescriptive Refractive Shape As noted above, experimental data from previous prescriptive eye treatments can be useful in scaling a treatment for a particular individual. When scaling a presbyopia treatment shape, it is helpful to identify a pupil diameter measure from among a set of previously treated eyes having a fixed treatment size that corresponds to both good distance and near sight. It is possible to use acuity and power measurements from the set of treated eyes to determine such a pupil diameter. The fixed treatment size (e.g. 2.5 mm inner region) can then be said to be appropriate for this identified pupil diameter.

Figure 26:
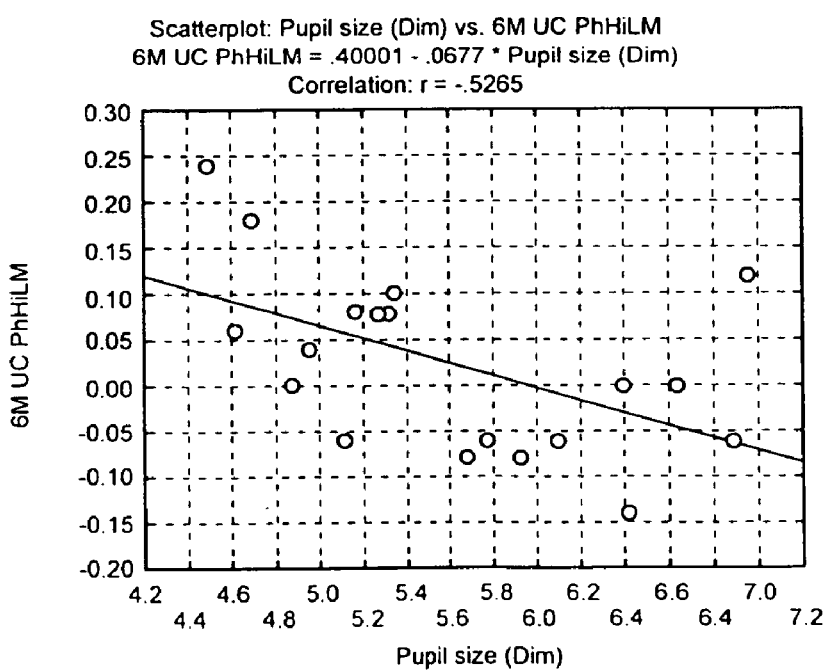
FIGS. 26-32 graphically illustrate results from presbyopia-mitigating treatments for a population of individual patients.
Figure 27:
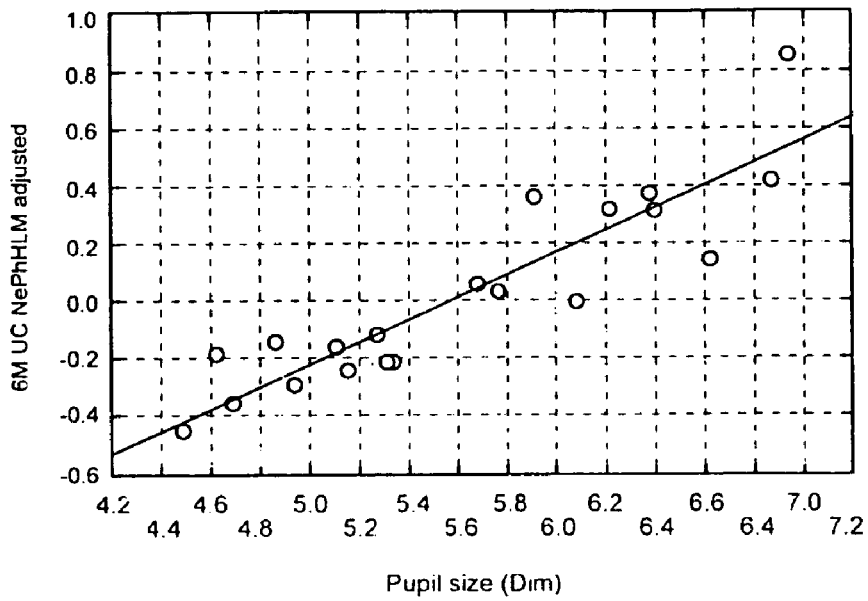

FIGS. 26 and 27 illustrate the effect that pupil size can have on distance acuity and near acuity in subjects treated with a prescriptive refractive shape, for example a shape having a 2.5 mm central add zone of −2.3 diopters. Referring to FIG. 26, pupil size values were obtained from a group of subjects as they gazed into infinity under mesopic or dim light conditions. The 6-month uncorrected distance acuity values were obtained from the same group of subjects under photopic conditions. Referring to FIG. 27, pupil size values were obtained from a group of subjects as they gazed at a near object under mesopic or dim light conditions. The 6-month uncorrected near acuity values were obtained from the same group of subjects under photopic conditions.

One way to determine an optimal pupil diameter measure is by superimposing a near acuity graph over a distance acuity graph, and ascertaining the pupil diameter that corresponds to the intersection of the lines.

Another way to determine a pupil diameter that corresponds to both good distance and near acuity is to define each of the slopes mathematically:

Near acuity=−2.103+0.37879*Pupil size (Dim) (FIG. 27)

Distance acuity=0.40001−0.0677*Pupil size (Dim) (FIG. 26)

By setting the two equations from the graphs equal, it is possible to solve for the intersection point.

−2.103+0.37879*Pupil size (Dim)=0.40001− 0.0677*Pupil size (Dim)

Pupil size (Dim)=2.4/0.45=5.33 mm

An optimum overlap can occur in a range from between about 4.0 mm to about 6.0 mm. Further, an optimum overlap can occur in a range from between about 5.0 mm to about 5.7 mm. These measurements may correspond to a pupil diameter measure from the set of previously treated eyes that corresponds to both good distance and near vision when the diameter of the central add region is 2.5 mm.

Defining a Refractive Shape for Treating a Particular Patient Acuity as a Function of Pupil Size The present invention provides methods and systems for defining a prescription for treating a vision condition in a particular patient, with the prescription optionally comprising a refractive shape. Such a method can be based on the following features: (a) a prescriptive refractive shape configured to treat the vision condition, including an inner region thereof; (b) a pupil diameter of the particular patient, and (c) an attribute of a set of eyes previously treated with the prescriptive shape.

For example, the prescriptive shape can be the shape described in FIG. 23. The inner region of the shape can be a refractive add, having a diameter of 2.5 mm. For illustrative purposes, a pupil diameter of the particular patient of 7 mm is assumed. The attribute of a set of previously treated eyes can be the pupil diameter of the eyes that corresponds to both good distance and near vision, such as the exemplary 5.3 mm treated pupil diameter shown in FIGS. 26 and 27. Thus, a ratio of the prescriptive refractive add to treated pupil (PAR) can be expressed as 2.5/5.3.

The PAR can be used in conjunction with the pupil diameter of the particular patient to scale the refractive shape. For example, a central portion of the scaled refractive shape can be calculated as follows.

central portion diameter=*PAR*\*pupil diameter of particular patient

Given the example above, the diameter of a central portion of the scaled refractive shape for treating the particular patient is:

(2.5/5.3)*7 mm=3.3 mm

In this example, this scaled central portion can correspond to the diameter of the refractive add of the defined refractive shape. It should be appreciated that the refractive shape and the central portion of the refractive shape can alternately be spheric or aspheric. For example, the refractive shape can be aspherical, and the central portion of the refractive shape can be aspherical; the refractive shape can be spherical and the central portion of the refractive shape can be spherical; the refractive shape can be aspherical, and the central portion of the refractive shape can be spherical; or the refractive shape can be spherical, and the central portion of the refractive shape can be aspherical.

As shown above, the PAR can be about 2.5/5.3, or 0.47. It will be appreciated that the PAR can vary. For example, the PAR can range from between about 0.35 and 0.55. In some embodiments, the PAR may range from about 0.2 to about 0.8. Optionally, the PAR can range from about 0.4 to about 0.5. Further, the PAR can range from about 0.43 to about 0.46. It will also be appreciated that the ratios discussed herein can be based on area ratios or on diameter ratios. It should be assumed that when diameter ratios are discussed, that discussion also contemplates area ratios.

Power as a Function of Pupil Size

In another example, the attribute of a set of previously treated eyes can be the pupil diameter of the eyes that correspond to both good distance and near values for spherical manifest. A group of individuals with varying pupil sizes were treated with the same prescriptive refractive shape, the shape having a constant presbyopic refractive add diameter of approximately 2.5 mm. Pupil sizes were obtained on a Wavescan® device. The Spherical Manifest at 6 months post-treatment is shown as a function of the pupil size in FIG. 28. Here, the spherical manifest represents the effective distance power as the result from the total prescriptive shape, including the inner region and outer regions of the shape.

Figure 28:
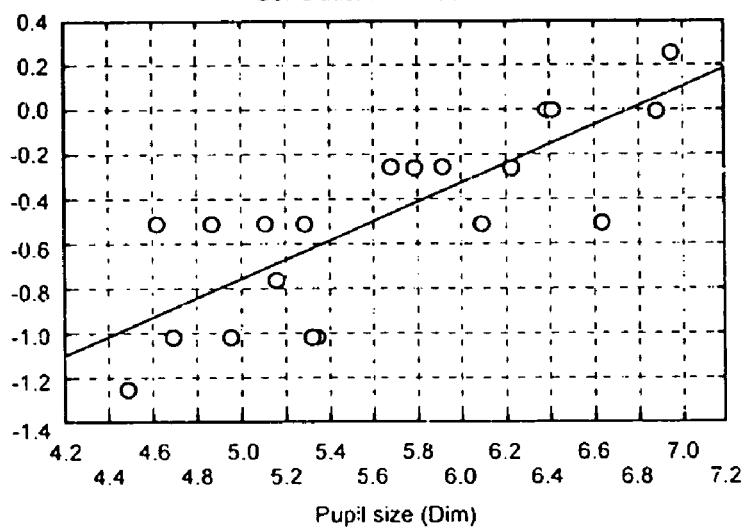

As FIG. 28 illustrates, for a given prescriptive treatment shape, the effect that the shape has on the individual's manifest can depend on the individual's pupil diameter. Depending on the pupil size of the treated subject, the refractive add will have different relative contribution to the power. And due to the varying pupil sizes, the prescriptive refractive add to treated pupil ratio (PAR) may not be constant. Thus, with the same prescriptive treatment, the effective power can vary among different patients. In a simplified model, the power change from the central portion of the treated eye to the periphery can be assumed to be linear. This simplification can be justified by the data. The change in power can be represented by the following formula, expressed in units of diopters.

MRS(Effective Distance Power)=−2.87+0.42*Pupil size(Dim)[diopters]

The rate change in effective power is 0.42 D per mm for distance vision. It has been shown that the pupil diameter can change at a rate of approximately 0.45 D per mm. The add power is −2.87 diopters.

Without being bound by any particular theory, it is thought that due to the asphericity of the central add, there can be a linear relationship between the effective distance power and the pupil diameter. Accordingly, is it possible to characterize the ratio of effective distance power versus pupil diameter with the following linear core equation, where $C_0$ and A are constants.

Effective Distance Power=$C_0$+A(pupil_diameter)    Equation A:

In individuals having smaller pupil diameters, the contribution of the outer region of the prescriptive shape is diminished; the manifest refraction is more myopic and the effective power is smaller. And whereas a lower MRS value can correspond to a more myopic refraction, a higher MRS value can correspond to a less myopic refraction. The manifest refraction, which can be expressed in terms of power, is often proportional to distance vision, which can be expressed in terms of acuity or logarithm of the minimum of angle of resolution (logMAR).

As discussed above, a PAR can be determined based on acuity measurements as a function of pupil size. In an analogous manner, it is possible to determine a PAR based on power measurements as a function of pupil size.

Skewing

The Effective Distance Power Equation A above represents one approach to finding a good approximation to customize the refractive shape size. In sum, the intersection of a distance version of the equation and a near version of the equation is solved to determine a pupil diameter measure, which forms the denominator for the PAR (prescriptive shape add diameter/pupil diameter of treated eye). By adjusting the PAR, it is possible to adjust the shape to achieve emmetropia or other refractive states.

Altering the Size of the Prescriptive Shape Add

Referring to FIG. 28, a treated pupil diameter of about 5.4 mm has a spherical manifest of about −0.6 diopters. If the size of the prescriptive shape add is made bigger, the line can be shifted downward. Consequently, the effect in a particular patient treated with the scaled refractive shape would be a more myopic spherical manifest of −2.0, for example. On the other hand, if the size of the add is made smaller, the line can be shifted upward, and the effect would be a spherical manifest of −0.2, for example. As the diameter of the add decreases, the manifest of the particular patient treated with the scaled refractive shape becomes more skewed to better distance sight. As the diameter of the add increases, the manifest becomes more skewed to better near sight.

Fixing the PAR

It is possible to set the near manifest for all patients by fixing the PAR. Referring to the example of FIGS. 26 and 27 (where the Equation A intersection is about 5.3 mm), a ratio of 2.5/5.3 mm can rotate these near and distance lines toward horizontal, about the 5.3 mm point. In other words, an analysis of particular patients treated with a PAR of 2.5/5.3 is expected to result in manifest versus pupil size plots having lines that are more horizontally oriented. Thus each patient would be expected to have similar near manifest. Alternatively, it is possible to choose a different point of rotation to optimize distance manifest over near manifest, or vice versa. For example, by choosing a 5.0 mm point for rotation, better near manifest can be provided at the expense of the distance manifest.

When comparing the graphs of FIGS. 26 and 27 the distance acuity and near acuity slopes can vary. As shown in these figures, near vision changes at a slightly higher rate than distance vision. In other words, near vision appears to be more sensitive to changes in pupil diameter than distance vision. An adjustment was made to near measurements in FIG. 27 to offset a distance correction used during the measurement.

Non-Linear Models

The effective distance power versus pupil diameter can also be expressed by the following non-linear equation.

Power=$C_0$+A(pupil_diameter)+B(pupil_diameter)$^2$+C(pupil_diameter)$^3$+    Equation B:

where $C_0$, A, B, and C are constants. This equation is only one of many that can be used to model the desired relationship. Similar non-linear equations can be used to model desired effective power, as discussed below. Also, both linear and non-linear equations can be used to model target manifest, as discussed below.

Target Manifest (Acuity as a Function of Power)

Figure 29:
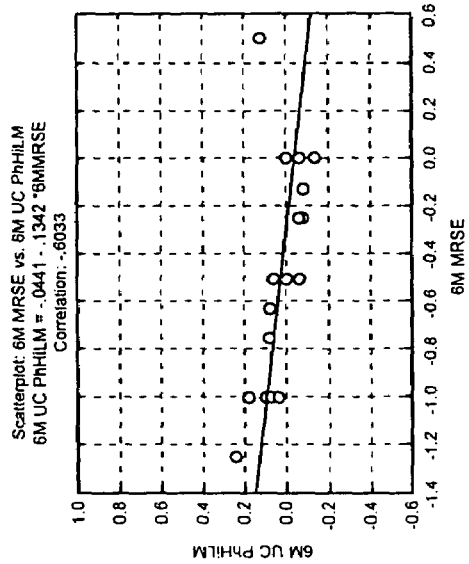
Figure 30:
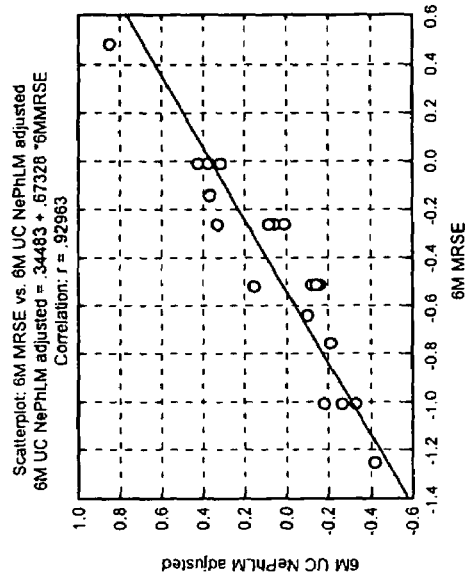

The target manifest or desired power at a particular viewing distance may or may not be emmetropic (0 diopters). For example, near sight may be improved by a manifest which is slightly myopic. Following an analysis similar to that discussed above for pupil size dependency, an optimum target refraction can be calculated based on acuity as a function of power in a set of eyes treated with the prescribed refractive shape. FIGS. 29 and 30 show the distance and near acuity as a function of manifest, respectively. Distance and near acuity versus manifest can be expressed by the following non-linear equations.

Near_Acuity=$A_0$+A(Manifest)+B(Manifest)$^2$+C(Manifest)$^3$+. . .

Distance_Acuity=$A_0$+A(Manifest)+B(Manifest)$^2$+C(Manifest)$^3$+. . .

Applying a first order approximation to the above equations, and using measurements from previous data, the near and distance acuity as a function of manifest can be expressed as follows.

Near_Acuity=0.34+0.67(Manifest)

Dist_Acuity=−0.04−0.13(Manifest)

The intersection between the two functions can be solved as follows.

$$0.34 + 0.67(\text{Manifest}) = -0.04 - 0.13(\text{Manifest})$$

$$\text{Manifest} = \frac{(-0.04 - 0.34)}{0.67 + 0.13} = -0.48 [\text{Diopters}]$$

The point where the two lines meet is about −0.5 D. Therefore, it can be useful to set the target manifest to −0.5 D. The target manifest equations can be refined based on additional data collected from those patients that are treated with the refractive shape. As noted above in reference to FIG. 23, a prescriptive shape may be the sum of a base curve treatment and a central refractive add. It is possible to change the base shape to compensate for any power offset contributed by the central refractive add to the distance manifest.

PAR Refinements Applied to Particular Patients

As additional data is accumulated, it is possible to calculate the higher order terms of Equation B. More particularly, it is possible to calculate the higher order terms from additional subjects who have been treated with refractive shapes corresponding to constant and linear term adjustments. For example, a group of patients can be treated according to the PAR of 2.5/5.3 discussed above, and based on their results, the PAR can be further refined.

Figure 31:
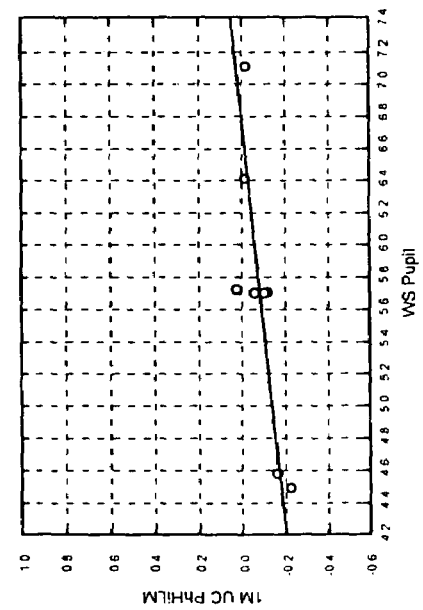
Figure 32:
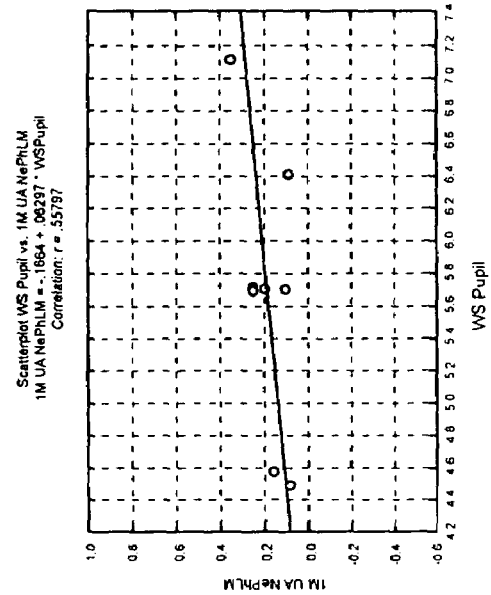

A group of patients had adjustments made to their prescriptive presbyopic shape based on results from the analysis discussed above. The patients were treated with shapes based on a constant PAR of 2.5/5.6 as applied to the central add shape, with a target manifest of −0.5 D. These adjustments rotate the equation about the 5.6 mm line toward horizontal because the near effect is a constant. For example, a 5 mm pupil patient has the same near correction as a 6 mm pupil patient, which means that their near acuity should be the same, i.e. a plot of the near acuity versus pupil size will be a substantially flat line. FIGS. 31 and 32 show the result of these adjustment on this group of patients. As predicted, the lines rotated. The distance acuity of 7 of 8 of these patients was 20/20 (logMAR 0) or better, and the 8th was 20/20+2. Their near acuity slopes have also flattened, with 7/8 patient having simultaneous 20/32−2 acuity or better, and the 8th 20/40. Table 6 summarizes the acuity and power measures.

TABLE 4

| | |
|---|---|
| Near acuity | 0.19 ± 0.1 |
| Distance acuity | −0.08 ± 0.08 |
| MRS | −0.19 ± 0.26 |

This PAR adjusted group has, which is a good result for a presbyopia treatment.

Optimizing a Refractive Shape for a Vision Condition

It is possible to define customized refractive shapes such that they are optimized to treat a particular patient. In one approach to defining an optimized refractive shape, the power of the refractive shape may be based on the central power add of a prescriptive shape, and the power change requirement of the particular patient. Other approaches may involve deriving an appropriate prescription so as to provide a desired overall effective power of the eye at different viewing conditions, again by taking advantage of the changes in pupil size.

Determining a Desired Central Power Add of a Prescriptive Refractive Shape Configured to Treat the Vision Condition A prescriptive shape can be selected for treating the vision condition of the particular patient. For example, the prescriptive shape shown in FIG. 23 can be selected for treating a particular patient having presbyopia. As previously discussed, the central power add of this exemplary prescriptive shape can be about −3.1 diopters.

Determining a Power Change of a Particular Patient

The desired power change of a particular patient can vary widely, and often depends on the patient's desired treatment or a recommendation from a vision specialist. For example, the desired power change of a particular patient having presbyopia can be about −2.5 diopters. The desired power change may be linear or non-linear.

Determining a Pupil Diameter Parameter of the Particular Patient

When defining a refractive shape for treating a vision condition in a particular patient, it is helpful to determine the pupil diameter parameter of the particular patient. Pupil diameters can be measured by, for example, a pupillometer. Pupil diameter parameters can involve, for example, the patient's pupil diameter as measured under certain distance and lighting conditions, such as under photopic conditions while the patient gazes at infinity (distance-photopic). Pupil diameter parameters can also involve pupil diameter measurements under other conditions such as distance-mesopic, distance-scotopic, near-photopic, near-mesopic, or near-scotopic. Still further additional measurements at other viewing conditions, such as at intermediate distances and/or moderate lighting conditions, may also be measured. Often, pupil diameter parameters will be based on two pupil diameter measurements. For example, a pupil diameter parameter can be the value of the particular patient's pupil diameter at distance-photopic minus the patient's pupil diameter at distance scotopic. According to this example, if the distance-photopic pupil diameter is 0.7 mm and the distance-scotopic pupil diameter is 0.2 mm, then the pupil diameter parameter is 0.7 mm minus 0.2 mm, or 0.5 mm.

Defining a Refractive Shape Configured to Treat the Particular Patient, the Power f the Refractive Shape at a Given Diameter Based on: the Central Power Add of the Prescriptive Refractive Shape, the Power Change Requirement of the Particular Patient, and the Pupil Diameter Parameter of the Particular Patient When defining the refractive treatment shape, it can be beneficial to base the power of the refractive shape (Power/ Shape Requirement) at a given diameter based on the central power add of the prescriptive refractive shape, and on the power change requirement of the particular patient. For example, the power of the refractive shape can be a function of a given diameter, as expressed in the following formula.

Power/Shape_Requirement=$C_0$+$A$(pupil_diameter)

where Power/Shape Requirement is the power of the refractive shape at a particular Pupil_Diameter, $C_0$ is the central power add of the prescriptive refractive shape, and $A$ is calculated as $A$=$(PRC-C_0)/PDP$ where PRC is the power change requirement for the particular patient, and PDP is the pupil diameter parameter (obtained, for example, by subtracting the diameter of the pupil measured when the patient is gazing at infinity from the diameter of the pupil measured when the patient is looking at a near object under identical light conditions). Given the values discussed above, the Power/Shape_Requirement (PSR) can be calculated as follows.

$$PSR=-3.1 \text{ diopters}+[(-2.5 \text{ diopters}--3.1 \text{ diopters})/0.5 \text{ mm})](\text{pupil\_diameter})$$

or $$PSR=-3.1 \text{ diopters}+1.2(\text{pupil\_diameter})$$

Other Pupil Diameter Parameters

It is also possible to calculate a pupil diameter parameter based on a pupil diameter change slope as measured under certain distance and lighting conditions, for example, as the patient gazes at infinity while the lighting conditions change from photopic to scotopic (distance-photopic to scotopic). Pupil diameter parameters can also involve pupil diameter change slopes such as near-photopic to scotopic, photopic-distance to near, mesopic-distance to near, or scotopic-distance to near.

The Effective Power

The effective power (e.g., linear power model or higher order model) can be used to calculate or derive a presbyopic shape, optionally based on the following parameters.

F.1. Emmetropic at distance (photopic and mesopic lighting conditions)
 a. This can determine a maximum diameter of the add
F.2. Near can have an effective power of −2.5 D (or more, if desired by the patient
F.3. The rate of change of power for the add-treatment combination can have one of the four:
 i. The same power rate of change as the photopic— Distance to near
 ii. The same power rate of change as the mesopic— Distance to near
 iii. The same power rate of change as the scotopic— Distance to near
 iv. Non-linear rate of change similar to the above, but is optimized to give better simultaneous distance and near vision.

For an eye gazing into infinity, under photopic conditions, the theoretical pupil size at emmetropia can vary within the population. Moreover, the pupil diameter can further vary when the eye is used for different tasks. For example, the pupil diameter can decrease as the eye's gaze changes from infinity to a near object. As the eye changes from a distance gaze to a near gaze, the typical pupil diameter decreases. This change in pupil diameter may be linear with convergence and sigmoid with accommodation. In an eye treated with an exemplary prescriptive shape, the pupil diameter at near gaze can typically have the inner region of the prescriptive shape as the dominant refractive component. Consequently, the change of pupil size from larger to smaller (distance gaze to near gaze) can be equivalent to a change in power. In comparison, the distance gaze pupil will have an effective power based on the combination of the inner region add and the outer region of the prescriptive shape, with the outer region becoming a more dominant refractive component. Therefore, each refractive shape can be customized to each particular individual because of the many different combinations available. By changing the power of the cornea, for example, from emmetropia at the "distance" pupil size to within a range of about −1.0 diopters to about −4.0 diopters myopic for "near" pupil size, it may be possible to mitigate presbyopia.

A general prescription may go as follows. First, measure the continuous pupil size and/or size change at different distances and lighting conditions, such as for at least one (optionally two or more, in some cases all) of: Distance—Photopic; Distance—Mesopic, Distance—Scotopic, Near—Photopic, Near—Mesopic, and/or Near—Scotopic. The pupil size can be affected by the lighting conditions as well as viewing distances. The refractive shape can also include adjustments and/or optimization for lighting. In photopic conditions, the pupil is typically constricted. In scotopic conditions, the pupil is usually dilated. Under mesopic conditions, the pupil can be variably dilated or constricted depending on the specific type of mesopic condition. Second, calculate the pupil diameter continuous rate of change for the following combinations: Distance—photopic to scotopic, Near—photopic to scotopic, Photopic—Distance to near, Mesopic—Distance to near, and/or Scotopic—Distance to near. It is possible to design a shape and ablation size such that patient is substantially emmetropic as pupil size goes from larger (distant) to smaller (near), typically within a range.

The presbyopic lens power can compensate focus such that the lens is the inverse of the rate of pupil change. To do this, the power can change (for example −3 D) for different pupil diameters.

$$\text{Power/Shape\_Requirement}=C_0+A(\text{pupil\_diameter})+B(\text{pupil\_diameter})^2+C(\text{pupil\_diameter})^3+\ldots$$

The Power/Shape_Requirement in the above equation may be effective power, and/or may be manifest power. The power can change with changes in pupil diameter. For a linear power shape, the coefficient A can be calculated as follows.

$$\frac{d(\text{power})}{d(\text{pupil\_diameter})}=A$$

Solving for the linear coefficient, $$A=\frac{PowerChangeRequirement-C_0}{\text{pupil\_diameter\_rate\_of\_change}}$$

The target manifest can be targeted to the patient's request or a doctor's recommendation by using the effective distance power equation as described above in the "target manifest" section.

Multifocal Shapes

A good refractive shape (including a multi-focal shape) may be at or near an optimum compromise between distance and near sight. The near add has an "effective" power—it may not have a single power because of the multi-focal shape. The sum of the peripheral and central add may give the distance power—again it may not have a single power because of the multi-focal shape.

The Age Dependent Presbyopic Shape

Figure 33:
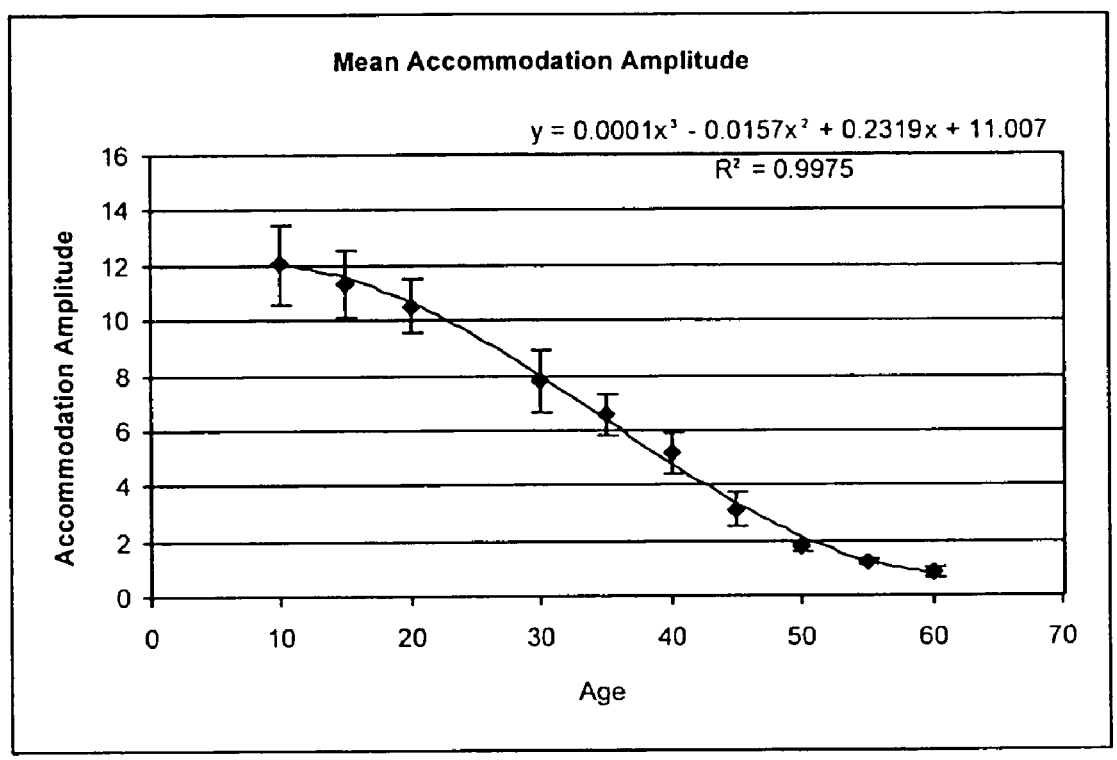
FIG. 33 graphically illustrates accommodation through a range of differing patient ages.

As discussed above, as one ages, accommodation decreases. This is shown in FIG. 33. At 60, accommodation can decrease significantly, even to nearly zero. Studies have shown that pupil sizes decrease as one gets older. As seen in the figure, the slope or rate of change in accommodation also changes with age. It is possible to optimize the pupil dependencies to the age related change in accommodation. The rate of distance and near acuities for a central add shape can be Near_acuity=−2.103+0.37879*Pupil size (Dim)

Distance acuity=0.40001−0.0677*Pupil size (Dim)

According to these equations, as the pupil size decreases, the near acuity gets better, at a rate of 0.37 lines per millimeter. The distance acuity gets worse, but at much slower rate of 0.07 lines per millimeter. Therefore, it is possible to optimize the treatment parameters for the patient's age by targeting the treatment for less myopia. It is possible to allow a shift in the centering of the "range" by taking the residual accommodation into account in the customization of the treatment.

It is possible that the optimum shape may be on a "linear" power approximation as discussed above, but it may consist of higher orders. Though the effective power can be given by the equation above, the shape can be constant over, for example, a central 2.5 mm and have a curvature gradient that will blend the central add to the peripheral region. With this shape it may be beneficial to choose the diameter of the central add to match the patients near pupil such that the near pupil will encompass only the central add when it's at its smallest, and the gradient will be customized to the patient's pupil size rate of change.

Hence, by modeling the residual accommodation, the range of pupil change may be shifted to optimize the "life" long presbyopic correction.

Systems

The present invention also provides systems for scaling refractive shapes and providing practical customized or optimized refractive shapes that mitigate or treat presbyopia and other vision conditions in particular patients. The systems can be configured in accordance with any of the above described methods and principles.

Figure 34:
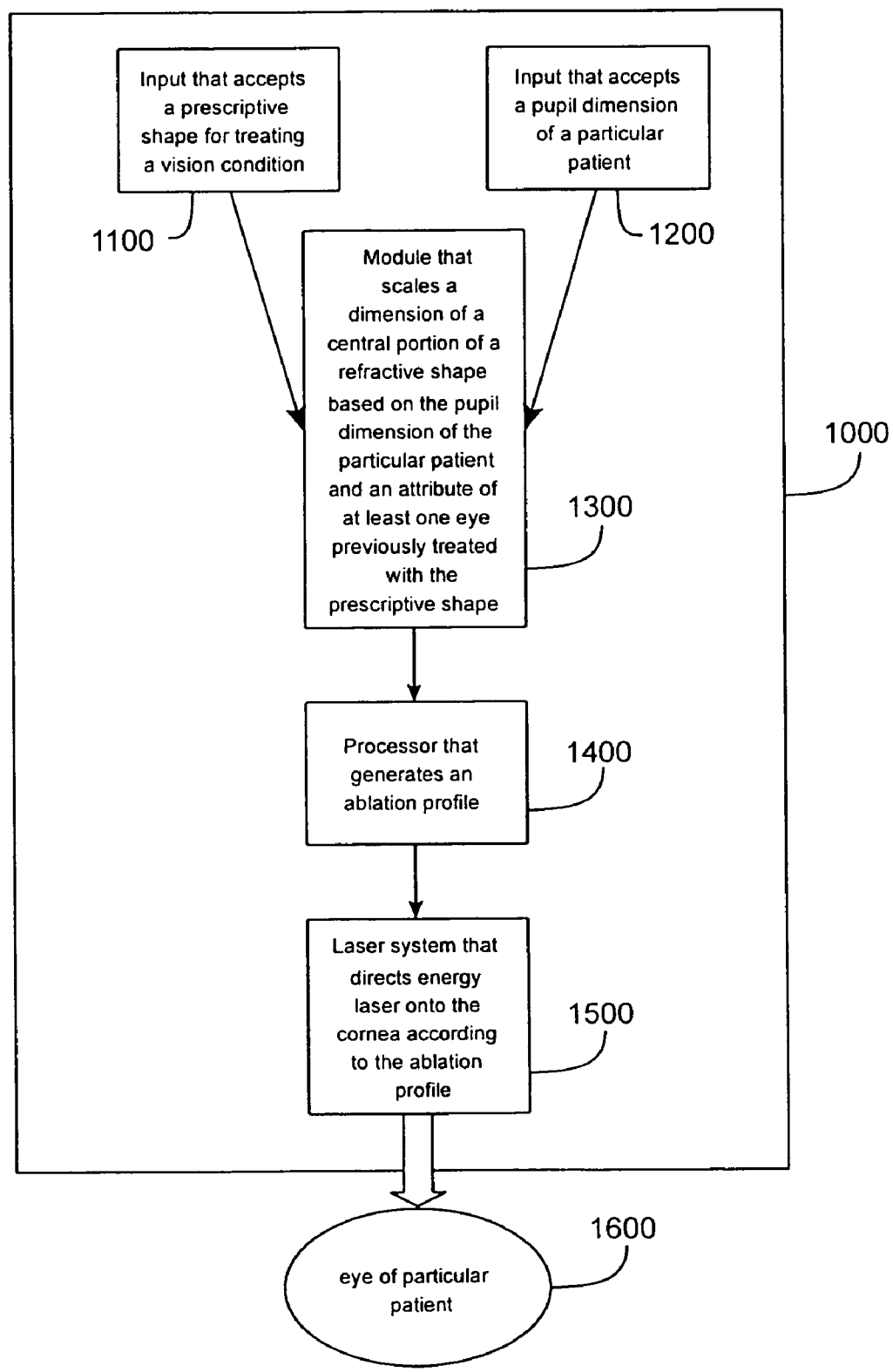
FIG. 34 schematically illustrates another system for determining a presbyopia-mitigating prescription for a particular patient and delivering that treatment using laser refractive surgery.

For example, as shown in FIG. 34, a system 1000 can be used for reprofiling a surface of a cornea of an eye 1600 of a particular patient from a first shape to a second shape having correctively improved optical properties. System 1000 can comprise an input 1100 that accepts a prescriptive shape specific for treating the vision condition, an input 1200 that accepts a pupil dimension of the particular patient, a module 1300 that scales a dimension of a central portion of a refractive shape based on the pupil dimension of the particular patient and an attribute of at least one eye previously treated with the prescriptive shape, a processor 1400 that generates an ablation profile, and a laser system 1500 that directs laser energy onto the cornea according to the ablation profile so as to reprofile a surface of the cornea from the first shape to the second shape, wherein the second shape corresponds to the refractive shape.

Calculating of Presbyopia Mitigating Prescriptions

Methods, Systems, and Devices described herein can be used to generate prescriptions for treatment of refractive errors, particularly for treatment of presbyopia. Such treatments may involve mitigation of presbyopia alone, or may treat a combination of presbyopia with other refractive disorders.

As described above, presbyopia is a condition where the degree of accommodation decreases with the increase of age. Most people have some degree of presbyopia by the age of about 45.

Treatments of presbyopia may involve passive and/or active procedures. In passive procedures, treatment or mitigation is performed in such a way that an improved balance between near vision and distance vision is provided and maintained. In an active procedure, restoration of full or partial accommodation is a goal. So far, active procedures for the correction of presbyopia have not been fully successful.

With passive procedures, it is desirable to provide an improved and/or optimal balance between near vision and distance vision. In order to do that, patients may sacrifice some of their distance vision to gain improved near vision. In addition, they may sacrifice some contrast sensitivity because of the introduction of the asphericity of the new optics of the eye. Fortunately, the sacrifice of distance vision and contrast sensitivity may be mitigated by taking advantage of a pupil shrinkage when the eye accommodates.

As described below, an analytical solution for a presbyopia shape can be achieved based on a desire for different powers at different pupil sizes. In order to understand this, we can take advantage of a concept of optical power that depends on the change of pupil size and might also depend on wavefront aberrations other than defocus terms. We will concentrate on the pupil size dependency in this description.

The following approach considers the correction as a "full pupil" correction rather than "partial pupil" correction as employed with a central add. Healing effect, flap effect as well as how the effective power correlates with the manifest refraction may be addressed with empirical studies, allowing these effects to be fed back into the following calculations and/or a laser ablation planning program as appropriate so as to provide optimized real-world results.

Effective Power and its Application to Presbyopia

As used herein, "effective power" means the optical power that best matches the manifest sphere at a certain pupil size. With wavefront based ocular aberrations, the defocus-dependent effective power can be written as $$P_{eff} = -\frac{4\sqrt{3}\, c_2^0}{R^2}, \tag{1}$$

where R stands for the pupil radius in mm when $c_2^0$ is the Zernike coefficient given in microns in order to get the effective power in diopters, and $P_{eff}$ is effective power. When a wavefront map is defined in radius R with a set of Zernike polynomials, when the pupil shrinks the smaller map, if re-defined with a new set of Zernike polynomials, will have a different set of Zernike coefficients than the original set. Fortunately, analytical as well as algorithmatical solutions of the new set of Zernike coefficients exist. If the original set of Zernike coefficients is represented by $\{c_i\}$ that corresponds to pupil radius $r_1$, then the new set of Zernike coefficients $\{b_i\}$ that corresponds to pupil radius $r_2$ can be expressed by a recursive formula as $$b_{2i}^0 = e^{2i} \sum_{j=0}^{n/2-i} (-1)^j c_{2(i+j)}^0 \sqrt{\frac{2(i+j)+1}{2i+1}} \frac{(2i+j)!}{j!(2i)!} - \sum_{\substack{k=2(i+1) \\ step\ 2}}^{n} b_k^0 \sqrt{\frac{k+1}{2i+1}} \frac{(-1)^{k/2-i}(k/2+i)!}{(k/2-i)!(2i)!}$$

where $e=r_2/r_1$, n is the maximum radial order. As an example, if we set i=1, and n=4, we have the following formula $$b_2^0 = [c_2^0 - \sqrt{15}(1-e^2)c_4^0]e^2$$

Therefore, a power profile with pupil size can be given as a condition to obtain an optical surface for presbyopia correction.

In order to obtain a presbyopia prescription (which will here be an optical shape), let's assume that we know the power profile or desired effective optical powers for different viewing conditions so as to mitigate presbyopia. From the power profile, we can in general do an integration to calculate the wavefront shape. In the following, we consider three cases where two, three, or four power points (different desired effective optical powers for different associated viewing conditions, often being different viewing distances and/or pupil diameters) are known.

Two-Power-Point Solution

Let's consider radially symmetric terms $Z_2^0$ and $Z_4^0$, when the pupil radius is changed from R to eR, where e is a scaling factor not larger than 1, since the new set of Zernike coefficients for the defocus term can be related to its original coefficients as $$b_2^0 = [c_2^0 - \sqrt{15}(1-e^2)c_4^0]e^2 \quad (2)$$

Substituting $c_2^0$ with $b_2^0$, and $R^2$ with $e^2R^2$ in Equation 1 using Equation 2, we have $$4\sqrt{3}c_2^0 - 12\sqrt{5}(1-e^2)c_4^0 = -R^2P. \quad (3)$$

Suppose we request power $p_0$ at radius $e_0R$, and $p_1$ at radius $e_1R$, an analytical solution of the original wavefront shape, which is represented by $c_2^0$ and $c_4^0$, can be obtained as $$c_2^0 = -\frac{(1-e_1^2)p_0 - (1-e_0^2)p_1}{4\sqrt{3}(e_0^2 - e_1^2)}R^2 \quad (4)$$

$$c_4^0 = -\frac{p_0 - p_1}{12\sqrt{5}(e_0^2 - e_1^2)}R^2$$

Figure 35:
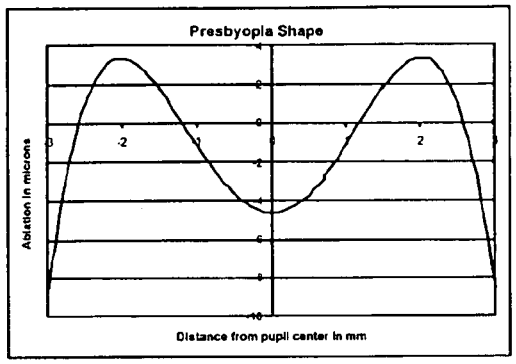
FIGS. 35 and 36 graphically illustrate a presbyopia-mitigating prescription derived so as to provide appropriate effective powers at two differing viewing conditions for a particular patient.
Figure 36:
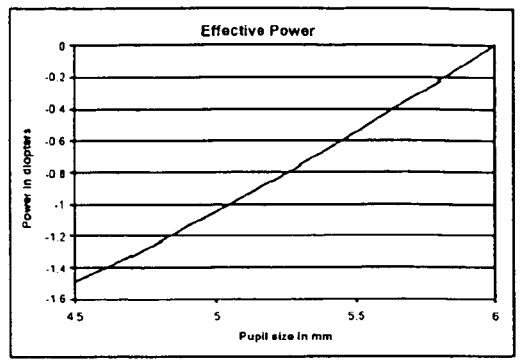

As an example, let's consider a pupil with a dim distance size of 6 mm, requesting effective power of 0 D at pupil size 6 mm and bright reading pupil size of 4.5 mm, requesting effective power of −1.5 D. Substituting $e_0 = 6/6 = 1$, $e_1 = 4.5/6 = 0.75$, and $p_0 = 0$ and $p_1 = -1.5$, we get $c_2^0 = 0$ and $c_4^0 = -1.15$. FIGS. 35 and 36 show the presbyopia shape and effective power as a function of pupil size. It is very close to a linear relationship.

Three-Power-Point Solution

Let's consider radially symmetric terms $Z_2^0$, $Z_4^0$ and $Z_6^0$, when the pupil radius is changed from R to eR, where e is a scaling factor not larger than 1, since the new set of Zernike coefficients for the defocus term can be related to its original coefficients as $$b_2^0 = [c_2^0 - \sqrt{15}(1-e^2)c_4^0 + \sqrt{21}(2-5e^2+3e^4)c_6^0]e^2 \quad (5)$$

Substituting $c_2^0$ with $b_2^0$, and $R^2$ with $e^2R^2$ in Equation 1 using Equation 5, we have $$4\sqrt{3}c_2^0 - 12\sqrt{5}(1-e^2)c_4^0 + 12\sqrt{7}(2-5e^2+3e^4)c_6^0 = -R^2P. \quad (6)$$

Suppose we request power $p_0$ at radius $e_0R$, $p_1$ at radius $e_1R$, and $p_2$ and radius $e_2R$, an analytical solution of the original wavefront shape, which is represented by $c_2^0$, $c_4^0$ and $c_6^0$, can be obtained as $$c_2^0 = -\frac{\begin{array}{c}(1-e_1^2)(1-e_2^2)(e_1^2-e_2^2)p_0 - \\ (1-e_0^2)(1-e_2^2)(e_0^2-e_2^2)p_1 + \\ (1-e_0^2)(1-e_1^2)(e_0^2-e_1^2)p_2\end{array}}{4\sqrt{3}\,(e_1^2-e_2^2)(e_0^2-e_1^2)(e_0^2-e_2^2)}R^2 \quad (7)$$

$$c_4^0 = -\frac{\begin{array}{c}(5-3e_1^2-3e_2^2)(e_1^2-e_2^2)p_0 - \\ (5-3e_0^2-3e_2^2)(e_0^2-e_2^2)p_1 + \\ (5-3e_0^2-3e_1^2)(e_0^2-e_1^2)p_2\end{array}}{36\sqrt{5}\,(e_1^2-e_2^2)(e_0^2-e_1^2)(e_0^2-e_2^2)}R^2$$

$$c_6^0 = -\frac{(e_1^2-e_2^2)p_0 - (e_0^2-e_2^2)p_1 + (e_0^2-e_1^2)p_2}{36\sqrt{7}\,(e_1^2-e_2^2)(e_0^2-e_1^2)(e_0^2-e_2^2)}R^2$$

Figure 37:
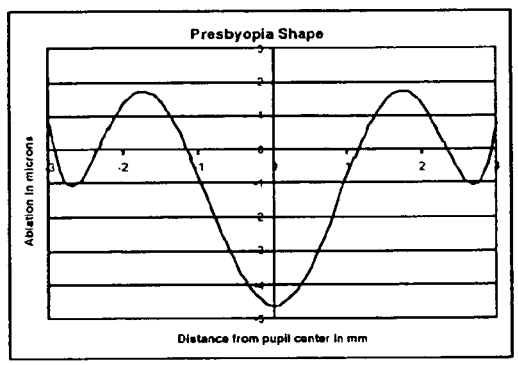
FIGS. 37 and 38 graphically illustrate a presbyopia-mitigating prescription derived so as to provide appropriate effective powers at three differing viewing conditions for a particular patient.
Figure 38:
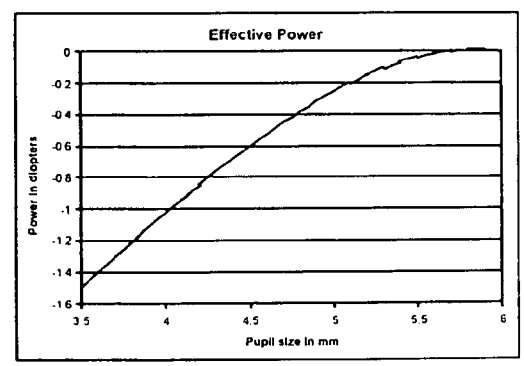

As an example, let's consider a pupil with WaveScan pupil size of 6 mm, and dim distance pupil size of 6 mm, requesting effective power of 0 D and bright reading pupil of 3.5 mm, requesting effective power of −1.5 D. In between are the dim reading and bright distance, with combined pupil size of 4.5 mm with effective power of −0.5 D. Substituting $e_0 = 6/6 = 1$, $e_1 = 4.5/6 = 0.75$, and $e_2 = 3.5/6 = 0.583$ as well as $p_0 = 0$, $p_1 = -0.6$ and $p_2 = -1.5$, we get $c_2^0 = 0$, $c_4^0 = -0.31814$ and $c_6^0 = 0.38365$. FIGS. 37 and 38 shows the presbyopia shape and the effective power as a function of pupil sizes.

Four-Power-Point Solution

Let's consider radially symmetric terms $Z_2^0$, $Z_4^0$, $Z_6^0$ and $Z_8^0$, when the pupil radius is changed from R to eR, where e is a scaling factor not larger than 1, since the new set of Zernike coefficients for the defocus term can be related to its original coefficients as $$b_2^0 = [c_2^0 - \sqrt{15}(1-e^2)c_4^0 + \sqrt{21}(2-5e^2+3e^4)c_6^0 - \sqrt{3}(10-45e^2+63e^4-28e^6)c_8^0]e^2 \quad (8)$$

Substituting $c_2^0$ with $b_2^0$, and $R^2$ with $e^2R^2$ in Equation 1 using Equation 8, we have $$4\sqrt{3}c_2^0 - 12\sqrt{5}(1-e^2)c_4^0 + 12\sqrt{7}(2-5e^2+3e^4)c_6^0 - 12(10-45e^2+63e^4-28e^6)c_8^0 = -R^2P \quad (9)$$

Suppose we request power $p_0$ at radius $e_0R$, $p_1$ at radius $e_1R$, $p_2$ and radius $e_2R$, and $p_3$ and radius $e_3R$, an analytical solution of the original wavefront shape, which is represented by $c_2^0$, $c_4^0$, $c_6^0$ and $c_8^0$, can be obtained as:

$$c_2^0 = -R^2 \frac{\alpha_3 p_0 - \beta_3 p_1 + \gamma_3 p_2 - \delta_3 p_3}{4\sqrt{3}\,\lambda} \quad (10)$$

$$c_4^0 = -R^2 \frac{\alpha_2 p_0 - \beta_2 p_1 + \gamma_2 p_2 - \delta_2 p_3}{252\sqrt{5}\,\lambda}$$

$$c_6^0 = -R^2 \frac{\alpha_1 p_0 - \beta_1 p_1 + \gamma_1 p_2 - \delta_1 p_3}{144\sqrt{7}\,\lambda}$$

$$c_8^0 = -R^2 \frac{\alpha_0 p_0 - \beta_0 p_1 + \gamma_0 p_2 - \delta_0 p_3}{336\lambda}$$

where $$\lambda = (e_0^2-e_1^2)(e_0^2-e_2^2)(e_0^2-e_3^2)(e_1^2-e_2^2)(e_1^2-e_3^2)(e_2^2-e_3^2) \quad (11)$$

$$\alpha_0 = (e_1^2-e_2^2)(e_1^2-e_3^2)(e_2^2-e_3^2) \quad (12)$$

$$\beta_0 = (e_0^2-e_2^2)(e_0^2-e_3^2)(e_2^2-e_3^2) \quad (13)$$

$$\gamma_0 = (e_0^2-e_1^2)(e_0^2-e_3^2)(e_1^2-e_3^2) \quad (14)$$

$$\delta_0 = (e_0^2 - e_1^2)(e_0^2 - e_2^2)(e_1^2 - e_2^2) \quad (15)$$

$$\alpha_1 = [9 - 4(e_1^2 + e_2^2 + e_3^2)]\alpha_0 \quad (16)$$

$$\beta_1 = [9 - 4(e_0^2 + e_2^2 + e_3^2)]\beta_0 \quad (17)$$

$$\gamma_1 = [9 - 4(e_0^2 + e_1^2 + e_3^2)]\gamma_0 \quad (18)$$

$$\delta_1 = [9 - 4(e_0^2 + e_1^2 + e_2^2)]\delta_0 \quad (19)$$

$$\alpha_2 = [45 - 35(e_1^2 + e_2^2 + e_3^2) + 21(e_1^2 e_2^2 + e_1^2 e_3^2 + e_2^2 e_3^2)]\alpha_0 \quad (20)$$

$$\beta_2 = [45 - 35(e_0^2 + e_2^2 + e_3^2) + 21(e_0^2 e_2^2 + e_0^2 e_3^2 + e_2^2 e_3^2)]\beta_0 \quad (21)$$

$$\gamma_2 = [45 - 35(e_0^2 + e_1^2 + e_3^2) + 21(e_0^2 e_1^2 + e_0^2 e_3^2 + e_1^2 e_3^2)]\gamma_0 \quad (22)$$

$$\delta_2 = [45 - 35(e_0^2 + e_1^2 + e_2^2) + 21(e_0^2 e_1^2 + e_0^2 e_2^2 + e_1^2 e_2^2)]\delta_0 \quad (23)$$

$$\alpha_3 = (1 - e_1^2)(1 - e_2^2)(1 - e_3^2)\alpha_0 \quad (24)$$

$$\beta_3 = (1 - e_0^2)(1 - e_2^2)(1 - e_3^2)\beta_0 \quad (25)$$

$$\gamma_3 = (1 - e_0^2)(1 - e_1^2)(1 - e_3^2)\gamma_0 \quad (26)$$

$$\delta_3 = (1 - e_0^2)(1 - e_1^2)(1 - e_2^2)\delta_0 \quad (27)$$

Figure 39:
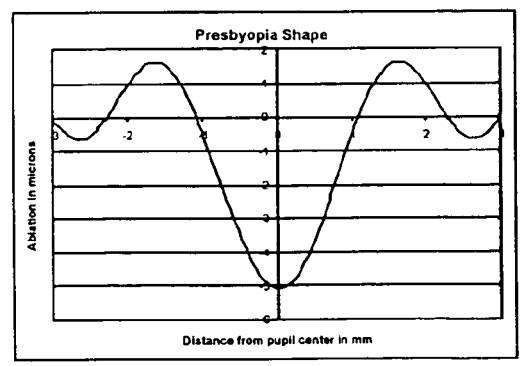
FIGS. 39 and 40 graphically illustrate a presbyopia-mitigating prescription derived so as to provide appropriate effective powers at four differing viewing conditions for a particular patient.
Figure 40:
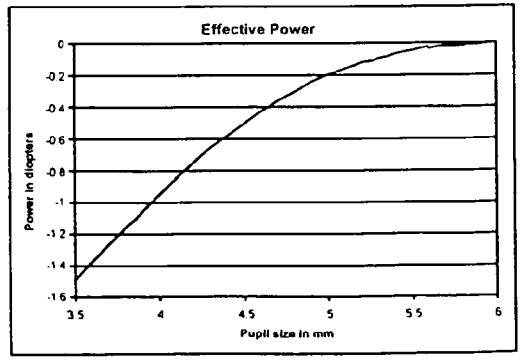

As an example, let's consider a pupil with WaveScan pupil size of 6 mm, and dim distance pupil size of 6 mm, requesting effective power of 0 D and bright reading pupil size of 3.5 mm, requesting effective power of −1.5 D . We also request that the bright distance pupil size to be 5 mm and dim reading pupil size of 4.5 mm, with effective power of −0.2 D and −0.5 D , respectively. Substituting $e_0 = 6/6 = 1$, $e_1 = 5/6 = 0.833$, $e_2 = 4.5/6 = 0.75$ and $e_3 = 3.5/6 = 0.583$ as well as $p_0 = 0$, $p_1 = −0.2$, $p_2 = −0.5$ and $p_3 = −1.5$, we get $c_2^0 = 0$, $c_4 = −0.2919$, $c_6 = 0.3523$ and $c_8 = −0.105$. FIGS. 39 and 40 show the presbyopia shape and the effective power as a function of pupil sizes. Note that both the presbyopia shape and the effective power are similar to those shown in FIGS. 37 and 38. However, the shape and power given with 4-term solution is smoother and have a flatter power at larger pupil sizes.

It is also possible to use the same approach to obtain analytical solutions for conditions that use more than four power points. For example, when we use five power points, we could use up to $10^{th}$ order of Zernike coefficients to describe the aspheric shape that satisfies the power profile defined with five power points. Similarly, six power points can define an aspheric shape using $12^{th}$ order of Zernike coefficients. Because more power points can in general make the analytical solution more difficult, another way of approaching the solution is by more complex numerical algorithms. Due to the availability of the recursive formula, the equations that lead to analytical solutions might be converted to an eigen system problem, which does have numerical solutions, optionally making use of the methods of William H Press, Saul A. Teukolsky, William Vetterling, and Brian P. Flannery, in *Numerical Recipes in C++*, (Cambridge University Press, 2002). Such a solution may be more accurate than use of discrete power point.

Discussion

The first thing we want to discuss is how many terms we should use in determining the presbyopia shape. In the two-power-term solution, we use the pupil sizes as well as the corresponding desired powers. Obviously, we can use this solution for a somewhat "bifocal" design with one distance pupil size and power (which should be zero to keep the eye at emmetropia) and one reading pupil size and its corresponding power. From FIGS. 35 and 36, the effective power follows a rather linear relationship with pupil size changes. This may not be ideal in that the distance power may tend to become myopic. With a 3-power-term solution, we have one more freedom to choose the power in a middle pupil size and in fact the solution is rather close to a 4-power-term solution when carefully designed. Unfortunately, with a 3-power-term solution, the bright distance pupil and the dim reading pupil tend to be averaged and so do the corresponding powers. This may become too inflexible to design an ideal shape. Therefore, the 4-power-term solution, which tends to give a more favorable reverse Z-curve, should be used in the practical implementation. The reverse Z-curve such as that shown in FIG. 41A, a positive power gradient region between two lower slope (or flat) regions within a pupil size variation range for a particular eye, may be a beneficial effective power characteristic for presbyopia mitigation.

Figure 41A:
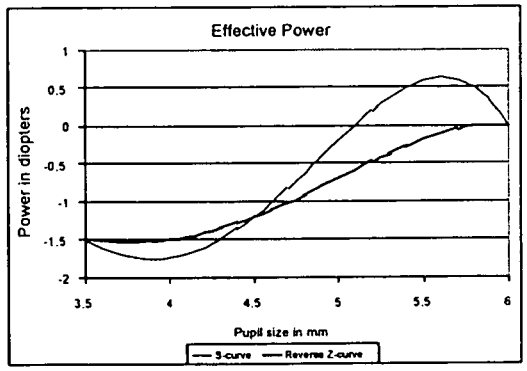
FIGS. 41A and 41B graphically illustrate different presbyopia-mitigating prescriptions which provide differing effective power variation characteristics during pupil size changes under differing viewing conditions.
Figure 41B:
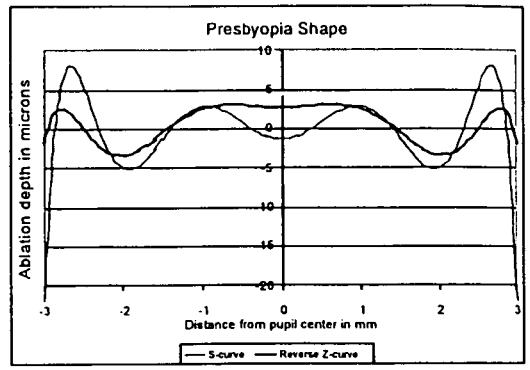

Even with a 4-power-term solution, choosing effective powers in-between dim distance pupil and bright reading pupil should be carefully considered. For instance, in order to satisfy restaurant menu reading, we might want to increase the power for dim reading. In this case, an unfavorable S-curve would exist, as is also shown in FIG. 41A. Presbyopia-mitigation shapes corresponding to the S-curve and Z-curve shapes are shown in FIG. 41B. These results were generated for a 6 mm pupil with the dim distance pupil at 6 mm with a power of 0 D , the bright distance pupil at 5 mm with power of −0.2 D and −0.7 D , the dim reading pupil at 4.5 mm with a power of −1.2 D and the bright reading pupil at 3.5 mm with a power of −1.5 D . To reduce the fluctuation of effective power, we can also increase the power in bright distance and in this case the distance vision can be affected (in addition to the contrast drop due to asphericity).

Another parameter we can set is desired reading power. Optionally we can give the patient full power; say 2.5 D , so the treatment can be sufficient to treat presbyopia for the patient's life span. However, the natural pupil size decreases with increasing age. Therefore, a shape well suited to a patient at the age of 45 could become deleterious at the age of 60. Secondly, not everyone easily tolerates asphericity. Furthermore, too much asphericity can reduce the contrast sensitivity to a level that distance vision would deteriorate. As such, measurement of a patient's residual accommodation becomes beneficial in the success of presbyopia correction. In addition, the various pupil sizes at different lighting conditions and accommodation can be measured systematically and more accurately. Such measurements may employ, for example, a commercially available pupilometer sold by PROCYON under the model number P-2000. A wide variety of alternative pupil measurement techniques might be used, including visual measurements, optionally using a microscope displaying a scale and/or reticule of known size superimposed on the eye, similar to those employed on laser eye surgery systems commercially available from VISX, INCORPORATED of Santa Clara, Calif.

The influence of high order aberrations on the effective power, as described above regarding the power map, may also be incorporated into the presbyopia-mitigating shape calculations. This may involve integration over the entire power map, i.e., the average power, with appropriate adjustment so as to avoid overestimating power (that may otherwise not agree with the minimum root-mean-squares (RMS) criterion) and so as to correlate with patient data. The influence of high order spherical aberrations on effective power calculation should not be entirely ignored. In particular, the influence on the depth of focus, and hence to the blur range during manifest refraction test, can be determined using clinical testing.

Figure 42:
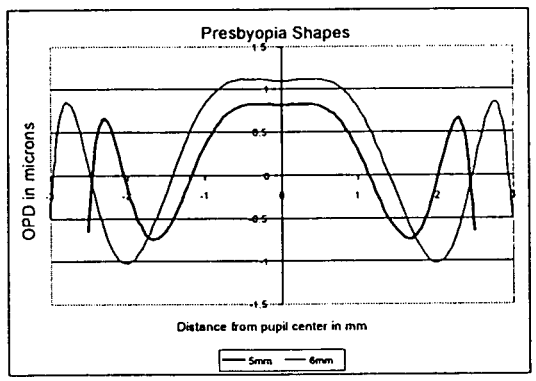
FIGS. 42 and 43 graphically illustrate effects of different pupil sizes on derived presbyopia-mitigating prescriptions and their optical characteristics.
Figure 43:
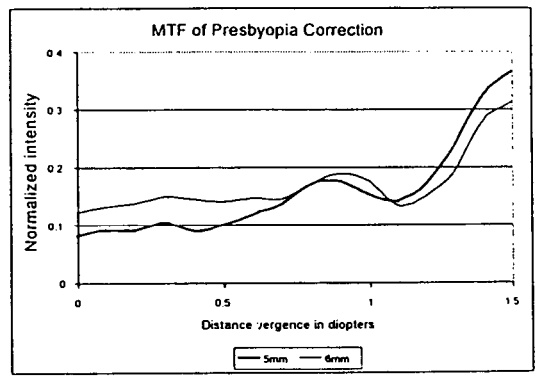
Figure 44:
FIG. 44 illustrates simulated eye-chart letters as viewed with a presbyopic eye treated with a presbyopia-mitigating prescription derived for a particular patient.
Figure 44:

Taking advantage of the ability to calculate presbyopia shapes based on effective power, presbyopia-mitigating shapes can be derived and/or optimized based on the following considerations. First, image quality of the presbyopia shape at different viewing conditions can be evaluated. To do so, optimization of the shape itself can be pursued. This can be done in several ways, such as using diffraction optics (wave optics) or geometrical optics (ray tracing). Because we are dealing with aberrations of many waves, it may be impractical to use point spread function based optical metrics. However, since the aberration we introduce belongs to high orders only, wave optics may still work well. In fact, a comparison of Zemax modeling with three wavelengths and using verification tools (wave optics), as shown in FIG. 13, with 7-wavelengths show almost identical results in both point spread function (PSF) and modulation transfer function (MTF). FIG. 42 shows some derived shapes for a 5 mm and a 6 mm pupil, while the corresponding MTF curves are shown in FIG. 43. The simulated blurring of eye chart letter E for both cases is shown in FIG. 44. These letters graphically illustrate verification of presbyopia shape using a goal function with 7-wavelengths polychromatic PSF and a 20/20 target. The first image shows a target at 10 m. The second to the last image shows targets from 1 m to 40 cm, separated by 0.1 D in vergence. One diopter of residual accommodation is assumed for each. Even without optimization, the optical surface shown gives almost 20/20 visual acuity over 1.5 D vergence.

The above approach is valid to apply in contact lens, intra-ocular lens, as well as spectacles, as well as refractive surgery. Such calculations for refractive surgery may be adjusted for the healing effect as well as the LASIK flap effect based on empirical studies and clinical experience.

As established above, it is possible to obtain analytical expressions for the Zernike coefficients of the first few spherical aberrations of different orders to create an aspheric shape for presbyopia correction based on one or more desired effective powers. Healing effect, flap effect, and the correlation of effective power with manifest refraction will benefit from additional patient data and empirical studies to further refine the presbyopia shape so as to (for example) more accurately plan the shape for future ablation.

Each of the above calculations may be performed using a computer or other processor having hardware, software, and/or firmware. The various method steps may be performed by modules, and the modules may comprise any of a wide variety of digital and/or analog data processing hardware and/or software arranged to perform the method steps described herein. The modules optionally comprising data processing hardware adapted to perform one or more of these steps by having appropriate machine programming code associated therewith, the modules for two or more steps (or portions of two or more steps) being integrated into a single processor board or separated into different processor boards in any of a wide variety of integrated and/or distributed processing architectures. These methods and systems will often employ a tangible media embodying machine-readable code with instructions for performing the method steps described above. Suitable tangible media may comprise a memory (including a volatile memory and/or a non-volatile memory), a storage media (such as a magnetic recording on a floppy disk, a hard disk, a tape, or the like; on an optical memory such as a CD, a CD-R/W, a CD-ROM, a DVD, or the like; or any other digital or analog storage media), or the like.

As the analytical solutions described herein some or all of these method steps may be performed with computer processors of modest capability, i.e., a 386 processor from Intel™ may be enough to calculate the Zernike coefficients, and even 286 processor may be fine. Scaling of Zernike coefficients was described by Jim Schweigerling, "*Scaling Zernike Expansion Coefficients to Different Pupil Sizes,*" *J. Opt. Soc. Am.* A 19, pp 1937-1945 (2002). No special memory is needed (i.e., no buffers, all can be done as regular variables or using registers). Also, it can be written in any of a wide variety of computer languages, with the exemplary embodiment employing C++. This exemplary embodiment comprises code which performs the Zernike coefficient calculation, shape combination (combining a regular aberration treatment prescription as well as the presbyopia shape), and provides graphical output for reporting purpose. It was written in C++ with Borland C++ Builder™ 6, and it is run with a laptop of 1.13 GHz CPU having 512 Mb of memory.

Figure 45B:
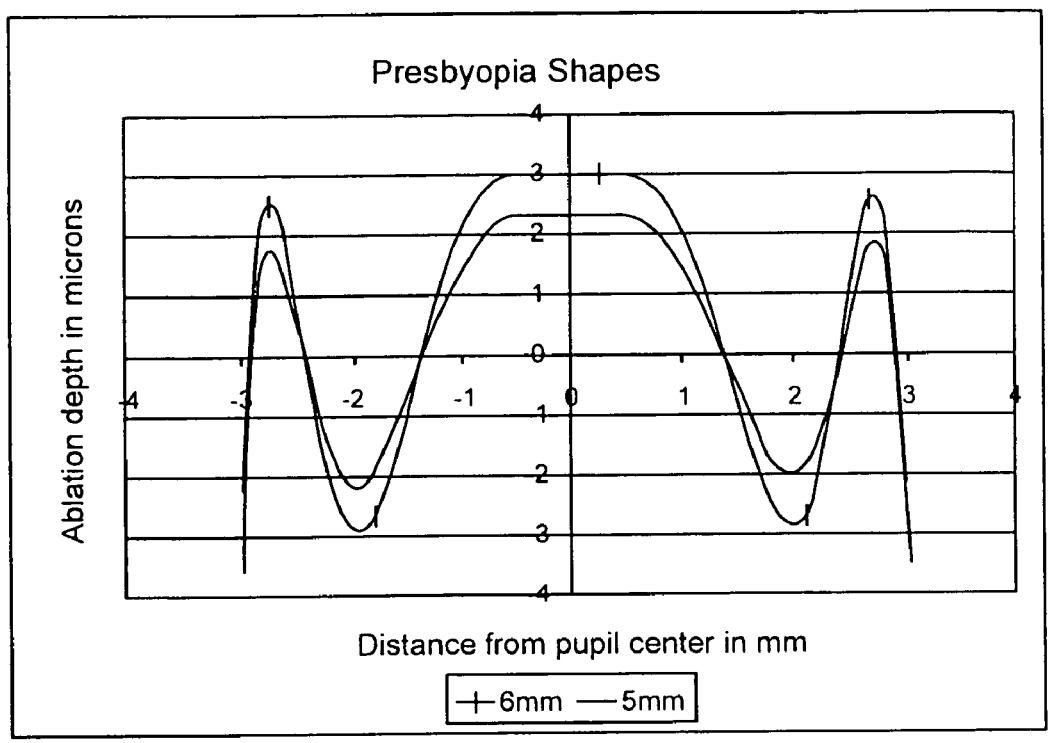
FIGS. 45A and 45B illustrate an exemplary power/pupil correlation and corresponding presbyopia prescription.
Figure 45A:
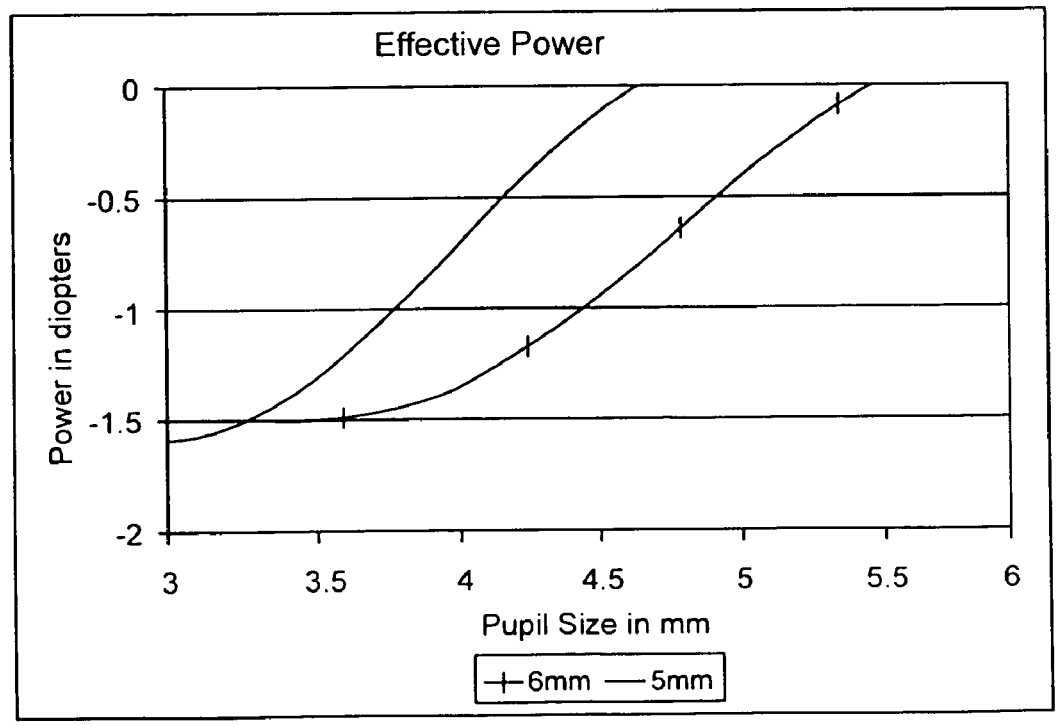

FIGS. 45A and 45B illustrate exemplary desired power curves and treatment shapes for mitigating presbyopia of a particular patient. The four power point solution was used to establish these shapes. For a 6 mm pupil, the following table describes the four conditions or set points from which the shape was generated:

TABLE 5

| | 6 mm Pupil | | 5 mm Pupil | |
|---|---|---|---|---|
| Conditions | Effective power | Pupil size (mm) | Effective power | Pupil size (mm) |
| 1 | 0 D | 6 | 0 D | 5 |
| 2 | −0.5 D | 5 | −0.5 D | 4.2 |
| 3 | −1 D | 4.5 | −1 D | 3.8 |
| 4 | −1.5 D | 3.4 | −1.55 D | 3.1 |

FIG. 45A shows the effective power profiles, while FIG. 45B shows the corresponding presbyopia shapes. To model the healing and LASIK flap effect, we uniformly boost the shape by 15%. In addition to the added presbyopia shape, we also used −0.6 D physician adjustment in the wavefront prescription generation to offset myopic bias to aim emmetropia at normal viewing condition (bright distance) after surgery.

While the exemplary embodiments have been described in some detail, by way of example and for clarity of understanding, those of skill in the art will recognize that a variety of modification, adaptations, and changes may be employed. Hence, the scope of the present invention should be limited solely by the claims.

What is claimed is:

1. A system for treating existing and/or potential presbyopia a patient, the patient having an eye with a pupil, a change in viewing distance with the eye inducing a change in pupil dimension, the system comprising:
   a device for measuring a first dimension of the pupil while the eye is viewing at a first viewing distance;
   a prescription generating module having an input accepting a desired power for the eye and the first dimension, the module comprising a tangible medium embodying machine-readable code for determining a prescription for the eye providing a first desired power when the pupil has the first dimension, the prescription effecting a desired change in power in response to the change in pupil dimension, the desired change in power mitigating the presbyopia.

2. The system of claim 1, wherein the pupil measurement device comprises a pupilometer, and wherein the prescription generating module comprises at least one member selected from the group consisting of:
   an optimizer module comprising a tangible medium embodying machine-readable code that determines the prescription based on the pupil diameter and the desired power using a goal function appropriate for the presbyopia;
   a scaling module comprising a tangible medium embodying machine-readable code that scales a central portion of a prescription shape based on the pupil dimension such that the prescription shape ameliorates presbyopia, and such that the central portion has a dimension between about 0.35 and about 0.55 of the pupil dimension; and
   a prescription calculating module, the module comprising a tangible medium embodying machine-readable code for calculating a presbyopia-mitigating prescription for the eye in response to the pupil dimension and the change in pupil dimension so that the eye has the first desired power suitable for the first viewing distance and so that the eye has a second desired power for a second viewing distance.

3. A method for determining a prescription that mitigates or treats presbyopia in a particular patient, the method comprising:
   (a) selecting a goal function appropriate for presbyopia of an eye;
   (b) inputting a set of patient parameters specific for the particular patient; and
   (c) determining an optical shape for the particular patient appropriate for differing viewing conditions based on the set of patient parameters per the goal function so as to mitigate or treat the presbyopia in the patient.

4. The method of claim 3, wherein the goal function reflects optical quality throughout a vergence range.

5. The method of claim 3, wherein the goal function comprises a ratio of an optical parameter of the eye with a diffraction theory parameter.

6. The method of claim 5, wherein the goal function comprises at least one parameter selected from the group consisting of Strehl Ratio (SR), modulation transfer function (MTF), point spread function (PSF), encircled energy (EE), MTF volume or volume under MTF surface (MTFV), compound modulation transfer function (CMTF), and contrast sensitivity (CS).

7. The method of claim 6, wherein the optical shape is determined such that it has a value of about 25% CMTF over a vergence.

8. The method of claim 3, wherein the goal function is based on geometrical optics.

9. The method of claim 8, wherein the goal function is determined using ray tracing.

10. The method of claim 3, wherein the set of patient parameters comprises at least one parameter selected from the group consisting of pupil size, residual accommodation, and desired power.

11. The method of claim 10, further wherein additional patient parameters comprise at least one of the group consisting of preferences for distance or near sight, preferences for sight under bright or dim conditions, and preferences for contrast sensitivity.

12. The method of claim 3, wherein the optical shape is further determined based on an expansion selected from the group consisting of a regular polynomial (EPTP or non-EPTP), a Zernike polynomial, a Fourier series, and a discrete shape entirety.

13. The method of claim 3, wherein the optical shape is further determined based on a presbyopia-add to pupil ratio (PAR), the PAR ranging from about 0.2 to about 1.0.

14. The method of claim 12, wherein the expansion is a 3rd order or 4th order non-EPTP expansion.

15. The method of claim 12, wherein the expansion is a 6th order or 8th order EPTP expansion.

16. The method of claim 3, wherein the optical shape has an optimizer value of about 5.0 or smaller.

17. A method for establishing a prescription that mitigates or treats presbyopia of an eye in a particular patient, the method comprising:
   (a) inputting a set of patient parameters specific for the particular patient into an optimizer module comprising a tangible medium embodying machine-readable code; and
   (b) deriving a prescription for the particular patient with the machine-readable code of the optimizer module per a goal function, the goal function related to a plurality of viewing conditions, so as to mitigate or treat the presbyopia in the patient.

18. The method of claim 17, further comprising inputting a radially symmetric initial optical shape.

19. The method of claim 18, wherein the radially symmetric shape is decomposed into a set of polynomials having at least two independent variables.

20. The method of claim 19, wherein one of the at least two independent variables is the ratio of a customized prescription shape diameter to pupil diameter.

21. The method of claim 17, wherein the goal function comprises a ratio of an optical parameter of the eye with a diffraction theory parameter.

22. The method of claim 17, wherein the optimizer module is configured to employ a method selected from the group consisting of Downhill Simplex method, Direction set method, and Simulated Annealing method.

23. A method for treating or mitigating presbyopia in a particular patient, the method comprising:
   (a) selecting a goal function appropriate for presbyopia of an eye;
   (b) inputting a set of patient parameters specific for the particular patient;
   (c) determining an optical shape for the particular patient based on the set of patient parameters per the goal function; and
   (d) mitigating or treating the presbyopia in the patient by administering to the patient a procedure selected from the group consisting of:

(i) ablating a corneal surface of the patient to provide a corneal shape that corresponds to the optical shape, (ii) providing the patient with a contact lens or spectacle lens that has a shape that corresponds to the optical shape, and (iii) providing the patient with an intra-ocular lens that has a shape that corresponds to the optical shape.

24. A system for establishing a prescription that mitigates or treats presbyopia in a particular patient, the system comprising:

(a) an input that accepts a set of patient parameters; and (b) an optimizer module comprising a tangible medium embodying machine-readable code that determines the prescription for the particular patient based on the set of patient parameters, using a goal function appropriate for presbyopia of an eye.

25. The system of claim 24, wherein the goal function reflects optical quality throughout a vergence range.

26. The system of claim 24, wherein the goal function comprises a ratio of an optical parameter of the eye with a diffraction theory parameter.

27. The system of claim 26, wherein the goal function comprises at least one parameter selected from the group consisting of Strehl Ratio (CS), modulation transfer function (MTF), point spread function (PSF), encircled energy (EE), MTF volume or volume under MTF surface (MTFV), compound modulation transfer function (CMTF), and contrast sensitivity (CS).

28. The system of claim 24, wherein the goal function is based on geometrical optics.

29. The system of claim 28, wherein the goal function is determined using ray tracing.

30. The system of claim 24, wherein the set of patient parameters comprises at least one parameter selected from the group consisting of pupil size, residual accommodation, and power need.

31. The system of claim 24, wherein the module comprises a tangible medium embodying machine-readable code that makes use of an initial optical shape, a set of initial conditions, and the set of patient parameters for an iterative optimization so as to establish an optical shape for the particular patient, using a goal function appropriate for presbyopia of an eye.

32. The system of claim 31, wherein the initial optical shape is radially symmetric.

33. The system of claim 32, wherein the radially symmetric shape is decomposed by the module into a set of polynomials having at least two independent variables.

34. The system of claim 33, wherein one of the at least two independent variables is the ratio of the customized shape diameter to pupil diameter.

35. The system of claim 31, wherein the goal function comprises a ratio of an optical parameter of the eye with a diffraction theory parameter.

36. The system of claim 31, wherein the optimizer module comprises a tangible medium embodying machine-readable code that is configured to employ a method selected from the group consisting of Downhill Simplex optimization, Direction set optimization, and Simulated Annealing optimization.

37. The system of claim 31, wherein the set of patient parameters comprises at least one parameter selected from the group consisting of pupil size, residual accommodation, and desired power.

38. A system for reprofiling a surface of a cornea of an eye of a particular patient from a first shape to a second shape having correctively improved optical properties, the system comprising:

(a) an input that accepts a set of patient parameters;

(b) a module comprising a tangible medium embodying machine-readable code that determines an optical shape for the particular patient based on the set of patient parameters, using a goal function appropriate for presbyopia of an eye;

(c) a processor that generates an ablation profile; and (d) a laser system that directs laser energy onto the cornea according to the ablation profile so as to reprofile a surface of the cornea from the first shape to the second shape, the second shape corresponding to the determined optical shape.

39. A method for defining a prescription for treating presbyopia in a particular patient, the method comprising:

(a) providing an optical shape configured to treat the vision condition;

(b) determining a pupil diameter of the particular patient; and (c) defining a prescription shape comprising a central portion, the central portion having a dimension within a range between about 0.35 and about 0.55 of the pupil diameter, the prescription shape based on:

(i) the pupil diameter;

(ii) an inner region of the optical shape; and (iii) an attribute of at least one eye previously treated with the optical shape.

40. The method of claim 39, wherein the pupil diameter of the particular patient comprises a diameter based on at least one member selected from the group consisting of:

(a) a pupil diameter as measured when focusing on a near object;

(b) a pupil diameter as measured when focusing on a distant object;

(c) a pupil diameter as measured under photopic conditions;

(d) a pupil diameter as measured under mesopic conditions; and (e) a pupil diameter as measured under scotopic conditions.

41. The method of claim 39, wherein the prescription shape is aspherical, and the central portion of the prescription shape is aspherical; the prescription shape is spherical and the central portion of the prescription shape is spherical; the prescription shape is aspherical, and the central portion of the prescription shape is spherical; or the prescription shape is spherical, and the central portion of the prescription shape is aspherical.

42. The method of claim 39, wherein the dimension of the prescription shape central portion comprises a diameter of the central portion and remains within a range between about 0.4 and about 0.5 of the pupil diameter of the particular patient.

43. The method of claim 39, wherein the dimension of the central portion comprises a diameter of the central portion and remains within a range between about 0.43 and about 0.46 of the pupil diameter of the particular patient.

44. The method of claim 39, wherein a power of the central portion is between about 1.5 diopters and about 4.0 diopters.

45. The method of claim 39, wherein a power of the central portion is about 3.1 diopters.

46. The method of claim 39, further comprising:

(d) treating the particular patient's eye with the defined prescription shape such that the presbyopia of the patient is ameliorated.

47. The method of claim 46, wherein the prescription shape is defined such that following treatment an acuity measurement of the particular patient's eye is optimized.

48. The method of claim 46, wherein the treating comprises administering to the particular patient a procedure selected from the group consisting of:

(a) ablating a corneal surface of the patient to provide a corneal surface shape having a dimension that corresponds to a dimension of the defined prescription shape, (b) providing the patient with a contact lens having a dimension that corresponds to a dimension of the defined prescription shape, and (c) providing the patient with an intra-ocular lens having a dimension that corresponds to a dimension of the defined refractive shape.

49. The method of claim 46, wherein the defined prescription shape includes an aspheric portion.

50. A system for scaling a prescription shape that treats a vision condition in a particular patient, the system comprising:

(a) an input that accepts a prescriptive shape specific for treating the vision condition;

(b) an input that accepts a pupil dimension of the particular patient; and (c) a module comprising a tangible medium embodying machine-readable code that scales a central portion of the prescription shape based on the pupil dimension of the particular patient and an attribute of at least one eye previously treated with the prescriptive shape such that the prescription shape ameliorates an indication of the vision condition of the particular patient, and such that the central portion has dimension between about 0.35 and about 0.55 of the pupil diameter.

51. The system of claim 50, further comprising:

(d) a processor that generates an ablation profile; and (e) a laser system that directs laser energy onto the cornea according to the ablation profile so as to reprofile a surface of the cornea according to the prescription shape.

52. A method for treating presbyopia of an eye of a patient, the method comprising:

identifying a first pupil size of the eye under a first viewing condition;

identifying a second pupil size of the eye under a second viewing condition; and calculating a presbyopia-mitigating prescription for the eye in response to the pupil sizes so that the eye has a first power suitable for the first viewing condition at the first size and so that the eye has a second power suitable for the second viewing condition at the second size, wherein calculating the prescription comprises determining at least one coefficient of a set of Zernike polynomials.

53. The method of claim 52, wherein calculating the prescription comprises determining a plurality of selected Zernike coefficients of spherical aberration at various orders.

54. A method for determining an effective power of an eye under a viewing condition, the method comprising:

determining a plurality of coefficients of a Zernike polynomial expansion from a wave front of an eye while the eye has a first pupil size;

determining a second pupil size of the pupil under the viewing condition;

calculating the effective power of the eye from at least one of the coefficients of the Zernike polynomial from a relationship between effective power and pupil size.

55. A system for deriving a prescription for an eye, the system comprising:

a polynomial expansion module having an input for a wavefront of an eye and an output for a polynomial expansion, the polynomial expansion module comprising a tangible medium embodying machine-readable code that determines the polynomial expansion from the wavefront of the eye;

an effective power module having an input coupled to the output of the polynomial expansion module and an output, the effective power module comprising a tangible medium embodying machine-readable code that determines an effective power from the polynomial expansion; and a prescription module coupled to the effective power module, the prescription module comprising a tangible medium embodying machine-readable code that generates the prescription so as to provide a plurality of different desired effective powers at an associated plurality of different viewing pupil sizes.

56. A system for determining an effective power of an eye under a viewing condition, the system comprising:

a first input for a plurality of coefficients of a Zernike polynomial expansion from a wavefront of an eye while the eye has a first pupil size;

a second input for a second pupil size of the pupil under the viewing condition;

an effective power calculating module comprising a tangible medium embodying machine-readable code that calculates the effective power of the eye from at least one of the coefficients of the Zernike polynomial and a relationship between effective power and pupil size.

* * * * *